United States Patent
Ogi et al.

(10) Patent No.: US 6,613,887 B1
(45) Date of Patent: Sep. 2, 2003

(54) HUMAN EPENDYMIN-LIKE PROTEIN

(75) Inventors: Kazuhiro Ogi, Tsukuba (JP); Haruo Onda, Tsuchiura (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/242,890

(22) PCT Filed: Sep. 10, 1997

(86) PCT No.: PCT/JP97/03194

§ 371 (c)(1),
(2), (4) Date: Feb. 25, 1999

(87) PCT Pub. No.: WO98/11130

PCT Pub. Date: Mar. 19, 1998

(30) Foreign Application Priority Data

| Sep. 11, 1996 | (JP) | 8-240880 |
| Nov. 28, 1996 | (JP) | 8-318049 |
| May 27, 1997 | (JP) | 9-135633 |

(51) Int. Cl.$^7$ ............................................. C07K 14/48
(52) U.S. Cl. ........................ 530/399; 530/350; 930/10
(58) Field of Search ................ 530/350, 399; 930/10

(56) References Cited

FOREIGN PATENT DOCUMENTS

WO    WO 92 20362 A    11/1992

OTHER PUBLICATIONS

Rudiger In "Peptide Hormones" (ed. J.A. Parsons) University Park Press, Baltimore, pp. 1–7, 1976.*
Shashoua et al. J. Neurosci. Res. 32: 239–244, 1992.*
Schmidt, R. et al., "Immunological cross–reactivity of cultured rat hippocampal neurons . . . " Brain Research, 386, 1986; pp. 245–257.
Müller–Schmid, A. et al., "Molecular analysis of ependymins . . . " J. Mol. Evol., 36, 1993; pp. 578–585.
Hoffmann, W. & Schwarz, H., "Ependymins: Meningeal–derived extracellular matrix proteins at the blood–brain barrier" Int. Rev. Cytol., 165, 1966; pp. 121–158.
Müller–Schmid, A. et al., "Ependymins from the cerebrospinal fluid of salmoid fish: . . . " Gene, 118, 1992; pp. 189–196.
Ortí, G. & Meyer, A., "Molecular Evolution of Ependymin and the Phylogenetic Resolution of Early Divergences Among Euteleost Fishes" Mol. Biol. Evol., 13(4), 1996; pp. 556–573.
Adams, D. et al., "Genes Encoding Giant Danio and Golden Shiner Ependymin" Neurochemical Research, 21(3), 1996; pp. 377–384.

* cited by examiner

*Primary Examiner*—Gary Kunz
*Assistant Examiner*—Robert C. Hayes
(74) *Attorney, Agent, or Firm*—Mark Chao; Elaine M. Ramesh

(57) ABSTRACT

The invention provides an ependymin-like protein derived from a mammal, or its partial peptide or its precursor protein, or a salt thereof; a signal peptide; a DNA coding for the protein, etc. a recombinant vector; a transformant; a method of producing the protein; a pharmaceutical composition comprising the protein, etc. or DNA, an antibody against the protein, etc.; and a method for screening and a screening kit for compounds promoting the function of the protein. The protein, its partial peptide or a salt thereof has physiological activities such as a nerve-extending or nerve-regenerating activity, a gliacyte stimulating activity, and so on. The protein, etc. or the DNA is useful as a therapeutic or prophylactic agent for Alzheimer's disease, Parkinson's disease, Huntington's disease, amyotrophic lateral sclerosis (ALS), dementia or cerebellar degeneration. The antibody against the protein, etc. can be used in the assay of the protein, etc. in a test sample. Furthermore, the protein, etc. is useful as a screening reagent for compounds or their salts capable of promoting the function of the protein.

3 Claims, 17 Drawing Sheets

Fig. 1 (A)

| | |
|---|---:|
| CAGTGGCAGCAGGCAGTGGCAGCAGGCAGTGGCCCA | 36 |
| GGCAGAAATAGCTCCCGCGCGATTCACTGGAGCCTT | 72 |
| CCCCGGGCCCTGGTCCCGGCTACCGGGACTCGCGCG | 108 |
| TCCGGATCTCAAAAGCGGCAGAGGCCACCGAAGGGA | 144 |
| CAGGAAGCACTTTGGTCCAGACCACACTCCCGGCAC | 180 |
| AGTGCGGAAAGAGCCGGCGGGAGCCACTCTGATCCC | 216 |
| GGACGCCTCAGCGCCCCTTGGGCTTGGGCTTGCCC | 252 |

| | |
|---|---:|
| TCGGGCCGGGGAAGGCTGACCGCGATGCCAGGACGC | 288 |
|                               MetProGlyArg | 4 |

| | |
|---|---:|
| GCTCCCCTCCGCACCGTCCCGGGCGCCCTGGGTGCC | 324 |
| AlaProLeuArgThrValProGlyAlaLeuGlyAla | 16 |

| | |
|---|---:|
| TGGCTGCTGGGCGGCCTCTGGGCCTGGACCCTGTGC | 360 |
| TrpLeuLeuGlyGlyLeuTrpAlaTrpThrLeuCys | 28 |

| | |
|---|---:|
| GGCCTGTGCAGCCTGGGGGCGGTGGGAGCCCCGCGC | 396 |
| GlyLeuCysSerLeuGlyAlaValGlyAlaProArg | 40 |

| | |
|---|---:|
| CCGTGCCAGGCGCCGCAGCAGTGGGAGGGGCGCCAG | 432 |
| ProCysGlnAlaProGlnGlnTrpGluGlyArgGln | 52 |

| | |
|---|---:|
| GTTATGTACCAGCAAAGTAGCGGGCGCAACAGCCGC | 468 |
| ValMetTyrGlnGlnSerSerGlyArgAsnSerArg | 64 |

| | |
|---|---:|
| GCCCTGCTCTCCTACGACGGGCTCAACCAGCGCGTG | 504 |
| AlaLeuLeuSerTyrAspGlyLeuAsnGlnArgVal | 76 |

| | |
|---|---:|
| CGGGTGCTGGACGAGAGGAAGGCGCTGATCCCCTGC | 540 |
| ArgValLeuAspGluArgLysAlaLeuIleProCys | 88 |

| | |
|---|---:|
| AAGAGATTATTTGAATATATTTTGCTGTATAAGGAT | 576 |
| LysArgLeuPheGluTyrIleLeuLeuTyrLysAsp | 100 |

Fig. 1 (B)

```
GGAGTGATGTTTCAGATTGACCAAGCCACCAAGCAG    612
GlyValMetPheGlnIleAspGlnAlaThrLysGln    112

TGCTCAAAGATGACCCTGACACAGCCCTGGGATCCT    648
CysSerLysMetThrLeuThrGlnProTrpAspPro    124

CTTGACATTCCTCAAAACTCCACCTTTGAAGACCAG    684
LeuAspIleProGlnAsnSerThrPheGluAspGln    136

TACTCCATCGGGGGCCTCAGGAGCAGATCACCGTC    720
TyrSerIleGlyGlyProGlnGluGlnIleThrVal    148

CAGGAGTGGTCGGACAGAAAGTCAGCTAGATCCTAT    756
GlnGluTrpSerAspArgLysSerAlaArgSerTyr    160

GAAACCTGGATTGGCATCTATACAGTCAAGGATTGC    792
GluThrTrpIleGlyIleTyrThrValLysAspCys    172

TATCCTGTCCAGGAAACCTTTACCATAAACTACAGT    828
TyrProValGlnGluThrPheThrIleAsnTyrSer    184

GTGATATTGTCTACGCGGTTTTTTGACATCCAGCTG    864
ValIleLeuSerThrArgPhePheAspIleGlnLeu    196

GGTATTAAAGACCCCTCGGTGTTTACCCCTCCAAGC    900
GlyIleLysAspProSerValPheThrProProSer    208

ACGTGCCAGATGGCCCAACTGGAGAAGATGAGCGAA    936
ThrCysGlnMetAlaGlnLeuGluLysMetSerGlu    220

GACTGCTCCTGGTGAGCCTGTGCATAGGGAAGCGGC    972
AspCysSerTrp***                        224

AGCATCGGATGTCAGCCCCTGCGGCCCCAGCTGGA   1008
GATGGATATGAGACTAGTCAAGATGTGAATGCTAAT   1044
TGGAGAGAAATATAATTTTAGGAAGATGCACATTGA   1080
```

Fig. 1 (C)

```
TGTGGGGTTTTGATGTGTCTGATTTTGACTACTCAA 1116
GCTCTGTTTACAGAAGAAATTGAATGGCGAGGGTG 1152
TGGCCATATGAACTGACTAGATGGCTAATATGGACA 1188
CTTTGGGTATTTCTAATGCCTGTTCAGGGCTGGTTT 1224
TCTGCATGCACGGGTATACACATAATGCAGTGCCAT 1260
GCACATAGGGAAGGGTCAGTAAGAGAAGTTTGCCTT 1296
GGCAGCAAGTATTTATTGTTGACATTATTCAGAATT 1332
AGTGATAATAAAAGCAGAGTGATTTTGGTCAATTT 1368
TATTATTAATTCTTAAATTCCTGCAGAGAATGCCC 1404
CCTTTATTGCTGCACCAGGGTGGGCATTGCTCCCAC 1440
TGAGCCCTACTCCACCCTGTCCCTGCACTCCCTTGG 1476
TTGCCAAAAAAATGATAACTTAAATCCCTTCCAGAC 1512
TTAAGAATTTTATGGCATGGCCCAATTGATATAAAC 1548
ATTTAGAAGGAAATGAAAGCTAAATAGGAAGTAA 1584
TTATTCCTCTAAAGAAACATTTTGAGCAAGGCAGTT 1620
TAGAGAATCCTAATGTCTACACTGGCATAGCACGAG 1656
CCATGTAAGCTTCTTTTTTTTCTATGCAAGAGTATT 1692
GATGTATGTGCTGAATCTTCACAGACTTGTCAATAC 1728
ACAGGCAGTATTCTAAAATAGCACTGAACAGGGAGT 1764
CAGGAGACTATTGTCTCCTAAACCCAGGACTAGAGT 1800
TCCCTCGTACTGTCACTCCTTTGGTCATTAAATGCA 1836
CTGGGCTTGCCCGCACTTTGGCCTTCCTAGAACGCT 1872
GCTTCATAACCTCTCTGTCTGACTTCTGCATCTCCT 1908
TCCAGGTCAGCTCATTCACAAGAGTTGCTCCCAAGC 1944
CTGGATGAGTTGCACCTTGCATCTTGAGCATGCATT 1980
TCTCACAATAATTATTAAGCTGTGTGATAATTTCTG 2016
CTTTCAGGACACTCATCCATTATCTTGGCTGTGAGC 2052
TCCTTGGGTACGGGTACCTTGTATGTTTAATTTTAT 2088
ATCCCTAGCACAAAGCAAGTGCCTGGCACATAGTCA 2124
GTGCCCTAAGTATTCGTAGAGTGAAGAATGCCAGCC 2160
TCTCTTGTCCCTGGTTTCCTTATGTGTTGAATGTGG 2196
TTGAGTTTGTCCATTGCTAGGGAGAGACTTCCAGTA 2232
ATAAAATTTACTATTCTAGATGCTTCTACTGTTATG 2268
```

Fig. 1 (D)

```
TTTTATCTGCCCATTTATCTTTCTTAGTTACCAGGA  2304
GAAATGTGTGACACCTATATTATAATGAAAACAATC  2340
TTATTACTTATAGTTTATCTATATTAAACAAATTTA  2376
ATTGCATTTTAAAGCATTCTTTGATATTGTTGCTTT  2412
TGCAATAAATATGGATAATCTTGGTTATAAGGAGT   2448
TAAAACAATGCTGTAATAAATAAAGTGTTTCATGTG  2484
ATCAAAAAAAAAAAAAAAAAA                 2507
```

Fig. 2 (A)

```
CCAGACTCGGACCCCCAAGCCGGAAGCCTCTAAAAC            36
AGAAAATTGGAAAATCGGAAAATCAGGAGAGGCCAG            72
GGCTCCTGAGCTGGTCCCAGAGCACATCTTCCACCA           108
GCGCTCAGACAACGCGCGTGACTCTCCACGCCGGG            144
CCTCGGCTCCCTCCCAGGTTTGGCTGACCCGGAGGG           180

CCGCGAATCACGATGCTCACACGCGCTCCCGCCGC            216
              MetLeuThrArgAlaProArgArg          8

CTGGTCCAGGGGCCCCGGGAGACCTGGCTGCTTGGC           252
LeuValGlnGlyProArgGluThrTrpLeuLeuGly            20

GGCTCTGGGTCTGGATATTGTGCGGCCTGGGGATG            288
GlyLeuTrpValTrpIleLeuCysGlyLeuGlyMet            32

GCGGGCTCCCCGGGAACCCCGCAGCCATGCCAGGCG           324
AlaGlySerProGlyThrProGlnProCysGlnAla            44

CCCCAGCAGTGGGAGGGACGTCAGGTTCTGTACCAG           360
ProGlnGlnTrpGluGlyArgGlnValLeuTyrGln            56

CAGAGCAGCGGGCACAACAGCCGCGCCCTGGTGTCC           396
GlnSerSerGlyHisAsnSerArgAlaLeuValSer            68

TACGATGGTCTCAACCAGCGCGTGCGGGTGCTGGAC           432
TyrAspGlyLeuAsnGlnArgValArgValLeuAsp            80

GAAAGGAAGGCGCTGATCCCCTGCAAGAGATTATTT           468
GluArgLysAlaLeuIleProCysLysArgLeuPhe            92

GAATACATTTTACTCTATAAGGATGGAGTGATGTTT           504
GluTyrIleLeuLeuTyrLysAspGlyValMetPhe           104

CAGATTGAACAAGCCACCAAACTGTGTGCAAAGATA           540
GlnIleGluGlnAlaThrLysLeuCysAlaLysIle           116
```

Fig. 2 (B)

```
CCCTTGGCAGAACCCTGGGATCCTCTCGACATTCCC       576
ProLeuAlaGluProTrpAspProLeuAspIlePro       128

CAGAATTCTACCTTTGAAGATCAGTACTCTATCGGA       612
GlnAsnSerThrPheGluAspGlnTyrSerIleGly       140

GGGCCTCAGGAGCAGATCATGGTCCAGGAATGGTCT       648
GlyProGlnGluGlnIleMetValGlnGluTrpSer       152

GACAGGAGGACAGCCAGATCCTATGAAACCTGGATT       684
AspArgArgThrAlaArgSerTyrGluThrTrpIle       164

GGCGTTTATACAGCCAAGGATTGCTACCCGGTCCAG       720
GlyValTyrThrAlaLysAspCysTyrProValGln       176

GAGACCTTCATTAGGAACTACACTGTGGTCCTGTCC       756
GluThrPheIleArgAsnTyrThrValValLeuSer       188

ACTCGGTTCTTTGATGTGCAGTTGGGCATTAAAGAC       792
ThrArgPhePheAspValGlnLeuGlyIleLysAsp       200

CCCTCTGTGTTCACCCCACCAAGCACGTGCCAGACA       828
ProSerValPheThrProProSerThrCysGlnThr       212

GCACAGCCAGAGAAGATGAAAGAGAACTGCTCCCTG       864
AlaGlnProGluLysMetLysGluAsnCysSerLeu       224

TGAATTTCCATGAGCGGAAGCCACGACCTCAGCTCT       900
***                                        224

TAGGGACTTTGTGTGGAAATGGACTAGAGGCCAGTT       936
GGAAAGCAACTCGTCACGAGAAGCAAAGCTAGTTTT       972
AGGAAGATAAACCCTATGTGGACTTGCTTGTCATCT      1008
GACTGTGGCTGCTCAGCTCTATTTTTGGAAGGAACC      1044
TGGGTTATCCTTTCTGTGTGCAGGTGTGTAGTCAGT      1080
GCTGTAGGGTAGGACGGGGTGAAGGTGGGGTCGGCA      1116
```

Fig. 2 (C)

```
CAAGGAGTTTGCCTCTGCAGAGTGAACCTTTTATTA  1152
TTGCCAATAAGATTGAAAGTGATAATAAGATATAGT  1188
ATAATTTTTTTCAGTTCTCTCCTTACAAAGAAAGTC  1224
CCTTGCTTGTGTGCACTAGGGTAGTGACAGTTCCCA  1260
CTGACCCCACACCTGCCTCTGGCTACTATGAGATGA  1296
CCCTTTAAGATTCTTTCCAAGCTTAAATTTTGTCAC  1332
ATGGCCCACCGGATGTAGATATTCTGCAAGGAAGTA  1368
GAAACTTGTAATGCAAAGCAATGTTGCCTCTGAAGG  1404
GAAAAGAAGTTTTAAGCGGGAGGCTTAGACAATCTT  1440
AGTATCTTCATGTGAGATGAAGTCCGAGCCGTGTGT  1476
GGTGCTTTGTGTGCAAGAGTACTGACTGCTGTGCTG  1512
AAACTATGTCTTTTCTAGCGGGCAAACAGGCTTGCA  1548
AAACAGCACTGAATTGGGAGGCCCCAAGTAAGGCC   1584
TAGGATTCTCTGCTACTCTAATCCTTTAAGTAGTAA  1620
ATGCACTAGGCTAATAGCTCTCGCCTTGCCTTTCTG  1656
GAAACTCTCTGTCTATATGACTACTGCTCACGCTTC  1692
CAACATCAGCTCACATGTGCCCCTGTGAGCTGCTC   1728
CAATGCCTGAATTCATTGCACCTTACAGCTTGGCAT  1764
GCCTTGCTCACAATACTCAGTATGCTGCGTGAGGAT  1800
TTCCTGATTACTGGAAACTAACCTCTGTTATCCTGG  1836
GTAAGAATCCCTTGAGTTACGGGTATCGTGTTCTGT  1872
TTACTAATATCTCCAGCACCAAGCAAGTGCCTGGCA  1908
CGTAGTCCGTGCCCAAACATTTGCAGAGAGGAGCT   1944
CATCAGCTCTGTCAGTGTTTAGTTTTCTCATCTATT  1980
AAACAGGGTTGGTTTTTCTGGTTGCTAGGGAGACTT  2016
GTACTAATGCAACCTACTGTTCTAGATTCTTTATCA  2052
CCGTGTTTCATTTGACCACGTATCACCTTTTGTTAT  2088
CAAGAGAAATGTGTGAAGCTTGCTTTATGCTGTAGC  2124
CATCTATATTGTAATTTATCTCTATACAATTAAACA  2160
AATTTATTGACACCCTAAAAAAAAAAAAAAAAAAAA  2196
AAAAAA                                2202
```

Fig. 3 (A)

```
GCAGAGAGCAGGAAAAACAAGCTTTGGTAAGCCTCC           36
GCCAGAGCAGAAAGAGCTGGGGCGATTCACGCGGCT           72
TTCCCAGGCCGGTGTCCCGGTGTCCGGAGCCCCCAA          108
GCCAGGAGCCTGTGGAACGGAAATCGAGAGAGGCC           144
TGAACTGGGTCCCGGAGCACACCTTTCGCCAGGGCG          180
CAGAGAAGGCTCACGCGACTAGTCCAACGCAGGGCC          216
TCGGCTCTCTCTGGAGCTCGGCTGACCCTGGGGCGG          252

CAGATCACGATGCCCGCGCGCGCTCCCCGCCGCCTG          288
          MetProAlaArgAlaProArgArgLeu           9

GTCCAGGGGCCTCGGGGGACCTGGCTGCTGGGAAGC          324
ValGlnGlyProArgGlyThrTrpLeuLeuGlySer           21

CTCTGGGTCTGGGTGCTGTGCGGCCTGGGGATGGCG          360
LeuTrpValTrpValLeuCysGlyLeuGlyMetAla           33

GGCTCCCTGGGAACCCCACAGCCATGCCAGGCACCC          396
GlySerLeuGlyThrProGlnProCysGlnAlaPro           45

CAGCAGTGGGAGGGACGCCAGGTTCTGTACCAGCAG          432
GlnGlnTrpGluGlyArgGlnValLeuTyrGlnGln           57

AGCAGCGGGCACAACAACCGCGCCCTGGTGTCCTAC          468
SerSerGlyHisAsnAsnArgAlaLeuValSerTyr           69

GATGGTCTCAACCAGCGCGTGCGGGTGCTGGACGAG          504
AspGlyLeuAsnGlnArgValArgValLeuAspGlu           81

AGGAAAGCGCTGATCCCCTGCAAGAGATTATTTGAA          540
ArgLysAlaLeuIleProCysLysArgLeuPheGlu           93

TACATTTTACTCTATAAGGAGGGAGTGATGTTTCAG          576
TyrIleLeuLeuTyrLysGluGlyValMetPheGln          105
```

Fig. 3 (B)

```
ATTGAACAAGCCACCAAACAGTGTGCAAAGATCCCC   612
IleGluGlnAlaThrLysGlnCysAlaLysIlePro   117

TTGGTGGAATCCTGGGATCCTCTGGACATTCCCAG    648
LeuValGluSerTrpAspProLeuAspIleProGln   129

AATTCTACCTTTGAAGATCAGTACTCCATCGGAGGG   684
AsnSerThrPheGluAspGlnTyrSerIleGlyGly   141

CCTCAGGAGCAGATCCTGGTCCAGGAGTGGTCTGAC   720
ProGlnGluGlnIleLeuValGlnGluTrpSerAsp   153

AGAAGAACAGCAAGATCCTATGAAACTTGGATCGGC   756
ArgArgThrAlaArgSerTyrGluThrTrpIleGly   165

GTTTATACAGCCAAGGATTGTTATCCGGTCCAGGAG   792
ValTyrThrAlaLysAspCysTyrProValGlnGlu   177

ACCTTCATCAGGAACTACACTGTGGTCATGTCCACG   828
ThrPheIleArgAsnTyrThrValValMetSerThr   189

CGGTTCTTTGATGTGCAGCTAGGCATTAAGGACCCC   864
ArgPhePheAspValGlnLeuGlyIleLysAspPro   201

TCTGTGTTCACCCCACCAAGCACATGCCAGGCAGCG   900
SerValPheThrProProSerThrCysGlnAlaAla   213

CAGCCAGAGAAGATGAGTGACGGCTGCTCCTTGTGA   936
GlnProGluLysMetSerAspGlyCysSerLeu***  224

ACTCGCCGAACTGAACCCAACCTCAGCTCTTAGTGA   972
CCTTGTATGGCAATGGATTAGAGACTAGTTTGAAAG  1008
TAACTCTTCACTGAAAATAAAGCTAATTTTAGGAAG  1044
ATAAACCCTATGTGGGCTTGCTTGTACATCTGACTG  1080
TGGCTGCTCAGCTCTGTTTTGAGAAGGAAAGGGGCC  1116
ATCCTTTCTGTGAGCAGGTGGGTAGTCAGTGCCATA  1152
```

Fig. 3 (C)

```
GAGTAGGAAAGGGCGGGGGTGGGGTCAGCACAAGGA 1188
GTTTGCCTCTGCAGGGTGAGACTTTTATTATTGCCA 1224
ATAAGAATCGAAGGTGATAATAAGATATAGAATGCT 1260
TTTGTTCAGTTCTCCCCTTACAAAGAAAGTCCCTTG 1296
CTTGTCTGCACCAGGGAAGCAAGAGCTCCCAGTGAC 1332
ACCACCCCCTGCCTCTGGTTACTATAAGATGAGCCT 1368
TTAAGATTCTTTCTAGACTTAAATTTTGTGCCATGG 1404
CCCACTGGATGTAGATATTCTACAAGGAAGTAGAAA 1440
CTTTTAATACGAAGTAATGATTCCTCTAAAGGGAAA 1476
GGAAGTTTTAAGAGGGAGGCTTGGACAATCTTAGTA 1512
TTTACACGTGAGATGAAATGAAGAGTCCCGTGTGCT 1548
GCTCTGTGTGCAAGAGTACTGACCGCTCTGCTGAAC 1584
CTTCATGTCTTTTCTAGTGGGCAACCAGGCTTCCAA 1620
AATAGCACTGACCTGGGAGGCCCCAAGTAAGGCCA 1656
AGAAGTCTCTGCTACTCTAATCTTTTACGTATTAAA 1692
TGCACTAGGCTAGTAGCCCTTGCCTTTCCTTTCCTG 1728
AAACTCTTTCAACACAACTGTGTCTATATGACTACG 1764
GCTCATGCTTCCAAGGTCAGCTCACATGTGACCTCT 1800
GTGAGCTGTTCCCTCGCCTGAATTCATTGCATCTTA 1836
CACCTTGGCATGCCTTGCTCACAATACTCATTATGC 1872
TGTGTGGATTTCCTGATTACTAGAAGCTGACCTCT 1908
GCTATCCTGGGTAAGAACGCCCTGAGTACGGGTACC 1944
ATGCTCTGTTTACTTTAGGATCTCCAGCACCAAGCA 1980
AGTGCCTGGCACATAGTCTGTGCCCTTAACATTTGT 2016
AGAAAGGAGCTCACCAGCTCTGTCAGTGTTTAGTTT 2052
CTTCATCTATTAAACAGGGTTGGTTTTTCTGGTTGC 2088
TAGGGAGACTTATAGTAATACAACTTACTATTCTAG 2124
ATTCTTCTTATCGCTGTGTTTATTTGCCATGTATC 2160
ATCTTTTGTTATCAAGAGAAGTGTATGATGCTTGCT 2196
TTATGCCATAGCCATCTATATTGTAATTTATCTATA 2232
CAATTAAACAAATTTAATGAACCCTATGAATTATTC 2268
TTTGATGTGTTTGTTTTTGTAAGAAATATGGAGGAA 2304
CTGAATTATAAAGAAAATAAAATCCTTCTGTAATAA 2340
```

Fig. 3 (D)

```
TCAAATAAAGTACTTCCCATAATCAAAACCAAAAAA 2376
AAAAAAAAAAAAAAAAAAAAAAAAAAA          2403
```

10              20              30              40              50
(1)    1  MPGRAPLRTV  PGALGAWLLG  GLWAWTLCGL  CSLGAVGAPR  PCQAPQQWEG
(2)    1  MLTRAPRRLV  QGPRETWLLG  GLWVWLLCGL  GMAGSPGTPQ  PCQAPQQWEG
(3)    1  MPARAPRRLV  QGPRGTWLLG  SLWVWVLCGL  GMAGSLGTPQ  PCQAPQQWEG 60              70              80              90              100
(1)   51  RQVMYQQSSG  RNSRALLSYD  GLNQRVRVLD  ERKALIPCKR  LFEYILLYKD
(2)   51  RQVLYQQSSG  HNSRALVSYD  GLNQRVRVLD  ERKALIPCKR  LFEYILLYKD
(3)   51  RQVLYQQSSG  HNNRALVSYD  GLNQRVRVLD  ERKALIPCKR  LFEYILLYKE 110             120             130             140             150
(1)  101  GVMFQIDQAT  KQCSKMTLTQ  PWDPLDIPQN  STFEDQYSIG  GPQEQITVQE
(2)  101  GVMFQIEQAT  KLCAKIPLAE  PWDPLDIPQN  STFEDQYSIG  GPQEQIMVQE
(3)  101  GVMFQIEQAT  KQCAKIPLVE  SWDPLDIPQN  STFEDQYSIG  GPQEQILVQE 160             170             180             190             200
(1)  151  WSDRKSARSY  ETWIGIYIVK  DCYPVQETFI  INYSVILSTR  FFDIQLGIKD
(2)  151  WSDRRTARSY  ETWIGVYTAK  DCYPVQETFI  RNYIVLSTR   FFDVQLGIKD
(3)  151  WSDRRTARSY  ETWIGVYTAK  DCYPVQETFI  RNYIVVMSTR  FFDVQLGIKD 210             220             230             240             250
(1)  201  PSVFTPPSTG  QMAQLEKMSE  DCSW*       .........   .........
(2)  201  PSVFTPPSTG  QTAQPEKMKE  NCSL*       .........   .........
(3)  201  PSVFTPPSTG  QAAQPEKMSD  GCSL*       .........   .........
```

Fig. 5

```
(1)   1  MPGRAPLRTV PGALGAWLLG GLNWAWTEGL CSLGAVGAPR PCQAPQQWEG   50
(2)   1  MLTRAPRRLV QGPRETWLLG GLWVWLCGL  GMAGSPGTPQ PCQAPQQWEG   50

(1)  51  RQVMYQQSSG RNSRALLSYD GLNQRVRVLD ERKALIPCKR LFEYILLYKD  100
(2)  51  RQVLYQQSSG HNSRALVSYD GLNQRVRVLD ERKALIPCKR LFEYLFFYKD  100

(1) 101  GVMFQDDQAT KQGSKMTETQ PWDPEDLPQN STFEDQYSIG GPQEQITVQE  150
(2) 101  GVMFQDEQAD KLGAKIPLAE PWDPEDIPQN STFEDQYSIG GPQEQIMVQE  150

(1) 151  WSDRKSARSY ETWIGIYIVK DCYPVQETFT INYSVLESTR FEDIQLGIKD  200
(2) 151  WSDRRTARSY ETWIGVYTAK DCYPVQETFI RNYTVLESTR FEDVQLGIKD  200

(1) 201  PSVETPPSIG QMAQLEKMSE QMAQLEKMSE DCSW*                   250
(2) 201  PSVETPPSIG QTAQPEKMKE                NCSL*
```

HUMAN EPENDYMIN-LIKE PROTEIN

This Application is the National Stage of International Application Serial No. PCT/JP97/03194, filed Sep. 10, 1997.

TECHNICAL FIELD

The present invention relates to a novel, protein showing a physiological activity on the central nervous system such as nerve-extending activity, neuroregenerative activity, gliacyte (glial cells) stimulating activity and so on.

BACKGROUND ART

The engram or trace of memory in the brain can be divided into two phases, namely acquisition of a short-term memory and fixation of a long-term memory. It is known that electroshocks and anesthesia may destroy the short-term memory but have no effect on the long-term memory once established. On the other hand, it is known that the biochemical reactions and structural changes leading to formation of a long-term memory as the antithesis of a short-term memory can be blocked by means of protein synthesis inhibitors such as puromycin and cycloheximide (Flexner, J. B. et al., Science, 141, 57–59 (1963); Agranoff, B. W. and Klinger, P. D., Science, 146, 952–953 (1964); Agranoff, B. W. et al., Brain Research 1, 300–309 (1966)). Therefore, it has been suspected over the past twenty years that certain protein metabolisms including de novo synthesis of proteins are involved in the formation of long-term memories in the brain. However, few proteins have been identified to this day which show an increased metabolic turnover following acquisition of a new behavior (Hyden, H and Lange, P. W., Proceedings of the National Academy of Sciences of the U.S.A., 65, 898–904 (1970); Shashoua, V. E., Science, 193, 1264–1266 (1976)).

Ependymin, among such proteins, was first reported as an entity comprising two kinds of proteins whose expression was increased after learning in the brain of goldfish as assayed by a double-labeling technique using [$^3$H]valine and [$^{14}$C]valine (Shashoua, V. E., Science, 193, 1264–1266 (1976)). Early immunohistological distribution studies (Shashoua, V. E., Brain Research, 122, 113–124 (1977), Benowitz, L. I. and Shashoua, V. E., Brain Research, 136, 227–242 (1977)) revealed that those proteins occurred in high concentrations in the ependymal zone (the cellular membrane lining the brain ventricles) and accordingly they were named ependymin β and ependymin γ, respectively. However, it was subsequently suggested that those proteins were secretory proteins which were secreted into the cerebrospinal fluid (Shashoua, V. E. Brain Research, 166, 349–358 (1979); Shashoua, V. E. Neurochem. Res., 6, 1129–1147 (1981)) and more detailed immunohistological investigation endorsed the suggestion by the detection of ependymin in high concentrations in the mesencephalic structures and cerebrospinal fluid (Schmidt, R. and Lapp, H., Neurochem. Int., 10, 383–390 (1987).

Ependymin β and ependymin γ were initially considered to be mutually distinct proteins because they gave molecular masses of 35 kDa and 30 kDa, respectively, on SDS-PAGE but it was later discovered that they are proteins identical in amino acid sequence and only dissimilar in sugar chain content (Schmidt, R. and Shashoua, V. E., Journal of Neurochemistry, 40, 652–660, (1983)). Moreover, it was reported that those proteins formed dimers and have a sugar chain content of at least 5% (Shashoua, V. E., Cell. Mol. Neurobiol., 5, 183–207 (1985)).

Based on the above series of research findings, ependymin had come to be considered to be associated with the learning and memory processes. For example, when an anti-ependymin antibody was injected into the cerebral ventricles, the integration of memories was blocked (Shashoua, V. E., Proceedings of the National Academy of Sciences of the U.S.A., 74, 1743–1747 (1977); Shashoua, V. E. and Moore, M. E. Brain Research, 148, 441–449 (1978); Schmidt, R. Adv. Biosci., 59, 213–222 (1986); Piront, M. L. and Schmidt, R., Brain Research, 442, 53–62 (1988)) and also in conditional experiments, the amount of expression of ependymin and its concentration had significant influences on the test results (Schmidt, R., Journal of Neurochemistry, 48, 1870–1878, (1987); Shashoua, V. E. and Hesse, G. W. Brain Research, 484, 333–339 (1989); Schmidt, R. et al., Progress in Brain Research, 91, 7–12 (1992)). Recently it has been discovered that ependymin is involved in the regeneration of the optic nerve of goldfish (Thormodsson, F. R. et al., Society Neuroscience Abstract, 14, 805 (1988)). It has also been found that ependymin is synthesized in the process of optic nerve regeneration (Schmidt, J. T. and Shashoua, V. E., Brain Research, 446, 269–284 (1988); Thormodsson, F. R. et al., Experimental Neurology, 118, 275–283 (1992)). This protein has, therefore, come to be a focus of attention. In the most recent researches using immunoelectron microscopic and in situ hybridization techniques, it was found that the mRNAs were expressed to synthesize the proteins, in reticulofibroblast cells of the inner endomeningeal cell layer but are not expressed in neurons and glial cells. However, after learning, the proteins are found in nerve cells and glial cells where the mRNAs are not detected, suggesting that the takeup of those proteins from the meninx by the neurons and glicytes has a functional importance in the plastic adaptations of the central nervous system (Rother, S. et al. Journal of Neurochemistry, 65, 1456–1464 (1995); Schmidt, R. et al., Journal of Neurochemistry, 65, 1465–1471 (1995)).

However, those studies were invariably undertaken in fish such as goldfish and the cDNA of ependymin has been found only in fish such as zebrafish, salmon, rainbow trout, herring, and carp in addition to goldfish (Koenigstorfer, A. et al., Journal of Neurochemistry, 52, 310–312 (1989); Koenigstorfer, A., Journal of Biological Chemistry, 264, 13689–13692 (1989); Sterrer, S. et al., Neuroscience, 37, 277–284 (1990); Muller-Schmid, A. et al., Gene, 118, 189–196 (1992); Muller-Schmid, A. et al., Journal of Molecular Evolution, 36, 578–585 (1993)). Meanwhile, it has been suspected that some protein corresponding to this ependymin exists in mammals as well, and including the report that an ependymins-like immune reaction is found in rat hippocampal neurons (Schmidt, R. et al., Brain Research, 386, 245–257 (1986)), a large number of immunohistological studies have been reported (Fazei, M. S. et al., European Journal of Neuroscience, Suppl. 1, 90 (1988); Shashoua, V. E. et al., Brain Research, 522, 181–190 (1990); Shashoua, V. E. et al., Journal of Neuroscience Research, 32, 239–244 (1992)). However, it remains to be established, biochemically or molecular biologically, whether there actually exists a mammalian counterpart of ependymin.

As the result of intensive research, the inventors of the present invention succeeded in cloning a cDNA having a novel nucleotide sequence from human placenta-, rat brain- or mouse spinal cord derived cDNA library and found that the protein encoded thereby is an ependymin-like protein having a physiological activity such as nerve-extending activity or neuroregenerative activity on the central nervous system, or gliacyte stimulating activity. As a result of continued investigations based on such findings, the present inventors have now completed the present invention.

DISCLOSURE OF INVENTION

The present invention provides:

(1) An ependymin-like protein derived from a mammal, or a salt thereof;

(2) A protein comprising an amino acid sequence represented by SEQ ID NO:1, SEQ ID NO:2 or SEQ ID NO:3, or a substantial equivalent thereto, or a salt thereof;

(3) The protein according to (2), wherein the substantially equivalent amino acid sequence to the amino acid sequence represented by SEQ ID NO:1, SEQ ID NO:2 or SEQ ID NO:3 is an amino acid sequence comprising an amino acid sequence represented by SEQ ID NO:4, SEQ ID NO:5, SEQ ID NO:6 or SEQ ID NO:7;

(4) The protein according to (2), wherein the substantially equivalent amino acid sequence to the amino acid sequence represented by SEQ ID NO:1, SEQ ID NO:2 or SEQ ID NO:3 is an amino acid sequence having an identity of not less than about 95% to the amino acid sequence represented by SEQ ID NO:1, SEQ ID NO:2 or SEQ ID NO:3;

(5) The protein according to (2), wherein the substantially equivalent amino acid sequence to the amino acid sequence represented by SEQ ID NO:1, SEQ ID NO:2 or SEQ ID NO:3 is (i) an amino acid sequence wherein one or more amino acid residues are deleted from the amino acid sequence represented by SEQ ID NO:1, SEQ ID NO:2 or SEQ ID NO:3, (ii) an amino acid sequence wherein one or more amino acid residues are added to the amino acid sequence represented by SEQ ID NO:1, SEQ ID NO:2 or SEQ ID NO:3, (iii) an amino acid sequence wherein one or more amino acid residues in the amino acid sequence represented by SEQ ID NO:1, SEQ ID NO:2 or SEQ ID NO:3 are substituted with one or more amino acid residues, or (iv) a combination thereof;

(6) The protein according to (2), which has a nerve-extending activity;

(7) A partial peptide of the protein according to (1) or (2), or a salt thereof;

(8) The partial peptide according to (7), which has an amino acid sequence represented by any one of SEQ ID NO:4 to SEQ ID NO:9;

(9) A precursor protein of the protein according to (2) or a salt thereof, which comprises an amino acid sequence represented by SEQ ID NO:10, SEQ ID NO:11, SEQ ID NO:12 or SEQ ID NO:13, or a substantial equivalent thereto;

(10) A signal peptide comprising an amino acid sequence represented by SEQ ID NO:14, SEQ ID NO:15, SEQ ID NO:16 or SEQ ID NO:17, or a substantial equivalent thereto;

(11) A DNA which comprises a DNA having a nucleotide sequence coding for the protein according to (1) or (2);

(12) The DNA according to (11), which comprises a nucleotide sequence represented by SEQ ID NO:18, SEQ ID NO:19 or SEQ ID NO:20;

(13) A DNA which comprises a DNA having a nucleotide sequence coding for the precursor protein according to (9);

(14) The DNA according to (13), which comprises a nucleotide sequence represented by SEQ ID NO:27, SEQ ID NO:28, SEQ ID NO:29 or SEQ ID NO:30;

(15) A DNA which comprises a DNA having a nucleotide sequence coding for the signal peptide according to (10);

(16) The DNA according to (15), which comprises a nucleotide sequence represented by SEQ ID NO:31, SEQ ID NO:32, SEQ ID NO:33 or SEQ ID NO:34;

(17) A recombinant vector comprising the DNA according to (11);

(18) A transformant which is transformed with the recombinant vector according to (17);

(19) A method for producing the protein according to (1) or (2) or a salt thereof, which comprises cultivating the transformant according to (18) under conditions suitable to express and accumulate the protein according to (1) or (2) or a salt thereof, and collecting the same;

(20) A pharmaceutical composition which comprises the protein according to (1) or (2), the partial peptide according to (7), or a salt thereof;

(21) The pharmaceutical composition according to (20), which is a therapeutic or prophylactic agent for Alzheimer's disease, Parkinson's disease, Huntington's disease, amyotrophic lateral sclerosis, dementia or cerebellar degeneration;

(22) A pharmaceutical composition which comprises the DNA according to (11);

(23) The pharmaceutical composition according to (22), which is a therapeutic or prophylactic agent for Alzheimer's disease, Parkinson's disease, Huntington's disease, amyotrophic lateral sclerosis, dementia or cerebellar degeneration;

(24) An antibody against the protein according to (1) or (2), the partial peptide according to (7), the precursor protein according to (9), or a salt thereof;

(25) A method for quantitative determination of the protein according to (1) or (2), the partial peptide according to (7), the precursor protein according to (9), or a salt thereof, which comprises contacting the antibody according to (24) with the protein according to (1) or (2), the partial peptide according to (7), the precursor protein according to (9), or a salt thereof;

(26) A method for quantitative determination of the protein according to (1) or (2), the partial peptide according to (7), the precursor protein according to (9), or a salt thereof in a test liquid sample, which comprises
  (a) competitively reacting the test liquid sample and a labeled protein according to (1) or (2), the partial peptide according to (7), the precursor protein according to (9), or a salt thereof with the antibody according to (24), and
  (b) measuring the ratio of the labeled protein according to (1) or (2), the partial peptide according to (7), the precursor protein according to (9), or a salt thereof which binds to the antibody;

(27) A method for quantitative determination of the protein according to (1) or (2), the partial peptide according to (7), the precursor protein according to (9), or a salt thereof in a test liquid sample, which comprises
  (a) reacting the test liquid sample with the antibody according to (24) immobilized on an insoluble carrier and another labeled antibody according to (24) simultaneously or continuously, and
  (b) measuring the activity of labeling agent on the insoluble carrier;

(28) A method for screening for a compound which promotes a function of the protein according to (1) or (2), the partial protein according to (7), or a salt thereof, which comprises measuring and comparing the function of the protein according to (1) or (2), the partial protein according to (7) or a salt thereof, in cases that (i) the protein according to (1) or (2), the partial protein according to (7) or a salt thereof is contacted with a nerve cell or a nerve tissue and (ii) the protein according to (1) or (2), the partial protein according to (7) or a salt thereof and a test compound are contacted with a nerve cell or a nerve tissue;

(29) The method according to (28), wherein the function is (i) a nerve-extending activity in the central nerve system or glia cell stimulating activity or (ii) an activity of forming memories in the brain;

(30) The method according to (28), wherein the function is a nerve-extending activity;

(31) A kit for screening for a compound which promotes a function of the protein according to (1) or (2), the partial protein according to (7) or a salt thereof, which comprises the protein according to (1) or (2), the partial peptide according to (7) or a salt thereof;

(32) A compound, or a salt thereof, which promotes a function of the protein according to (1) or (2), the partial peptide according to (7) or a salt thereof, and which is obtained by the method for screening according to (28) or the kit for screening according to (31);

(33) A pharmaceutical composition which comprises the compound, or a salt thereof, which promotes a function of the protein according to (1) or (2), the partial peptide according to (7) or a salt thereof, and which is obtained by the method for screening according to (28) or the kit for screening according to (31);

(34) The pharmaceutical composition according to (33), which is a therapeutic or prophylactic agent for Alzheimer's disease, Parkinson's disease, Huntington's disease, amyotrophic lateral sclerosis, dementia or cerebellar degeneration;

(35) A method for treating or preventing Alzheimer's disease, Parkinson's disease, Huntington's disease, amyotrophic lateral sclerosis, dementia or cerebellar degeneration in a mammal which comprises administering an effective amount of the protein according to (1) or (2), the partial peptide according to (7) or a salt thereof to said mammal;

(36) A method for treating or preventing Alzheimer's disease, Parkinson's disease, Huntington's disease, amyotrophic lateral sclerosis, dementia or cerebellar degeneration in a mammal which comprises administering an effective amount of the DNA according to (11) or a salt thereof to said mammal;

(37) Use of the protein according to (1) or (2), the partial peptide according to (7) or a salt thereof for production of a therapeutic or prophylactic agent for Alzheimer's disease, Parkinson's disease, Huntington's disease, amyotrophic lateral sclerosis, dementia or cerebellar degeneration; and

(38) Use of the DNA according to (11) for production of a therapeutic or prophylactic agent for Alzheimer's disease, Parkinson's disease, Huntington's disease, amyotrophic lateral sclerosis, dementia or cerebellar degeneration.

The present invention, furthermore, provides:

(39) A DNA comprising a DNA having a nucleotide sequence capable of hybridizing under a high stringent condition with the nucleotide sequence of SEQ ID NO:18, SEQ ID NO:19 or SEQ ID NO:20;

(40) A recombinant vector comprising the DNA according to (39);

(41) A transformant which is transformed with the recombinant vector according to (40);

(42) A method for producing the protein encoding by the DNA according to (39) or a salt thereof, which comprises cultivating the transformant according to (41) under conditions suitable to express and. accumulate the protein, and collecting the same;

(43) A protein encoded by the DNA according to (42), or a salt thereof, which is produced by the method according to (42);

(44) A DNA comprising a DNA having a nucleotide sequence coding for the partial peptide according to (7);

(45) The DNA according to (44), which comprises a nucleotide sequence represented by any one of SEQ ID NO:21 to SEQ ID NO:26;

(46) A recombinant vector comprising the DNA according to (45);

(47) A transformant which is transformed with the recombinant vector according to (46);

(48) A method for producing the partial peptide or a salt thereof according to (7), which comprises cultivating the transformant according to (47) under conditions suitable to express and accumulate the partial peptide, and collecting the same;

(49) An oligonucleotide or a derivative thereof which has a nucleotide sequence complementary or substantially complementary to the DNA according to (11) or (39) and capable of promoting an expression of the DNA;

(50) The oligonucleotide or derivative according to (49), wherein the nucleotide sequence substantially complementary to the DNA according to (11) or (39) is a nucleotide sequence having an identity of not less than about 60% (preferably not less than about 70%, more preferably not less than about 80%, still, more preferably not less than about 90%, most preferable not less than about 95%) to the total nucleotide sequence or a part of the nucleotide sequence of the nucleotide sequence complementary to the DNA according to (11) or (39);

(51) A pharmaceutical composition which comprises the oligonucleotide or derivative according to (49);

(52) The pharmaceutical composition according to (51), which is a therapeutic or prophylactic agent for Alzheimer's disease, Parkinson's disease, Huntington's disease, amyotrophic lateral sclerosis, dementia or cerebellar degeneration;

(53) The protein according to (1) or (2), which has (i) an amino acid sequence represented by SEQ ID NO:1, (ii) an amino acid sequence represented by SEQ ID NO:2, (iii) an amino acid sequence wherein Gly is added to the N-terminus of the amino acid sequence represented by SEQ ID NO:2, (iv) an amino acid sequence represented by SEQ ID NO:3 or (v) an amino acid sequence wherein 7 amino acid residues of the C-terminus of the amino acid sequence represented by SEQ ID NO:17 are added to the N-terminus of the amino acid sequence represented by SEQ ID NO:3;

(54) The signal peptide according to (9), which has (i) an amino acid sequence represented by SEQ ID NO:14, (ii) an amino acid sequence represented by SEQ ID NO:15, (iii) an amino acid sequence represented by SEQ ID NO:16, (iv) an amino acid sequence wherein Gly is deleted from the C-terminus of the amino acid sequence represented by SEQ ID NO:16, (v) an amino acid sequence represented by SEQ ID NO:17 or (vi) an amino acid sequence wherein 7 amino acid residues are deleted from the C-terminus of the amino acid sequence represented by SEQ ID NO:17;

(55) A DNA coding for the protein according to (53), which is (i) a DNA having a nucleotide sequence represented by SEQ ID NO:18, (ii) a DNA having a nucleotide sequence represented by SEQ ID NO:19, (iii) a DNA having a nucleotide sequence wherein GGC are added to 5'-terminus of the nucleotide sequence represented by SEQ ID NO:19, (iv) a DNA having a nucleotide sequence represented by SEQ ID NO:20 or (v) a DNA having a nucleotide sequence wherein 21 bases of the 3'-terminus of the nucleotide sequence represented by SEQ ID NO:34 are added to the 5'-terminus of the nucleotide sequence represented by SEQ ID NO:20; and

(56) A DNA coding for the signal peptide according to (54), which is (i) a DNA having a nucleotide sequence represented by SEQ ID NO:31, (ii) a DNA having a nucleotide sequence represented by SEQ ID NO:32, (iii) a DNA having a nucleotide sequence represented by SEQ ID NO:33, (iv) a DNA having a nucleotide sequence wherein GGC are deleted from the 3'-terminus of the nucleotide sequence represented by SEQ ID NO:33, (v) a DNA having a nucleotide sequence represented by SEQ ID NO:34 or (vi) a DNA having a nucleotide sequence wherein 21 bases are deleted from the 3'-terminus of the nucleotide sequence represented by SEQ ID NO:34.

The protein of the present invention includes an amino acid sequence represented by SEQ ID NO:1 (a 38th to 224th amino acid sequence of the amino acid sequence represented by SEQ ID NO:11 or FIG. 1), an amino acid sequence represented by SEQ ID NO:2 (a 35th to 224th amino acid sequence of the amino acid sequence represented by SEQ ID NO:12 or FIG. 2) or an amino acid sequence represented by SEQ ID NO:3 (a 38th to 224th amino acid sequence of the amino acid sequence represented by SEQ ID NO:13 or FIG. 3), or a substantial equivalent thereto.

The protein of the present invention may be a protein derived from any kind of cell (e.g. splenocytes, neurons, glia cells, splenic β cells, myelocytes, mesangial cells, Langerhan's cells, epidermal cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megarkaryocytes, synovial cells, chondrocytes, osteocytes, osteoblasts, osteoclasts, mammary cells, hepatocytes, interstitial cells, progenitor cells of said cells, stem cells, cancer cells, etc.) of mammals (e.g. human, guinea pig, rat, mouse, chicken, rabbit, swine, sheep, bovine, horse, monkey, etc.) or all tissues in which such cells are present, such as brain, various parts of brain (e.g. olfactory bulb, amygdaloid nucleus, cerebral basal nucleus, hippocampus, thalamus, hypothalamus, cerebral cortex, medulla oblongata, cerebellum), spinal cord, pituitary gland, stomach, spleen, kidney, liver, gonad, thyroid, gall-bladder, bone marrow, adrenal gland, skin, muscle, lung, gastrointestinal tract (e.g. large intestine, small intestine), blood vessels, heart, thymus, spleen, submandibular gland, peripheral blood, prostate, testis, ovary, placenta, uterus, bone, joint, skeletal muscle, etc., particularly brain or various parts of brain. It may be a protein derived from fishes such as goldfish, Zebrafish, salmon, trout, herring and carp, and furthermore, may be a synthetic protein as well.

Examples of the amino acid sequence which is substantially equivalent to the amino acid sequence represented by SEQ ID NO:1, SEQ ID NO:2 or SEQ ID NO:3 are an amino acid sequence which is not less than about 40%, preferably not less than about 60%, more preferably not less than about 70%, still more preferably not less than about 80%, furthermore preferably not less than about 90%, most preferably not less than about 95% identity to the amino acid sequence represented by SEQ ID NO:1, SEQ ID NO:2 or SEQ ID NO:3, and so on.

Preferable examples of the protein of the present invention which comprises an amino acid sequence substantially equivalent to the amino acid sequence represented by SEQ ID NO:1, SEQ ID NO:2 or SEQ ID NO:3 are a protein having an amino acid sequence substantially equivalent to the amino acid sequence represented by SEQ ID NO:1, SEQ ID NO:2 or SEQ ID NO:3 and having a substantially and qualitatively equivalent activity to the protein comprising the amino acid sequence represented by SEQ ID NO:1, SEQ ID NO:2 or SEQ ID NO:3, and so on.

Examples of the substantially and qualitatively equivalent activity are a nerve-extending activity or neuro-regenerative activity in the central nervous system, etc., a gliacyte stimulating activity, an activity of forming memories in brain, and so on.

The term "substantially and qualitatively equivalent activity" means that the nature of these activities are physiochemically or pharmacologically equivalent. The term "substantially and qualitatively equivalent" means that the nature of these activities is physiochemically or pharmacologically equivalent. Therefore, it is preferred that the potency of activities such as a nerve-extending activity, neuro-regenerative activity and a gliacyte stimulating activity is equivalent (e.g. about 0.01 to 100 times, preferably about 0.5 to 20 times, more preferably about 0.5 to 2 times), but it is allowable that even differences in the degree of these activities and the quantity such as molecular weight of the protein are present. These activities may be measured by per se known methods or an analogous method thereto.

And, other examples of the protein of the present invention are a protein having at least one amino acid sequence represented by SEQ ID NO:4, SEQ ID NO:5, SEQ ID NO:6 or SEQ ID NO:7 and having a substantially and qualitatively equivalent activity (e.g. nerve-extending activity or neuroregenerative activity in the central nervous system, etc., gliacyte stimulating activity, activity of formulating memories in brain) to the protein comprising the amino acid sequence represented by SEQ ID NO:1, SEQ ID NO:2 or SEQ ID NO:3, and so on.

The amino acid sequence represented by SEQ ID NO:4, SEQ ID NO:5, SEQ ID NO:6 or SEQ ID NO:7 is a common partial amino acid sequence (FIG. 4) of the amino acid sequence represented by SEQ ID NO:1, the amino acid sequence represented by SEQ ID NO:2 and the amino acid sequence represented by SEQ ID NO:3.

Furthermore, other examples of the protein of the present invention are a protein having at least one amino acid sequence represented by SEQ ID NO:4, SEQ ID NO:8, SEQ ID NO:9 or SEQ ID NO:7 and having a substantially and qualitatively equivalent activity (e.g. nerve-extending activity or neuro-regenerative activity in the central nervous system, etc., gliacyte stimulating activity, activity of forming memories in brain) to the protein comprising the amino acid sequence represented by SEQ ID NO:1, SEQ ID NO:2 or SEQ ID NO:3, and so on.

The amino acid sequence represented by SEQ ID NO:4, SEQ ID NO:8, SEQ ID NO:9 or SEQ ID NO:7 is a common partial amino acid sequence (FIG. 5) of the amino acid sequence represented by SEQ ID NO:1 and the amino acid sequence represented by SEQ ID NO:2.

And, the protein of the present invention includes, for example, proteins comprising (1) an amino acid sequence wherein one or more amino acid residues (for example about 1 to 20, preferably about 1 to 9, and more preferably a few (1 to 5) amino acid residues) are deleted from the amino acid sequence represented by SEQ ID NO:1, SEQ ID NO:2 or SEQ ID NO:3, (2) an amino acid sequence wherein one or more amino acid residues (for example about 1 to 20, preferably about 1 to 9, and more preferably a few (1 to 5) amino acid residues) are added to the amino acid sequence represented by SEQ ID NO:1, SEQ ID NO:2 or SEQ ID NO:3, (3) an amino acid sequence wherein one or more other amino acid residues in the amino acid sequence represented by SEQ ID NO:1, SEQ ID NO:2 or SEQ ID NO:3 are substituted with one or more amino acid residues (for example about 1 to 20, preferably about 1 to 9, and more preferably a few (1 to 5) amino acid residues), or (4) a combination thereof.

In the above-mentioned deletion, addition or substitution in the amino acid sequence represented by SEQ ID NO:1, SEQ ID NO:2 or SEQ ID NO:3, examples of the positions of deletion, addition or substitution are not so critical but are preferably positions other than common amino acid sequences between the amino acid sequence represented by SEQ ID NO:1, the amino acid sequence represented by SEQ ID NO:2 and the amino acid sequence represented by SEQ ID NO:3. More specifically, preferable examples of the positions of deletion, addition or substitution are positions other than the amino acid sequence represented by SEQ ID NO:4, SEQ ID NO:5, SEQ ID NO:6 or SEQ ID NO:7.

In the above-mentioned deletion, addition or substitution in the amino acid sequence represented by SEQ ID NO:1 or SEQ ID NO:2, examples of the positions of deletion, addition or substitution are not so critical but are preferably positions other than common amino acid sequences between the amino acid sequence represented by SEQ ID NO:1 and the amino acid sequence represented by SEQ ID NO:2. More specifically, preferable examples of the positions of deletion, addition or substitution are positions other than the amino acid sequence represented by SEQ ID NO:4, SEQ ID NO:8, SEQ ID NO:9 or SEQ ID NO:7.

Among the above-mentioned proteins, the protein which is derived from a mammal and has an ependymin-like activity (e.g. nerve-extending activity or neuro-regenerative activity in the central nervous system, gliacyte stimulating activity, activity of forming memories in brain) is preferred.

Throughout this specification, proteins are represented in accordance with the conventions for description of peptides, that is, the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO⁻) form at the C-terminus but may be in the amide (—CONH$_2$) or ester (—COOR) form.

R in the ester residue includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl which is commonly used for the production of esters for oral administration.

When the protein of the present invention has a carboxyl (or carboxylate) in any position other than the C-terminus, the corresponding amide or ester form is also included in the scope of the present invention. The ester mentioned just above may be any of the esters mentioned for the C-terminal carboxyl function.

Furthermore, the protein of the present invention includes (1) the protein in which the N-terminal amino acid residue is protected with a protective group (e.g. $C_{1-6}$ acyl such as $C_{1-6}$ alkanoyl such as formyl acetyl, etc.), (2) the protein in which the N-terminal side of Glu is cleaved in vivo to form pyroglutamic acid, (3) the protein in which the side chain of any relevant constituent amino acid (e.g. OH, SH, NH$_2$, imidazole group, indole group, guanizino group, etc.) is protected by a protective group (e.g. $C_{1-6}$ acyl group such as $C_{1-6}$ alkanoyl such as formyl or acetyl, etc.), (4) the protein in which the carboxyl group on the side chain of any relevant constituent amino acid in amidated (CONH$_2$) or esterified (—COOR), and (5) the complex protein such as glycoproteins available upon attachment of sugar chains.

More preferable examples of the protein of the present invention are (1) a human (more specifically, human placenta-derived) protein having the amino acid sequence represented by SEQ ID NO:1 (a 38th to 224th amino acid sequence of FIG. 1), (2) a rat (more specifically, rat brain-derived) protein having the amino acid sequence represented by SEQ ID NO:2 (a 35th to 224th amino acid sequence of FIG. 2), (3) a rat (more specifically, rat brain-derived) protein having the amino acid sequence wherein Gly is added to the N-terminus of the amino acid sequence represented by SEQ ID NO:2 (a 34th to 224th amino acid sequence of FIG. 2), (4) a mouse (more specifically, mouse spinal cord protein having the amino acid sequence represented by SEQ ID NO:3 (a 38th to 224th amino acid sequence of FIG. 3), (5) a mouse (more specifically, mouse spinal cord-derived) protein having the amino acid sequence (a 31st to 224th amino acid sequence of FIG. 3) wherein 7 amino acid residues of the C-terminus of the amino acid sequence represented by SEQ ID NO:17 are added to the N-terminus of the amino acid sequence represented by SEQ ID NO:3, and so on.

The partial peptide of the protein of the present invention may be any peptides of the above mentioned proteins of the present invention such as peptides comprising at least not less than about 10, preferably not less than about 50, more preferably not less than about 100 amino acid residues of the amino acid sequence of the proteins of the present invention, and preferably having activities such as a nerve-extending activity or neuro-regenerative activity in the central nervous system, etc., a gliacyte stimulating activity, an activity of forming memories and so on.

Specific examples of the partial peptide of the present invention are a peptide having (i) an amino acid sequence represented by SEQ ID NO:4 (a 41st to 53rd amino acid sequence of the amino acid sequence represented by any one of SEQ ID NO:11 to SEQ ID NO:13 or FIG. 4), (ii) an amino acid sequence represented by SEQ ID NO:5 (a 68th to 99th amino acid sequence of the amino acid sequence represented by any one of SEQ ID NO:1 to SEQ ID NO:13 or FIG. 4), (iii) an amino acid sequence represented by SEQ ID NO:6 (a 122nd to 146th amino acid sequence of the amino acid sequence represented by any one of SEQ ID NO:11 to SEQ ID NO:13 or FIG. 4) or (iv) an amino acid sequence represented by SEQ ID NO:7 (a 195th to 211st amino acid sequence of the amino acid sequence represented by any one of SEQ ID NO:11 to SEQ ID NO:3 or FIG. 4), and so on.

And, other specified examples of the partial peptide of the present invention are a peptide having (i) an amino acid sequence represented by SEQ ID NO:4 (a 41st to 53rd amino acid sequence of the amino acid sequence represented by SEQ ID NO:11, SEQ ID NO:12 or FIG. 5), (ii) an amino acid sequence represented by SEQ ID NO:8 (a 68th to 106th amino acid sequence of the amino acid sequence represented by SEQ ID NO:11, SEQ ID NO:12 or FIG. 5), (iii) an amino acid sequence represented by SEQ ID NO:9 (a 121st to 146th amino acid sequence of the amino acid sequence represented by SEQ ID NO:11, SEQ ID NO:12 or FIG. 5) or (iv) an amino acid sequence represented by SEQ ID NO:7 (a 195th to 211st amino acid sequence of the amino acid sequence represented by SEQ ID NO:11 or SEQ ID NO:12 or FIG. 5), and so on.

Furthermore, other preferable examples of the partial peptide of the present invention are a peptide having (i) a 41st to 106th amino acid sequence, (ii) a 121st to 179th amino acid sequence or (iii) a 187th to 211st amino acid sequence of the amino acid sequence represented by any one of SEQ ID NO:11 to SEQ ID NO:13 or FIG. 5, and so on.

The partial peptide of the present invention may include peptides such as a peptide comprising (1) an amino acid sequence wherein one or more amino acid residues (for example about 1 to 10, preferably a few (1 to 5) amino acid residues) are deleted from the amino acid sequence as mentioned above, (2) an amino acid sequence wherein one or more amino acid residues (for example about 1 to 10, preferably a few (1 to 5) amino acid residues) are added to the amino acid sequence as mentioned above, (3) an amino acid sequence wherein one or more amino acid residues (for example about 1 to 10, preferably a few (1 to 5) amino acid residues) in the amino acid sequence represented as mentioned above are substituted with other amino acid residues, or (4) a combination thereof.

The peptide of the present invention is usually in the carboxyl (—COOH) or carboxylate (—COO⁻) form at the C-terminus, but may instead be in the amide (—CONH$_2$) or ester (—COOR) form in the same manner as the protein of the present invention as mentioned above.

Furthermore, the partial peptide of the present invention includes (1) a peptide in which the N-terminal amino acid residue (e.g. Met) is protected with a protective group, (2) a peptide in which the N-terminal side of Glu is cleaved in vivo to form pyroglutamic acid, (3) a peptide in which the side chain of any relevant constituent amino acid is protected by any protective group, (4) a peptide in which the carboxyl group of the side chain of any relevant constituent amino acid is amidated (—CONH$_2$) or esterified (—COOR), and (5) a complex peptide such as glycoproteins available upon attachment of sugar chains in the same manner as the protein of the present invention as mentioned above.

As the partial peptide of the present invention is used as an antigen for preparation of an antibody, it does not need to have a nerve-extending activity or neuro-regenerative activity in the central nervous system, etc., a gliacyte stimulating activity or an activity of forming memories in brain.

The protein of the present invention may be a precursor protein. The precursor protein of the present invention is, for example, a protein in which one or more than 2, preferably about 1 to 200, more preferably about 1 to 100 amino acid residues bind to the N-terminus or(and) C-terminus of the protein of the present invention as mentioned above.

Specifically, the precursor protein of the present invention includes a protein having (i) an amino acid sequence represented by SEQ ID NO:10 (a 25th to 224th amino acid sequence of FIG. 1), (ii) an amino acid sequence represented by SEQ ID NO:11 (a 1st to 224th amino acid sequence of FIG. 1), (iii) an amino acid sequence represented by SEQ ID NO:12 (a 1st to 224th amino acid sequence of FIG. 2) or (iv) an amino acid sequence represented by SEQ ID NO:13 (a 1st to 224th amino acid sequence of FIG. 3) or (v) a substantial equivalent thereto, and so on.

The precursor protein of the present invention may be a protein derived from the above-mentioned cells of mammals or all tissues in which such cells are present, or may be a protein derived from fishes such as goldfish, zebrafish, salmon, trout, herring and carp, or may be a synthetic protein.

Examples of the substantially equivalent amino acid sequence to the amino acid sequence represented by SEQ ID NO:10 are an amino acid sequence having an identity of not less than about 40%, preferably not less than about 600%, more preferably not less than about 70%, furthermore preferably about 80%, still more preferably not less than about 90%, most preferably not less than about 95% to the amino acid sequence represented by SEQ ID NO:10, and so on.

The precursor proteins comprising the substantially equivalent amino acid sequence to the amino acid sequence represented by SEQ ID NO:10 include any proteins having a substantially equivalent amino acid sequence to the amino acid sequence represented by SEQ ID NO:10 and capable of yielding the protein of the present invention as mentioned above. Therefore, it is allowable that even differences among molecular weight, etc. are present.

Examples of the substantially equivalent amino acid sequence to the amino acid sequence represented by SEQ ID NO:11 are an amino acid sequence having an identity of not less than about 40%, preferably not less than about 60%, more preferably not less than about 70%, furthermore preferably about 80%, still more preferably not less than about 90%, most preferably not less than about 95% to the amino acid sequence represented by SEQ ID NO:11, and so on.

The precursor proteins comprising the substantially equivalent amino acid sequence to the amino acid sequence represented by SEQ ID NO:11 include any proteins having a substantially equivalent amino acid sequence to the amino acid sequence represented by SEQ ID NO:11 and capable of yielding the protein of the present invention as mentioned above. Therefore, it is allowable that even differences among molecular weight, etc. are present.

Examples of the substantially equivalent amino acid sequence to the amino acid sequence represented by SEQ ID NO:12 are an amino acid sequence having an identity of not less than about 40%, preferably not less than about 60%, more preferably not less than about 70%, furthermore preferably about 80%, still more preferably not less than about 90%, most preferably not less than about 95% to the amino acid sequence represented by SEQ ID NO:12, and so on.

The precursor proteins comprising the substantially equivalent amino acid sequence to the amino acid sequence represented by SEQ ID NO:12 include any proteins having a substantially equivalent amino acid sequence to the amino acid sequence represented by SEQ ID NO:12 and capable of yielding the protein of the present invention as mentioned above. Therefore, it is allowable that even differences among molecular weight, etc. are present.

Examples of the substantially equivalent amino acid sequence to the amino acid sequence represented by SEQ ID NO:13 are an amino acid sequence having an identity of not less than about 40%, preferably not less than about 60%, more preferably not less than about 70%, furthermore preferably about 80%, still more preferably not less than about 90%, most preferably not less than about 95% to the amino acid sequence represented by SEQ ID NO:13, and so on.

The precursor proteins comprising the substantially equivalent amino acid sequence to the amino acid sequence represented by SEQ ID NO:13 include any proteins having a substantially equivalent amino acid sequence to the amino acid sequence represented by SEQ ID NO:13 and capable of yielding the protein of the present invention as mentioned above. Therefore, it is allowable that even differences among molecular weight, etc. are present.

And, the precursor proteins of the present invention may include a protein comprising (i) an amino acid sequence wherein one or more amino acid residues (e.g. about 1 to 20, preferably about 1 to 9, more preferably a few (e.g. 1 to 5) amino acid residues) are deleted from the amino acid sequence represented by any one of SEQ ID NO:10 to SEQ ID NO:13, (ii) an amino acid sequence wherein one or more amino acid residues (e.g. about 1 to 20, preferably about 1 to 9, more preferably a few (e.g. 1 to 5) amino acid residues) are added to the amino acid sequence represented by any one of SEQ ID NO:10 to SEQ ID NO:13, (iii) an amino acid sequence wherein one or more amino acid residues (e.g. about 1 to 20, preferably about 1 to 9, more preferably a few (e.g. 1 to 5) amino acid residues) in the amino acid sequence represented by any one of SEQ ID NO:10 to SEQ ID NO:13 are substituted with one or more amino acid residues, or (iv) a combination thereof, and so on.

The precursor proteins of the present invention usually in the carboxyl (—COOH) or carboxylate (—COO⁻) form at C-terminus, but may instead be in the amide (—CONH$_2$) or ester (—COOR) form in the same manner as the protein of the present invention as mentioned above.

Furthermore, the precursor protein of the present invention includes (1) a protein in which the N-terminal amino acid residue (e.g. Met) is protected with a protective group, (2) a protein in which the N-terminal side Glu is cleaved in vivo to form pyroglutamic acid, (3) a protein in which the side chain of any relevant constituent amino acid has been protected by any protective group, (4) a peptide in which the carboxyl group of the side chain of any relevant constituent amino acid is amidated (—CONH$_2$) or esterified (—COOR), and (5) a complex protein such as glycoproteins available upon attachment of sugar chains in the same manner as the protein of the present invention as mentioned above.

The specific examples of the precursor proteins are (i) a protein in which the signal peptide of the present invention having an amino acid sequence represented by SEQ ID NO:14 as mentioned below binds to the N-terminus of the protein having the amino acid sequence represented by SEQ ID NO:1 of the present invention (that is, a protein having the amino acid sequence represented by SEQ ID NO:11), (ii) a protein in which the signal peptide of the present invention having an amino acid sequence represented by SEQ ID NO:15 as mentioned below is deleted from the N-terminus of the precursor protein having the amino acid sequence represented by SEQ ID NO:11 of the present invention (that is, a protein having the amino acid sequence represented by SEQ ID NO:10), (iii) a protein in which the signal peptide of the present invention having an amino acid sequence represented by SEQ ID NO:16 as mentioned below binds to the N-terminus of the protein having the amino acid sequence represented by SEQ ID NO:2 of the present invention (that is, a protein having the amino acid sequence represented by SEQ ID NO:12), (iv) a protein in which the signal peptide of the present invention having an amino acid sequence represented by SEQ ID NO:17 as mentioned below binds to the N-terminus of the protein having the amino acid sequence represented by SEQ ID NO:3 of the present invention (that is, a protein having the amino acid sequence represented by SEQ ID NO:13), and so on.

As the precursor proteins of the present invention have the signal peptide, it can secrete the protein of the present invention outside of cells. And, the precursor proteins are useful as intermediates for producing the protein of the present invention.

The precursor proteins of the present invention have the same functions as the protein of the present invention as mentioned below, for example, physiological activities such as a nerve-extending activity and a neuro-regenerative activity in the central nervous system, etc., a gliacyte stimulating activity, an activity of forming memories in brain, and have a utility in the same way as the protein of the present invention.

Examples of the signal peptide of the present invention includes a signal peptide having (i) an amino acid sequence represented by SEQ ID NO:14 (a 1st to 37th amino acid sequence of SEQ ID NO: 11 or FIG. 1), (ii) an amino acid sequence represented by SEQ ID NO:15 (a 1st to 24th amino acid sequence of SEQ ID NO:11 or FIG. 1), (iii) an amino acid sequence represented by SEQ ID NO:16 (a 1st to 34th amino acid sequence of SEQ ID NO:12 or FIG. 2) or (iv) an amino acid sequence represented by SEQ ID NO:17 (a 1st to 34th amino acid sequence of SEQ ID NO:13 or FIG. 3) or (v) a substantial equivalent thereto, and so on.

The signal peptide of the present invention may be a peptide derived from the above-mentioned cells of mammals or all tissues in which such cells are present, or may be a peptide derived from fishes such as goldfish, zebrafish, salmon, trout, herring and carp, or may be a synthetic signal peptide.

Examples of the substantially equivalent amino acid sequence to the amino acid sequence represented by SEQ ID NO:14 are an amino acid sequence having an identity of not less than about 60%, preferably not less than about 70%, more preferably about 80%, furthermore preferably not less than about 90%, most preferably not less than about 95% to the amino acid sequence represented by SEQ ID NO:14, and so on.

Examples of the substantially equivalent amino acid sequence to the amino acid sequence represented by SEQ ID NO:15 are an amino acid sequence having an identity of not less than about 60%, preferably not less than about 70%, more preferably about 80%, furthermore preferably not less than about 90%, most preferably not less than about 95% to the amino acid sequence represented by SEQ ID NO:15, and so on.

Examples of the substantially equivalent amino acid sequence to the amino acid sequence represented by SEQ ID NO:16 are an amino acid sequence having an identity of not less than about 60%, preferably not less than about 70%, more preferably about 80%, furthermore preferably not less than about 90%, most preferably not less than about 95% to the amino acid sequence represented by SEQ ID NO:16, and so on. Examples of the substantially equivalent amino acid sequence to the amino acid sequence represented by SEQ ID NO:17 are an amino acid sequence having an identity of not less than about 60%, preferably not less than about 70%, more preferably about 80%, furthermore preferably not less than about 90%, most preferably not less than about 95% to the amino acid sequence represented by SEQ ID NO:17, and so on.

The signal peptides of the present invention include any peptides having the substantially equivalent amino acid sequence to the amino acid sequence represented by SEQ ID NO:14, SEQ ID NO:15, SEQ ID NO:16 or SEQ ID NO:17, and capable of showing a function as a signal peptide. Therefore, it is allowable that even differences among molecular weight, etc. are present.

And, the signal peptides of the present invention may include a peptide comprising (i) an amino acid sequence wherein one or more amino acid residues (e.g. about 1 to 6, preferably a few (e.g. 1 to 4) amino acid residues) are deleted from the amino acid sequence as mentioned above, (ii) an amino acid sequence wherein one or more amino acid residues (e.g. about 1 to 6, preferably a few (e.g. 1 to 4) amino acid residues) are added to the amino acid sequence as mentioned above, (iii) an amino acid sequence wherein one or more amino acid residues (e.g. about 1 to 6, preferably a few (e.g. 1 to 4) amino acid residues) in the amino acid sequence as mentioned above, or (iv) a combination thereof, and so on, as long as the signal peptide shows a function as a signal peptide.

The signal peptides of the present invention are usually in the carboxyl (—COOH) or carboxylate (—COO⁻) form at C-terminus, but may instead be in the amide (—CONH$_2$) or ester (—COOR) form in the same manner as the protein of the present invention as mentioned above.

The specific examples of the signal peptides of the present invention are (1) a peptide having an amino acid sequence represented by SEQ ID NO:14, (2) a peptide having an amino acid sequence represented by SEQ ID NO:15, (3) a peptide having an amino acid sequence represented by SEQ ID NO:16, (4) a peptide having an amino acid sequence wherein Gly is deleted from the C-terminus of the amino acid sequence represented by SEQ ID NO:16, (5) a peptide having an amino acid sequence represented by SEQ ID NO:17, (6) a peptide having an amino acid sequence wherein 7 amino acid residues are deleted from the C-terminus of the amino acid sequence represented by SEQ ID NO:17 and so on.

The signal peptides of the present invention can secrete various endocelluar secretory protein (or peptide) such as the protein of the present invention effectively.

The salts of the protein, the partial peptide, the precursor protein or the signal peptide of the present invention include salts with physiologically acceptable bases (e.g. alkali metals) or acids such as organic or inorganic acids, and are preferably physiologically acceptable acid addition salts. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, maleic acid, oxalic acid, benzoic acid, methanesulfonic acid or benzenesulfonic acid, etc . . . . )

The protein, its partial peptide, the precursor protein, the signal peptide or a salt thereof of the present invention (hereinafter referred to as the protein of the present invention, in the description on the method for producing them) can be produced from the tissues or cells of mammals by per se known technology for purification of proteins or peptides or, as described hereinafter, by culturing a transformant carrying a DNA encoding the protein. It can also be produced in accordance with the procedures for peptide synthesis which are described hereinafter.

When the protein of the present invention is produced from the tissues or cells of mammals, the tissues or cells of mammals are homogenized and the protein of the present invention is extracted by an acid, etc. The protein can be purified and isolated from the extract by a combination of chromatography such as reverse phase chromatography, ion exchange chromatography and so on.

For the synthesis of the protein of the present invention or their amide form, any of commercial resins available for protein synthesis can be employed. Such resins include chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethylmethylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be beforehand protected at side-chain functional groups in a suitable manner can be serially condensed with the α-amino group in the order corresponding to the amino acid sequence of the objective protein or peptide by various condensation techniques which are per se known. After completion of the final condensation reaction, the protein or peptide is separated from the resin and the protective groups are removed. Then, in highly diluted solution, the intramolecular disulfide-forming reaction is carried out to provide the objective proteins or amides thereof.

Referring to the above condensation of protected amino acids, various activating agents known to be useful for protein synthesis can be utilized, and carbodiimide reagents are especially preferred. The carbodiimide reagents include DCC, N,N'-diisopropylcarbodiimide, and N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or a conjugation thereof to the resin can be optionally selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, etc.), sulfoxides (e.g. dimethyl sulfoxide, etc.), ethers (e.g. pyridine, dioxane, tetrahydrofuran, etc.), nitrites (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the sufficient condensation thoroughly. When sufficient condensation can not be achieved by the repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower($C_{1-6}$) alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, $Cl_2$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diisopropylethylamine, triethylamine, piperidine, piperazine or the like, and reduction with sodium metal in liquid ammonia. The above deprotection by treatment with acid is generally conducted at a temperature of about −20° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be optionally selected from among the known methods and groups.

An alternative method for providing the protein in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent as mentioned above. The condensation reaction can be carried out in the same manner as described hereinbefore. After purification of the protected protein thus obtained by condensation, all the protective groups are eliminated by the procedures described hereinbefore to provide the contemplated protein in crude form. This crude protein is purified by suitable known purification techniques and lyophilized to provide the desired protein amide.

A method for providing the protein in an ester form comprises condensing the α-carboxyl group of the C-terminal amino acid with a suitable alcohol to prepare the corresponding ester and subjecting this ester to the same procedure as described for purification of the protein amide to provide the objective ester of the protein.

The partial peptide of the present invention or a salt thereof can be produced by per se known procedures for peptide synthesis or by cleaving the protein with a suitable peptidase. The process for peptide synthesis may be a solid-phase synthesis and/or a liquid-phase synthesis. Namely, the objective peptide can be produced by condensing a partial peptide or amino acid capable of constituting the partial peptide of the present invention with the residual part thereof and, when the product has a protective group, the protective group is removed whereupon a desired peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966

(2) Schroeder and Luebke, The Peptide, Academic Press, New York, 1965

(3) Nobuo Izumiya et al., Fundamentals and Experiments in Peptide Synthesis, Maruzen, 1975

(4) Haruaki Yajima and Shumpei Sakakibara, Biochemical Experiment Series 1, Protein Chemistry IV, 205, 1977

(5) Haruaki Yajima (ed.), Development of Drugs-Continued, 14, Peptide Synthesis, Hirokawa Shoten After the reaction, the partial peptide of the present invention can be purified and isolated by a combination of conventional purification techniques such as solvent extraction, distillation, column chromatography, liquid chromatography, and recrystallization. When the partial peptide isolated as above is in a free form, it can be converted to a suitable salt by known methods or a method analogous thereto. On the other hand, when it is isolated as a salt, it can be converted to a free form or to any other salt thereof by known methods or a method analogous thereto.

The DNA coding for the protein of the present invention may be any DNAs comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or a mRNA fraction prepared from the tissues or cells, a direct amplification can be carried out by Reverse Transcriptase Polymerase Chain Reaction (hereinafter, referred to as RT-PCR method) technique.

Examples of DNA coding for the protein comprising the amino acid sequence represented by SEQ ID NO:1 or a substantial equivalent thereto of the present invention are (1) a DNA comprising a nucleotide sequence represented by SEQ ID NO:18, or (2) a DNA which comprises a nucleotide sequence hybridizing to the nucleotide sequence represented by SEQ ID NO:18 under a high stringent condition and codes for a protein having a substantially and qualitatively equivalent activity (e.g. nerve-extending activity or neuro-regenerative activity in the central nervous system, etc., gliacyte stimulating activity, activity of forming memories in brain) to the protein comprising the amino acid sequence represented by ID No:1.

Examples of the nucleotide sequence hybridizing to the nucleotide sequence represented by SEQ ID NO:18 are a nucleotide sequence which has not less than about 60%, preferably not less than about 70%, more preferably not less than about 80%, still more preferably not less than about 90%, most preferably not less than about 95% identity to the nucleotide sequence represented by SEQ ID NO:18.

Examples of DNA coding for the protein comprising the amino acid sequence represented by SEQ ID NO:2 or a substantial equivalent thereto of the present invention are (1) a DNA comprising a nucleotide sequence represented by SEQ ID NO:19, or (2) a DNA which comprises a nucleotide sequence hybridizing to the nucleotide sequence represented by SEQ ID NO:19 under a high stringent condition and codes for a protein having a substantially and qualitatively equivalent activity (e.g. nerve-extending activity or neuro-regenerative activity in the central nervous system, etc., gliacyte stimulating activity, activity of forming memories in brain) to the protein comprising the amino acid sequence represented by ID No:2, and so on.

Examples of the nucleotide sequence hybridizing to the nucleotide sequence represented by SEQ ID NO:19 are a nucleotide sequence which has not less than about 60%, preferably not less than about 70%, more preferably not less than about 80%, still more preferably not less than about 90%, most preferably not less than about 95% identity to the nucleotide sequence represented by SEQ ID NO:19.

Examples of DNA coding for the protein having the amino acid sequence represented by SEQ ID NO:3 or a substantial equivalent thereto of the present invention are (1) a DNA comprising a nucleotide sequence represented by SEQ ID NO:20, or (2) a DNA which comprises a nucleotide sequence hybridizing to the nucleotide sequence represented by SEQ ID NO:20 under a high stringent condition and codes for a protein having a substantially and qualitatively equivalent activity (e.g. nerve-extending activity or neuro-regenerative activity in the central nervous system, etc., gliacyte stimulating activity, activity of forming memories in brain) to the protein comprising the amino acid sequence represented by ID No:3, and so on.

Examples of the nucleotide sequence hybridizing to the nucleotide sequence represented by SEQ ID NO:20 are a nucleotide sequence which has not less than about 60%, preferably not less than about 70%, more preferably not less than about 80%, still more preferably not less than about 90%, most preferably not less than about 95% identity to the nucleotide sequence represented by SEQ ID NO:20.

The hybridization can be carried out by Per se known methods such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out under a high stringent condition.

Under the high stringent condition, Na concentration is at about 19 to 40 mM, preferably about 19 to 20 mM and a temperature is at about 50 to 70° C., preferably about 60 to 65° C. Particularly, the condition at about 19 mM of Na$^+$ and about 65° C. is preferred.

Preferable examples of the DNA coding for the protein comprising the amino acid sequence represented by SEQ ID NO:1 are a DNA comprising the nucleotide sequence represented by SEQ ID NO:18.

Preferable examples of the DNA coding for the protein comprising the amino acid sequence represented by SEQ ID NO:2 are a DNA comprising the nucleotide sequence represented by SEQ ID NO:19.

Preferable examples of the DNA coding for the protein comprising the amino acid sequence wherein Gly is added to the N-terminus of the amino acid sequence represented by SEQ ID NO:2 are a DNA comprising the nucleotide sequence wherein GGC are added to the 5'-terminus of the nucleotide sequence represented by SEQ ID NO:19.

Preferable example of the DNA coding for the protein comprising the amino acid sequence represented by SEQ ID NO:3 are a DNA comprising the nucleotide sequence represented by SEQ ID NO:20.

Preferable examples of the DNA coding for the protein comprising the amino acid sequence wherein 7 amino acid residues of the C-terminus of the amino acid sequence represented by SEQ ID NO:17 are added to the N-terminus of the amino acid sequence represented by SEQ ID NO:3 are a DNA comprising the nucleotide sequence wherein 21 bases of the 3'-terminus of the nucleotide sequence represented by SEQ ID NO:34 are added to the 5'-terminus of the nucleotide sequence represented by SEQ ID NO:20.

And, examples of the DNA coding for the protein comprising at least one amino acid sequence represented by SEQ ID NO:4, SEQ ID NO:5, SEQ ID NO:6 or SEQ ID NO:7 are a DNA comprising a nucleotide sequence represented by SEQ ID NO:21, SEQ ID NO:22, SEQ ID NO:23 or SEQ ID NO:24, and so on.

Furthermore, examples of the DNA coding for the protein comprising at least one amino acid sequence represented by SEQ ID NO:4, SEQ ID NO:8, SEQ ID NO:9 or SEQ.ID NO:7 are a DNA comprising a nucleotide sequence represented by SEQ ID NO:21, SEQ ID NO:25, SEQ ID NO:26 or SEQ ID NO:24, and so on.

The DNA coding for the partial peptide of the present invention may be any DNAs comprising a nucleotide sequence encoding the partial peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or a mRNA fraction prepared from the tissues or cells, a direct amplification can be carried out by RT-PCR method.

Examples of DNA coding for the partial peptide of the present invention are (i) a DNA comprising a partial nucleotide sequence of DNA which comprises a nucleotide sequence represented by SEQ ID NO:18, SEQ ID NO:19 or SEQ ID NO:20, or (ii) a DNA comprising a partial nucleotide sequence of DNA which comprises a nucleotide sequence hybridizing under a high stringent condition to the nucleotide sequence represented by SEQ ID NO:18, SEQ ID NO:19 or SEQ ID NO:20 and codes for a protein having a substantially and qualitatively equivalent activity (e.g. nerve-extending activity or neuro-regenerative activity in the central nervous system, etc., gliacyte stimulating activity, activity of forming memories in brain) to the protein of the present invention.

Examples of the nucleotide sequence hybridizing to the nucleotide sequence represented by SEQ ID NO:18, SEQ ID NO:19 or SEQ ID NO:20 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:18, SEQ ID NO:19 or SEQ ID NO:20, and so on.

More specifically, examples of the DNA coding for the partial peptide comprising the amino acid sequence represented by SEQ ID NO:4, SEQ ID NO:5, SEQ ID NO:6 or SEQ ID NO:7 are (i) a DNA having the nucleotide sequence represented by SEQ ID NO:21, SEQ ID NO:22, SEQ ID NO:23 or SEQ ID NO:24, (ii) a DNA which has a nucleotide sequence hybridizing under a high stringent condition to the nucleotide sequence represented by SEQ ID NO:21, SEQ ID NO:22, SEQ ID NO:23 or SEQ ID NO:24, and so on.

Examples of the nucleotide sequence hybridizing to the nucleotide sequence represented by SEQ ID NO:21, SEQ ID NO:22, SEQ ID NO:23 or SEQ ID NO:24 are a nucleotide sequence of not less than about 60%, preferably not less than about 70%, more preferably not less than about 80%, furthermore preferably not less than about 90%, most preferably not less than about 95% identity to the nucleotide sequence represented by SEQ ID NO:21, SEQ ID NO:22, SEQ ID NO:23 or SEQ ID NO:24, and so on.

Specific examples of the DNA coding for the partial peptide having an amino acid sequence represented by SEQ ID NO:4, SEQ ID NO:5, SEQ ID NO:6 or SEQ ID NO:7 are a DNA having a nucleotide sequence represented by SEQ ID NO:21, SEQ ID NO:22, SEQ ID NO:23 or SEQ ID NO:24, and so on.

Examples of the DNA coding for the partial peptide having the amino acid sequence represented by SEQ ID NO:4, SEQ ID NO:8, SEQ ID NO:9 or SEQ ID NO:7 are (i) a DNA having the nucleotide sequence represented by SEQ ID NO:21, SEQ ID NO:25, SEQ ID NO:26 or SEQ ID NO:24, (ii) a DNA which has the nucleotide sequence hybridizing under a high stringent condition to the nucleotide sequence represented by SEQ ID NO:21, SEQ ID NO:25, SEQ ID NO:26 or SEQ ID NO:24, and so on.

Examples of the nucleotide sequence hybridizing to the nucleotide sequence represented by SEQ ID NO:21, SEQ ID NO:25, SEQ ID NO:26 or SEQ ID NO:24 are a nucleotide sequence of not less than about 60%, preferably not less than about 70%, more preferably not less than about 80%, furthermore preferably not less than about 90%, most preferably not less than about 95% identity to the nucleotide sequence represented by SEQ ID NO:21, SEQ ID NO:25, SEQ ID NO:26 or SEQ ID NO:24, and so on.

Specific examples of the DNA coding for the partial peptide having an amino acid sequence represented by SEQ ID NO:4, SEQ ID NO:8, SEQ ID NO:9 or SEQ ID NO:7 are a DNA having a nucleotide sequence represented by SEQ ID NO:21, SEQ ID NO:25, SEQ ID NO:26 or SEQ ID NO:24, and so on.

And, examples of the DNA coding for the partial peptide comprising a 41st to 106th, 121st to 179th or 187th to 211st amino acid sequense of the amino acid sequence represented by any one of SEQ ID NO:11 to SEQ ID NO:13 or FIG. 4 are (i) a 121st to 318th, 360th to 537th or 559th to 633rd nucleotide sequence of the nucleotide sequence represented by any one of SEQ ID NO:28 to SEQ ID NO:30 or (ii) a nucleotide sequence hybridizing under a high stringent condition to the 121st to 318th, 360th to 537th or 559th to 633rd nucleotide sequence of the nucleotide sequence represented by any one of SEQ ID NO:28 to SEQ ID NO:30.

Examples of the nucleotide sequence hybridizing under a high stringent condition to the 121st to 318th, 360th to 537th or 559th to 633rd nucleotide sequence of the nucleotide sequence represented by any one of SEQ ID NO:28 to SEQ ID NO:30 are a nucleotide sequence of not less than about 60%, preferably not less than about 70%, more preferably not less than about 80%, furthermore preferably not less than about 90%, most preferably not less than about 95% identity to the 121st to 318th, 360th to 537th or 559th to 633rd nucleotide sequence of the nucleotide sequence represented by any one of SEQ ID NO:28 to SEQ ID NO:30.

The method of hybridization and the high stringent condition are the same as mentioned above.

More specifically, preferable examples of the DNA coding for the partial peptide comprising a 41st to 1096th, 121st to 179th or 187th to 211st amino acid sequence of the amino acid sequence represented by any one of SEQ ID NO:1 to SEQ ID NO:13 or FIG. 4 are a 121st to 318th, 360th to 537th or 559th to 633rd nucleotide sequence of the nucleotide sequence represented by any one of SEQ ID NO:28 to SEQ ID NO:30.

The DNA coding for the precursor protein of the present invention may be any DNAs comprising a nucleotide sequence encoding the precursor protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid and phagemid. Furthermore, using a total RNA fraction or a mRNA fraction prepared from the tissues or cells, a direct amplification can be carried out by RT-PCR method.

Examples of the DNA coding for the precursor proteins comprising the amino acid sequence represented by SEQ ID NO:10 or a substantial equivalent thereto are (i) a DNA comprising a nucleotide sequence represented by SEQ ID NO:27 or (ii) a DNA comprising a nucleotide sequence which hybridizes under a high stringent condition to the nucleotide sequence represented by SEQ ID NO:27 and codes for the protein capable of yielding the protein of the present invention as mentioned above.

Examples of the nucleotide sequence hybridizing under a high stringent condition to the nucleotide sequence represented by SEQ ID NO:27 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:27, and so on.

Specific examples of the DNA coding for the precursor protein comprising an amino acid sequence represented by SEQ ID NO:10 are a DNA having a nucleotide sequence represented by SEQ ID NO:27.

Examples of the DNA coding for the precursor proteins comprising the amino acid sequence represented by SEQ ID NO:1 or a substantially equivalent thereto are (i) a DNA comprising a nucleotide sequence represented by SEQ ID NO:28 or (ii) a DNA comprising a nucleotide sequence which hybridizes under a high stringent condition to the nucleotide sequence represented by SEQ ID NO:28 and codes for the protein capable of yielding the protein of the present invention as mentioned above.

Examples of the nucleotide sequence hybridizing under a high stringent condition to the nucleotide sequence represented by SEQ ID NO:28 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:28, and so on.

Specific examples of the DNA coding for the precursor protein comprising an amino acid sequence represented by SEQ ID NO:1 are a DNA having a nucleotide sequence represented by SEQ ID NO:28.

Examples of the DNA coding for the precursor proteins comprising the amino acid sequence represented by SEQ ID NO:12 or a substantially equivalent thereto are (i) a DNA comprising a nucleotide sequence represented by SEQ ID NO:29 or (ii) a DNA comprising a nucleotide sequence which hybridizes under a high stringent condition to the nucleotide sequence represented by SEQ ID NO:29 and codes for the protein capable of yielding the protein of the present invention as mentioned above.

Examples of the nucleotide sequence hybridizing under a high stringent condition to the nucleotide sequence represented by SEQ ID NO:29 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:29, and so on.

Specific examples of the DNA coding for the precursor protein comprising an amino acid sequence represented by SEQ ID NO:12 are a DNA having a nucleotide sequence represented by SEQ ID NO:29.

Examples of the DNA coding for the precursor proteins comprising the amino acid sequence represented by SEQ ID NO:13 or a substantial equivalent thereto are (i) a DNA comprising a nucleotide sequence represented by SEQ ID NO:30 or (ii) a DNA comprising a nucleotide sequence which hybridizes under a high stringent condition to the nucleotide sequence represented by SEQ ID NO:30 and codes for the protein capable of yielding the protein of the present invention as mentioned above.

Examples of the nucleotide sequence hybridizing under a high stringent condition to the nucleotide sequence represented by SEQ ID NO:30 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:30, and so on.

Specific examples of the DNA coding for the precursor protein comprising an amino acid sequence represented by SEQ ID NO:13 are a DNA having a nucleotide sequence represented by SEQ ID NO:30.

The method of hybridization and the high stringent condition are the same as mentioned above.

The DNA coding for the signal peptide of the present invention may be any DNAs comprising a nucleotide sequence encoding the signal peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid and phagemid. Furthermore, using a total RNA fraction or a mRNA fraction prepared from the tissues or cells, a direct amplification can be carried out by RT-PCR method.

Examples of the DNA coding for the signal peptide having the amino acid sequence represented by SEQ ID NO:14 or a substantial equivalent thereto are (i) a DNA comprising a nucleotide sequence represented by SEQ ID NO:31 or (ii) a DNA comprising a nucleotide sequence which hybridizes under a high stringent condition to the nucleotide sequence represented by SEQ ID NO:31 and codes for the peptide capable of showing a function as a signal peptide.

Examples of the nucleotide sequence hybridizing under a high stringent condition to the nucleotide sequence represented by SEQ ID NO:31 are a nucleotide sequence which has not less than about 60%, preferably not less than about 70%, more preferably not less than about 80%, furthermore preferably not less than about 90%, more preferably not less than about 95% identity to the nucleotide sequence represented by SEQ ID NO:31, and so on.

Specific examples of the DNA coding for the signal peptide having an amino acid sequence represented by SEQ ID NO:14 are a DNA having a nucleotide sequence represented by SEQ ID NO:31.

Examples of the DNA coding for the signal peptide having the amino acid sequence represented by SEQ ID NO:15 or a substantial equivalent thereto are (i) a nucleotide sequence represented by SEQ ID NO:32 or (ii) a nucleotide sequence which hybridizes under a high stringent condition to the nucleotide sequence represented by SEQ ID NO:32 and codes for the peptide capable of showing a function as a signal peptide.

Examples of the nucleotide sequence hybridizing under a high stringent condition to the nucleotide sequence represented by SEQ ID NO:32 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:32, and so on.

Specific examples of the DNA coding for the signal peptide having an amino acid sequence represented by SEQ ID NO:15 are a DNA having a nucleotide sequence represented by SEQ ID NO:32.

Examples of the DNA coding for the signal peptide having the amino acid sequence represented by SEQ ID NO:16 or a substantial equivalent thereto are (i) a DNA comprising a nucleotide sequence represented by SEQ ID NO:33 or (ii) a DNA comprising a nucleotide sequence which hybridizes under a high stringent condition to the nucleotide sequence represented by SEQ ID NO:33 and codes for the peptide capable of showing a function as a signal peptide.

Examples of the nucleotide sequence hybridizing under a high stringent condition to the nucleotide sequence represented by SEQ ID NO:33 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:33, and so on.

Specific examples of the DNA coding for the signal peptide having an amino acid sequence represented by SEQ ID NO:16 are a DNA having a nucleotide sequence represented by SEQ ID NO:33.

Specific examples of the DNA coding for the signal peptide having an amino acid sequence wherein Gly is deleted from the C-terminus of the amino acid sequence represented by SEQ ID NO:16 are a DNA having a nucleotide sequence wherein GGC are deleted from the 3'-terminus of the nucleotide sequence represented by SEQ ID NO:33.

Examples of the DNA coding for the signal peptide having the amino acid sequence represented by SEQ ID NO:17 or a substantial equivalent thereto are (i) a DNA comprising a nucleotide sequence represented by SEQ ID NO:34 or (ii) a DNA comprising a nucleotide sequence which hybridizes under a high stringent condition to the nucleotide sequence represented by SEQ ID NO:34 and codes for the peptide capable of showing a function as a signal peptide.

Examples of the nucleotide sequence hybridizing under a high stringent condition to the nucleotide sequence represented by SEQ ID NO:34 are a nucleotide sequence which has not less than about 60%, preferably not less than about 70%, more preferably not less than about 80%, furthermore preferably not less than about 90%, most preferably not less than about 95% identity to the nucleotide sequence represented by SEQ ID NO:34, and so on.

Specific examples of the DNA coding for the signal peptide having an amino acid sequence represented by SEQ ID NO:17 are a DNA having a nucleotide sequence represented by SEQ ID NO:34.

Specific examples of the DNA coding for the signal peptide having an amino acid sequence wherein 7 amino acid residues are deleted from the C-terminus of the amino acid sequence represented by SEQ ID NO:17 are a DNA having a nucleotide sequence wherein 21 bases are deleted from the 3'-terminus of the nucleotide sequence represented by SEQ ID NO:34.

The method of hybridization and the high stringent condition are the same as mentioned above.

The DNA encoding the protein, the partial peptide or the precursor protein of the present invention (hereinafter referred to as the protein of the present invention) can be cloned either by PCR amplification by using synthetic DNA primers having a partial nucleotide sequence of the DNA coding for the protein or by hybridization using the DNA inserted in a suitable vector and labeled DNA fragment or synthetic DNA coding for a part or full region of the protein of the present invention. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The DNA coding for the partial peptide or the signal peptide of the present invention can be prepared according to the per se known method for producing oligonucleotides.

The substitution of the nucleotide sequence of the DNA can be carried out by the per se known method such as Gapped duplex method, Kunkel method and so on by using known kits such as Mutan™-G (Takara), Mutan™-K (Takara) and so on.

The cloned DNA coding for the protein of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adapters.

An expression vector for the protein of the present invention can be constructed by, for example, (a) cutting out an objective DNA fragment from the DNA for the protein of the present invention and (b) ligating the objective DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, etc.; bacteriophages such as λ-phage; animal virus such as retrovirus, vaccinia virus, etc.; insect virus; and other vectors such as pA1-11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter includes CAG promoter, SRα promoter, SV40 promoter, LTR promoter, CMV (cytomegalovirus) promoter, HSV-TK promoter, etc., and CAG promoter and SRα promoter are preferably used. When the host for the transformation is *Escherichia coli*, the promoter includes preferably trp promoter, lac promoter, recA promoter, $\lambda P_L$ promoter, lpp promoter, T7 promoter, etc. When the host for the transformation is Bacillus, the promoter includes preferably SPO1 promoter, SPO2 promoter, penP promoter, etc. When the host is a yeast, the promoter includes preferably PHO5 promoter, PGK promoter, GAP promoter, ADH1 promoter, etc. When the host is an insect cell, the promoter includes polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolic acid reductase (hereinafter referred to as dhfr gene), ampicillin resistant gene (hereinafter referred to as Amp'), neomycin-resistant gene (hereinafter referred to as Neo) and so on. The dhfr gene gives methotrexate (MTX) resistance and Neo gives G418 resistance. Particularly, when the dhfr gene is used as a selective marker against dhfr gene-deficient chinese hamster cell lines, cells transfected with the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is Bacillus, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is produced by using the vector thus constructed, which carries the DNA coding for the protein of the present invention.

The host may be, for example, Escherichia species, Bacillus species, yeast cells, insect cells, insects, animal cells, etc.

Examples of Escherichia species include *Escherichia coli* K12.DH1 (Proc. Natl. Acad. Sci. USA, 60, 160 (1968)), JM103 (Nucleic Acids Research, 9, 309 (1981)), JA221 (J. Mol. Biol. 120, 517 (1978)), HB101 (J. Mol. Biol., 41, 459 (1969)), C600 (Genetics, 39, 440 (1954)), etc.

Examples of Bacillus species are, for example, *Bacillus subtilis* MI114 (Gene, 24, 255 (1983)), 207–21 (J. Biochem., 95, 87 (1984)), etc.

Examples of yeast cells are, for example, *Saccharomyces cerevisiae* AH22, AH22R⁻, NA87-11A, DKD-5D or 20B-12, *Schizosachcaromyces pombe* NCYC1913 or NCYC2036, or *Pichia pastoris* KM71, etc.

Examples of insect cells are, for example, *Spodoptera frugiperda* cell (Sf cell), MG1 cell derived from center intestine of Trichoplusia ni, High Five™ cell derived from eggs of Trichoplusia ni, Mamestra brassicae-derived cell, Estigmena acrea-derived cell and so on when virus is AcNPV; and *Bombyx mori* N cell (BmN cell) and so on when virus is BmNPV. Examples of the Sf cell are, for example, Sf9 cell (ATCC CRL 1711), Sf21 cell (both, Vaughn J. L. et al., In Vivo, 13, 213–217(1977)) and so on.

Examples of insects include a larva of silkworm (*Bombyx mori* larva) (Maeda et al., Nature, 315, 592(1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr⁻) cell), L cell, myeloma cell, human FL cell, 293 cell, C127 cell, BALB/3T3 cell, Sp-2/0 cell, etc. Among them, CHO cell, CHO(dhfr⁻) cell, 293 cell, etc. are preferred.

Depending on host cells used, transformation is done using standard techniques appropriate to such cells.

Transformation of Escherichia species can be carried out in accordance with methods as disclosed in, for example, Proceedings of the National Academy of Sciences of the United State of America, Vol. 69, 2110 (1972), and Gene, Vol. 17, 107 (1982), etc.

Transformation of Bacillus species can be carried out in accordance with methods as disclosed in, for example, Molecular & General Genetics, Vol. 168, 111 (1979), etc.

Transformation of yeast cells can be carried out in accordance with methods as disclosed in, for example, Methods in Enzymology, Vol. 194, 182–187(1991), Proceedings of the National Academy of Sciences of the United State of America, vol. 75, 1929 (1978), etc.

Transformation of insect cells or insects can be carried out in accordance with methods as disclosed in, for example, Bio/Technology, Vol. 6, 47–55, (1988).

Transformation of animal cells can be carried out by methods as disclosed in, for example, Cell Engineering, separate Vol. 8, New Cell Engineering Experiment Protocol, 263–267(1995) (Shujun Company), Virology, Vol. 52, 456 (1973), etc.

In introducing the expression vector into cells, known methods such as a calcium phosphate method (Graham, F. L. and van der Eb, A. J., Virology, 52, 456–467(1973)), an electroporation (Neumann, E. et al., EMBO J., 1,841–845 (1982)), etc. may be used.

The transformants or transfectants wherein the expression vector carrying the DNA coding for the protein of the present invention can be obtained according to the aforementioned techniques.

Examples of methods for expressing the protein of the present invention stably using animal cells are a method for selecting the cells wherein the above-mentioned expression vector is incorporated in the chromosome by means of clone selection. Briefly, the transformant is first selected using the above-mentioned selective marker as an index for selection. Then the animal cell produced as such by using the selective marker is repeatedly subjected to a clone selection to give an animal cell strain which stably exhibits a high ability of expressing the protein of the present invention. When a dhfr gene is used as a selective marker, the drug-resistant cells are selected by a culture with sequentially increasing the MTX concentration to amplify the DNA coding for the protein of the present invention with dhfr gene in the cells whereby an animal cell strain exhibiting far higher expression can be obtained.

The protein of the present invention or a salt thereof can be also manufactured by culturing the transformant under a condition where the DNA coding for the protein of the present invention can be expressed to express and accumulate the protein of the present invention.

Culture of the transformants (or transfectants) of Escherichia or Bacillus species can be carried out preferably in a liquid culture medium. The culture medium may contain carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of minerals include calcium chloride, sodium dihydrogen phosphate, magnesium chloride, etc. It is further allowable to add yeast extracts, vitamins, growth factors, etc. It is suitable that the pH of culture medium is at about 5 to 8.

The culture medium for Escherichia species is, for example, preferably M9 medium which contains glucose and casamino acid (Miller, Journal of Experiments in Molecular Genetics, 431–433, Cold Spring Harbor Laboratory, New York, (1972)). If necessary, drugs such as 3β-indolyl acrylic acid can be added to the medium to improve the efficiency of the promoter. In the case of Escherichia organisms as a host, the culture is carried out usually at about 15 to 43° C. for about 3 to 24 hours. As required, aeration and stirring may be applied. In the case of Bacillus organisms as a host, the culture is carried out usually at about 30 to 40° C. for about 6 to 24 hours. As required, aeration and stirring may also be applied.

In the case of yeast transformants, the culture medium used includes, for example, Burkholder minimum medium (Bostian, K. L. et al., Proc. Natl. Acad. Sci. USA, 77, 4505 (1980)), SD medium containing 0.5% casamino acid (Bitter, G. A. et al., Proc. Natl. Acad. Sci. USA, 81, 5330 (1984)), etc. It is preferable that the pH of the culture medium is adjusted to be from about 5 to 8. The culture is carried out usually at about 20 to 35° C. for about 24 to 72 hours. As required, aeration and stirring may be applied.

In the case of the transformants (or transfectants) of insect cells or insects, the culture medium used includes the Grace's insect medium supplemented with additives such as inactivated 10% bovine serum (Grace, T. C. C., Nature, 195, 788 (1962)). It is preferable that the pH of the culture medium is adjusted to be about 6.2 to 6.4. The culture is usually carried out at about 27° C. for about 3 to 5 days. As desired, aeration and stirring may be applied.

In the case of the transformants (or transfectants) of animal cells, the culture medium used includes MEM medium (Science, 122, 501 (1952)), DMEM medium (Virology, 8, 396 (1959)), RPMI 1640 medium (J. Amer. Med. Ass. 199, 519 (1967)), 199 medium (Proc. Sci. Biol. Med. 73, 1 (1950)), etc. which contain, for example, about 5 to 20% of fetal calf serum. It is preferable that the pH is from about 6 to 8. The culture is usually carried out at about 30 to 40° C. for about 15 to 72 hours. As required, medium exchange, aeration and stirring may be applied. Especially when CHO (dhfr⁻) cells and dhfr selective marker gene are used, it is preferred to use a DMEM medium containing a dialyzed fetal bovine serum which rarely contains thymidine.

Separation and purification of the protein from the above-mentioned cultures can be carried out according to methods described herein below.

To extract the protein from the cultured microorganisms or cells, the microorganisms or cells are collected by known methods after the culture, suspended in a suitable buffer solution, disrupted by ultrasonication, lysozyme and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case that proteins are secreted into culture media, supernatants are separated from the microorganisms or cells after culture and collected by known methods. The culture supernatant containing the protein can be purified by a suitable combination of known methods for separation, isolation and purification. The known methods of separation, isolation and purification include methods which utilize solubility, such as salting out or sedimentation with solvents, methods which utilize primarily a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In case that the protein thus obtained is in a free form, it can be converted to a salt thereof by known methods or a method analogous thereto. In case that the protein thus obtained is in a salt form vice versa, it can be converted to a free form or to any other salt thereof by known methods or a method analogous thereto.

The protein produced by the transformant can be arbitrarily modified or a part of polypeptide can be removed therefrom, by a suitable protein-modifying enzyme before or after the purification. The protein-modifying enzyme includes trypsin, chymotrypsin, arginyl endopeptidase, protein kinase, glycosidase, etc. The existence of the protein of the present invention thus obtained can be detected or determined by binding assay with a labeled ligand or by enzyme immunoassays (enzyme linked immunoassays) using specific antibodies, respectively.

The antibodies against the protein of the present invention, its partial peptide, the precursor protein or a salt thereof (hereinafter referred to as the protein, etc. of the present invention) are any antibodies such as polyclonal antibodies and monoclonal antibodies which can recognize the protein, etc. of the present invention. The antibody against the protein, etc. of the present invention may have an activity to neutralize an activity of the protein, etc. of the present invention.

The antibodies against the protein, etc. of the present invention may be manufactured by methods per se known to those of skill in the art or methods similar thereto, using the protein, etc. of the present invention as an antigen.

Preparation of a Monoclonal Antibody (a) Preparation of Monoclonal Antibody-Producing Cells The protein of the present invention is administered to mammals either solely or together with carriers or diluents to the site favorable for antibody production. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable mammals are monkeys, rabbits, dogs, guinea pigs, mice, rats, sheep and goats. The use of mice and rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from homogeneous or heterogeneous animals to obtain monoclonal antibody-producing hybridomas. Measurement of the antibody titer in antisera may, for example, be carried out by reacting a labeled protein, which will be mentioned later, with the antiserum followed by determining the binding activity of the labeling agent combined with the antibody. The cell fusion may be carried out, for example, by a method of Koehler and Milstein (Nature, 256, 495 (1975)).

Examples of the fusion accelerator are polyethylene glycol (PEG), Sendai virus, etc. and the use of PEG is preferred.

Examples of the myeloma cells are those derived from warm-blooded animals such as NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10 to 80% followed by incubating at 20 to 40° C., preferably, at 30 to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, then the protein, etc. labeled with a radioactive substance or an enzyme is added and monoclonal antibodies bound with the solid phase are detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101; Nissui Seiyaku, Japan). The culture temperature is usually 20 to 40° C. and, preferably, about 37° C. The culture period is usually from 5 days to 3 weeks and, preferably, 1 to 2 weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of a Polyclonal Antibody

The polyclonal antibody of the present invention can be produced by per se known methods or methods analogous thereto. The method comprises preparing an immunogen (protein antigen) per se or a conjugate of an imunogen with a carrier protein, immunizing a warm-blooded animal in the same manner as described for the production of the monoclonal antibody, harvesting a fraction containing the antibody against the protein, etc. of the present invention from the immunized animal, and purifying the harvested antibody.

Referring to the immunogen-carrier protein conjugate for use in the immunization of mammals, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or a diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host mammals.

The polyclonal antibody titer in the antiserum can be determined in the same manner as the determination of a monoclonal antibody described hereinbefore. The separation and purification of the polyclonal antibody can be carried out by the same method as the separation and purification of a monoclonal antibody.

The oligonucleotides or their derivatives having a nucleotide sequence complementary or substantially complementary to the DNA or mRNA coding for the protein, the partial peptide or the precursor protein of the present invention (hereinafter referred to as the DNA or mRNA of the present invention) can be any oligonucleotides or their derivatives which have a nucleotide sequence complementary or substantially complementary to that of the DNA or mRNA of the present invention and capable of promoting expression of the protein, etc. of the present invention.

The nucleotide sequence substantially complementary to the DNA or mRNA of the present invention may, for example, be a nucleotide sequence having an identity of not less than about 60%, preferably not less than about 70%, more preferably not less than about 80%, still more preferably not less than about 90%, more preferably not less than about 95% to the total nucleotide sequence or partial nucleotide sequence of the nucleotide sequence complementary to of the DNA or mRNA of the present invention. Particularly preferred is an oligonucleotide or a derivative thereof which has an identity of not less than about 60%, preferably not less than about 70%, and more preferably not less than about 80%, and still more preferably, not less than about 90%, more preferably not less than about 95% to the nucleotide sequence of the domain, of the complete nucleotide sequence complementary to that of the DNA or mRNA of the present invention, which encodes the N-terminal region of the protein of the present invention (e.g. the nucleotide sequence of the domain around the initiation codon). The oligonucleotides or their derivatives can be synthesized using a known DNA synthesis hardware.

The protein, its partial peptide or a salt thereof of the present invention has physiological activities such as a nerve-extending activity or neuro-regenerative activity in the central nervous system, etc., a gliacyte stimulating activity, an activity of formulating memories in brain. Therefore, the protein, its partial peptide or a salt thereof of the present invention can be used in various applications.

Typical applications of the protein, its partial peptide or a salt thereof of the present invention (hereinafter referred to collectively as the protein, etc. of the present invention), the DNA coding for the protein, etc. of the present invention (hereinafter briefly referred to as the DNA of the present invention), the antibody against the protein, etc. of the present invention (hereinafter briefly referred to as the antibody of the present invention) and the oligonucleotide or a derivative thereof are shown below.

(1) Pharmaceutical Composition

The protein, etc. of the present invention and the DNA of the present invention are useful as drugs such as therapeutic or prophylactic agent for a defect the gene coding for the protein of the present invention and associated diseases therewith, a dysfunction of the protein of the present invention and associated diseases therewith and so on. Specifically, the protein, etc. of the present invention or the DNA of the present invention are useful as drugs such as a therapeutic or prophylactic agent for Alzheimer's disease, Parkinson's disease, Huntington's disease, amyotrophic lateral sclerosis, dementia or cerebellar degeneration.

For example, when there is a patient in whom the protein, etc. of the present invention in the body cannot function sufficiently or normally because of its decrease or defect, the protein, etc. of the present invention of the patient can be expected to function sufficiently or normally by:

(a) administering the DNA coding for the protein, etc. of the present invention to the patient to express it;

(b) inserting the DNA coding for the protein, etc. of the present invention into cells to express it and transplanting the cells to the patient, or (c) administering the protein, etc. of the present invention to the patient.

For example, the protein, etc. of the present invention can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the protein, etc. of the present invention with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained.

When the DNA of the present invention is used as the above-mentioned drug, the DNA may be used alone or after inserting it into a suitable vector such as retrovirus vector, adenovirus vector, adenovirus-associated virus vector, pox virus etc. followed by administering the product vector to a warm-blooded animal by a conventional means. The DNA can also be administered as "naked" DNA, with physiologically acceptable carriers such as adjuvants to assist in uptake, by "gene" gun or by a catheter such as a catheter with a hydrogel.

If one wishes to use the protein, etc. of the present invention, one may use it in a purified form, preferably in a purity of at least 90%, more preferably at least 95%, still more preferably at least 98% and most preferably at least 99%.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, liquid carriers such as oils and fats may be incorporated in addition to the above-mentioned materials. Sterile compositions for injection can be formulated by ordinary methods of pharmaceutical preparation, for example, by dissolving or suspending active ingredients, naturally occuring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. An appropriate ampule is normally filled in with the thus-prepared pharmaceutical composition such as an injectable liquid.

The vector comprising the DNA of the present invention can be formulated as well as mentioned above, and usually can be used non-orally.

Because the thus-obtained preparation is safe and of low toxicity, it can be administered to mammals (e.g., human, rat, mouse, guinea pig, rabbit, sheep, pig, bovine, horse, cat, dog, monkey, etc.).

The dose of the protein, etc. of the present invention may vary depending on subject of disease, subject of administration, way of administration, and so on. When the protein, etc. of the present invention is used, for example, for treating Alzheimer's disease by oral administration, the dose of the protein, etc. of the present invention is normally about 0.1 to 100 mg, preferably 1.0 to 50 mg, and more preferably 1.0 to 20 mg per day for an adult human (weighing 60 kg). When the protein, etc. of the present invention is used, for example, for treating Alzheimer's disease by non-oral administration, it is advantageous to administer the protein, etc. of the present invention in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding doses as converted per 60 kg weight can be administered.

(2) Gene Diagnostic Agent

By using the DNA of the present invention as a probe, for instance, an abnormality (gene abnormality) of the DNA or mRNA coding for the protein, etc. of the present invention in mammals (e.g. human, rat, mouse, guinea pig, rabbit, sheep, swine, bovine, horse, cat, dog, monkey, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

The above-mentioned gene diagnosis using the DNA of the present invention can be carried out by, for example, the per se known Northern hybridization assay or PCR-SSCP assay (Genomics, 5, 874–879 (1989); Proc. Natl. Acad. Sci. USA, 86, 2766–2770 (1989)).

When a decrease in expression of the mRNA is detected or a mutation of the DNA is detected by the PCR-SSCP assay, it may lead, with high probability, to the diagnosis of Alzheimer's disease, Parkinson's disease, Huntington's disease, amyotrophic lateral scleorosis, dementia or cerebellar degeneration.

(3) Quantitative Determination of the Protein of the Present Invention, its Partial Peptide or a Salt Thereof The antibody of the present invention is capable of specifically recognizing the protein, etc. of the present invention and, accordingly, it can be used for quantitative determination of the protein, etc. of the present invention in test liquid samples and particularly for quantitative determination by sandwich immunoassays.

Thus, the present invention provides, for example, the following methods:

(i) a quantitative determination of the protein, etc. of the present invention in a test liquid sample, which comprises
  (a) competitively reacting the test liquid sample and a labeled protein, etc. of the present invention with the antibody of the present invention, and
  (b) measuring the ratio of the labeled protein, etc. of the present invention binding with the antibody; and (ii) a quantitative determination of the protein, etc. of the present invention in a test liquid sample, which comprises
  (a) reacting the test liquid sample with an antibody immobilized on an insoluble carrier and another labeled antibody simultaneously or continuously, and
  (b) measuring the activity of the labeling agent on the insoluble carrier, wherein one antibody is capable of recognizing the N-terminal region of the protein, etc. of the present invention while another antibody is capable of recognizing the C-terminal region of the protein, etc. of the present invention.

When the monoclonal antibody of the present invention recognizing the protein, etc. of the present invention (hereinafter, sometimes referred to as "monoclonal antibody of the present invention") is used, the quantity of the protein of the present invention can be determined and, moreover, the protein, etc. of the present invention can be detected by means of a tissue staining, etc. as well. For such an object, antibody molecules per se may be used, or $F(ab')_2$, Fab' or Fab fractions of the antibody molecule may also be used. There is no particular limitation for measuring methods using the antibody of the present invention and any measuring method may be used so far as it relates to a method in which the amount of antibody, antigen or antibody-antigen complex, depending on or corresponding to the amount of antigen, e.g. the amount of the protein, etc. of the present invention in the liquid sample to be determined, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are ($^{125}$I), ($^{131}$I), ($^{3}$H) and ($^{14}$C). Preferred examples of the enzyme are those which are stable and with much specific activity, such as β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or an antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich method, the test liquid is allowed to react with an insolubilized monoclonal antibody of the present invention (the first reaction), then it is allowed to react with an another labeled monoclonal antibody of the present invention (the second reaction) and the activity of the labeling agent on the insoluble carrier is measured whereupon the amount of the protein, etc. of the present invention in the test liquid can be determined. The first reaction and the second reaction may be conducted reversely or simultaneously or they may be conducted with an interval. The type of the labeling agent and the method of insolubilization may be the same as those mentioned hereinbefore. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used as well.

In the method of measuring the protein, etc. of the present invention by the sandwich method of the present invention, the preferred monoclonal antibodies of the present invention used for the first and the second reactions are antibodies wherein their sites binding to the protein, etc. of the present invention are different from each other. Thus, antibodies used in the first and the second reactions are those wherein, when an antibody used in the second reaction recognizes the C-terminal region of the protein, etc. of the present invention, then another antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a nephrometry. In the competitive method, an antigen in the test liquid and a labeled antigen are allowed to react with an antibody in a competitive manner, then an unreacted labeled antigen (F) and a labeled antigen (B) binding with an antibody are separated (i.e. B/F separation) and the labeled amount of any of B and F is measured whereupon the amount of the antigen in the test liquid is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In the immunometric method, an antigen in the test solution and an immobilized antigen are subjected to a competitive reaction with a certain amount of a labeled antibody followed by separating into solid and liquid phases or the antigen in the test liquid and an excess amount of labeled antibody are allowed to react, then an immobilized antigen is added to bind an unreacted labeled antibody with the solid phase and separated into solid and liquid phases. After that, the labeled amount of any of the phases is measured to determine the antigen amount in the test liquid.

In the nephrometry, the amount of insoluble sediment which is produced as a result of the antigen-antibody reaction in a gel or in a solution is measured. Even when the antigen amount in the test liquid is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein, etc. of the present invention may be constructed taking the technical consideration of persons skilled in the art into consideration in the conventional conditions and operations for each of the methods. With details of those conventional technical means, a variety of reviews, reference books, etc. may be referred to.

They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody of the present invention in the above manner, the protein, etc. of the present invention can be assayed with high sensitivity.

In addition, by quantitative determination of the protein, etc. of the present invention using the antibody of the present invention, various diseases associated with the protein, etc. of the present invention can be diagnozed.

When a decrease in concentration of the protein, etc. of the present invention is detected by determining the concentration of the protein, etc. of the present invention by using the antibody of the present invention, it may lead, with high probability, to the diagnosis of various-diseases such as Alzheimer's diseaseia, Parkinson's disease, Huntington's disease, amyotrophic lateral scleorosis, dementia or cerebellar degeneration.

Thus, the antibody of the present invention is useful as a diagnostic agent for the above-mentioned diseases.

Furthermore, the antibody of the present invention can be used for the purpose of detecting the protein, etc. of the present invention which may be present in test samples such as body fluids or tissues. The antibody can also be used for the construction of an antibody column for purification of the protein, etc. of the present invention, detection of the protein, etc. of the present invention in the fractions in the course of purification, and analysis of the behavior of the protein, etc. of the present invention in the test cell.

(4) Screening for Candidate Medicinal Compounds Against Various Diseases

A compound, or a salt thereof, which promotes the function of the protein, etc. of the present invention, for example, physiological activities such as a nerve-extending or neuro-regenerative activity, a gliacyte stimulating activity and an activity of forming memories in brain, can be used as a therapeutic or prophylactic agent for various diseases such as, for example, Alzheimer's disease, Parkinson's disease, Huntington's disease, amyotrophic lateral sclerosis (ALS), dementia and cerebellar degeneration. Therefore, the protein, etc. of the present invention is useful as a screening reagent for compounds or salts thereof capable of promoting the function of the protein, etc. of the present invention.

The present invention, therefore, further provides a method of screening for a compound capable of promoting the function of the protein, etc. of the present invention (hereinafter sometimes referred to briefly as a promoter of the function of the protein, etc. of the present invention) which comprises using the protein, etc. of the present invention. To be specific, the present invention provides (a) a method for screening for a promoter of the function of the protein, etc. of the present invention which comprises comparing the result in cases that (i) the protein, etc. of the present invention is contacted with a nerve cell or a nerve tissue and (ii) the protein, etc. of the present invention and a test compound are contacted with a nerve cell or a nerve tissue, and (b) a method for screening for a promoter of the function of the protein, etc. of the present invention which comprises comparing the result in cases that (i) the protein, etc. of the present invention is administered to a vertebrate and (ii) the protein, etc. of the present invention and a test compound are administered to a vertebrate.

More specifically, the above screening method (a) comprises assaying the physiological activity, such as a nerve-extending activity or neuroregenerative activity, a gliacyte stimulating activity of the protein, its partial peptide or a salt thereof of the present invention in the above-mentioned cases (i) and (ii) and comparing the results. In the above screening method (b), the activity of forming memories in brain, etc. of the protein, its partial peptide or a salt thereof of the present invention are assayed in the cases (i) and (ii) and the results are compared.

Examples of the nerve cells are neuroblastoma cells, glioma cells, and the corresponding hybrid cells (e.g. N18TG-2, IMR-32, GOTO (e.g. GOTO-P3), NB1, C6BU-1, U251, KNS42, KNS81, NG108-15 cells, and PC-12 cells capable of differentiating into nerves).

Examples of the nerve tissues are mouse neuroepithelial cells, rat hippocampal primary culture cells, mouse embryonic culture Purkinje cells, and mouse dorsal root ganglia, among other cells.

The test compound includes but is not limited to peptides, proteins, non-peptide compounds, synthetic compounds, fermentation products, cell extracts, plant extracts, animal tissue extracts, and blood plasma. The compound may be a novel compound or a known compound.

To carry the screening method (a) into practice, a protein sample is first prepared by dissolving or suspending the protein, its partial peptide or a salt thereof of the present invention (hereinafter sometimes referred to as the protein, etc. of the invention) in a screening buffer. The screening buffer may be any buffer that does not affect the contact of the protein, etc. of the present invention with the nerve cells or nerve tissues (for example, phosphate buffer and Tris-HCl buffer within the pH range of about 4–10 (preferably pH about 6–8). The contact time is generally about 1–10 days and preferably about 7–10 days. The contacting temperature is generally about 37° C.

The nerve-extending or neuro-regenerative activity in the central nerve system or gliacyte stimulating activity of the protein, etc. of the present invention can be assayed by the conventional technique, for example by measuring the elongation of the optic nerve axon or determining the change in intracellular $Ca^{2+}$ concentration.

Thus, the test compound which promotes physiological activities, such as a nerve-extending or neuro-regenerative activity or a gliacyte stimulating activity, by not less than about 20%, preferably not less than about 30%, more preferably not less than about 50%, and most preferably not less than about 70% in case (ii) as compared with case (i) can be selected as a candidate compound which promotes the function of the protein, etc. of the present invention.

To carry the screening method (b) of the present invention into practice, the protein, etc. of the present invention and the test compound are administered to a vertebrate by the intravenous, subcutaneous, intramuscular or oral route. The dosage of the protein, etc. of the present invention for oral administration to human or chimpanzee (body weight 60 kg) is about 0.1 to 100 mg, preferably about 1.0 to 50 mg, and for still better results, about 1.0 to 20 mg per day. The unit dose for parenteral administration is dependent on the subject and method of administration but in the case of an injectable dosage form, it can be administered to human or chimpanzee (body weight 60 kg) with advantage by the intravenous route in a daily dose of about 0.01 to 30 mg, preferably about 0.1 to 20 mg, and more preferably about 0.1 to 10 mg. For animals, the equivalent of the above-mentioned dose per 60 kg body weight can be administered.

The vertebrate includes not only fish (e.g. carp, salmon, herring, trout, goldfish, etc.) but also mammals such as human, mouse, rat, rabbit, sheep, swine, bovine, horse, cat, dog, monkey, chimpanzee, etc.

The activity of forming memories in brain of the protein, etc. of the present invention can be assayed by known methods, for example in accordance with the water maze experiment protocol of Morris (Morris, R. G. M., Journal of Neuroscientific Methods, 11, 47–60 (1984)).

Thus, the test compound which promotes the activity of forming memories in brain by not less than about 20%, preferably not less than 50%, or more preferably not less than 70%, for instance, in case (ii) as compared with case (i) can be selected as a candidate compound which promotes the function of the protein, etc. of the present invention.

The screening kit of the present invention comprises the protein, its partial peptide or a salt thereof of the present invention. The following is an exemplary screening kit of the invention.

Screening Reagents (1) Assay Buffer

Hank's solution (2) Protein Sample

The protein or a salt thereof of the present invention (3) Nerve Cells or Nerve Tissue The nerve cells or nerve tissues as mentioned above which are cultured in a 24-well plate using Eagle's MEM, Hank's solution, etc. at a seeding density of $10^4$ cells/well under 5% carbon dioxide at 37° C.

(4) Detection

Observation under the inverted microscope.

Assay Protocol

The cells with extended neurites per unit field of view in the wells to which the test compound is added are counted and a significance test is made with respect to the number of cells with extended neurites per unit field of view in the control wells to which the test compound is not added.

The compounds and salts thereof obtained by using the above screening method or screening kit of the present invention are compounds selected from the above-mentioned test compounds such as peptides, proteins, non-peptide compounds, synthetic compounds, fermentation products, cell extracts, plant extracts, animal tissue extracts, and blood plasma. The such compounds can promote the function of the protein, etc. of the present invention.

The compound which promotes the function of the protein, etc. of the present invention may by itself promote the function of the protein, etc. of the present invention by showing physiological activities such as a nerve-extending or neuro-regenerative activity or a gliacyte stimulating activity, either additively or synergistically, or even if it does not show the physiological activities by itself, may promote the function of the protein, etc. of the present invention.

The salts of the compound identified by the screening method as mentioned above includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfonic acid, etc.) and salts thereof with organic acids (e.g. acetic acid, formic acid, propionic acid, fumaric acid, maleic acid, succinic acid, tartaric acid, citric acid, maleic acid, oxalic acid, benzoic acid, methanesulfonic acid or benzenesulfonic acid, etc.)

The compound which promotes the function of the protein, etc. of the present invention or a salt thereof is useful as a safe therapeutic or prophylactic agent of low toxicity for a variety of diseases such as Alzheimer's disease, Parkinson's disease, Huntington's disease, amyotrophic lateral sclerosis (ALS), dementia, and cerebellar degeneration.

When the compound obtained by using the screening method or the screening kit of the present invention is used as the therapeutic or prophylactic agent, it can be used in accordance with the conventional method.

For example, the compound can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by the mixing compound or a salt thereof with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained. These tablets, capsules, elixirs, microcapsules and injectable preparations may be the same as the therapeutic or prophylactic agent comprising the protein, etc. of the present invention as mentioned above.

Because the thus-obtained preparation is safe and of low toxicity, it can be administered to mammals (e.g., human, mouse, rat, rabbit, sheep, pig, bovine, horse, cat, dog, monkey, chimpanzee, etc.).

The dose of the compound obtained by the screening method may vary depending on subject of disease, subject of administration, way of administration, and so on.

When the compound is used, for example, for treating Alzheimer's disease by oral administration, the dose of the compound is normally about 0.1 to 100 mg, preferably 1.0 to 50 mg, and more preferably 1.0 to 20 mg per day for an adult human (weighing 60 kg). When the compound is used, for example, for treating Alzheimer's disease by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject of disease and so on. For other animal species, corresponding, doses as converted per 60 kg weight can be administered.

(6) The Oligonucleotide or a Derivative Thereof

The oligonucleotide or a derivative thereof which is capable of complementary binding to the DNA or mRNA coding for the protein, etc. of the present invention and promotes the expression of the DNA, the mRNA or the protein, etc. of the present invention is capable of promoting the function of the protein, etc. of the present invention in vivo. Therefore, the oligonucleotide or a derivative thereof is used for a prophylactic or therapeutic agent for various diseases such as Alzheimer's disease, Parkinson's disease, Huntington's disease, amyotrophic lateral scleorosis, dementia and cerebellar degeneration.

When the oligonucleotide or a derivative thereof is used for the prophylactic or therapeutic composition as mentioned above, it can be formulated in the same way as the prophylactic or therapeutic agent containing the protein or the DNA of the present invention and can be administered to mammals.

Because the thus-obtained preparation is safe and of low toxicity, it can be administered to mammals (e.g., human, mouse, rat, rabbit, sheep, pig, bovine, horse, cat, dog, monkey, chimpanzee, etc.).

The DNA may be used alone or after inserting it into a suitable vector such as retrovirus vector, adenovirus vector, adenovirus-associated virus vector, pox virus etc. followed by administering the product vector to a mammal by a conventional means. The oligonucleotide or a derivative thereof can also be administered oligonucleotide or a derivative thereof with physiologically acceptable carriers such as adjuvants to assist in uptake, by "gene" gun or by a catheter such as a catheter with a hydrogel.

In addition, the oligonucleotide or a derivative thereof can be used as a diagnostic oligonucleotide probe for investigating the presence of the DNA of the present invention or the status of its expression in various tissues and cells.

(6) Construction of a Transgenic Non-human Animal Containing the DNA Coding for the Protein of the Present Invention The transgenic non-human animals which express the protein, etc. of the present invention can be prepared by using the DNA of the present invention.

The non-human animal (hereinafter referred to as animal) includes mammals such as rats, mice, rabbits, sheep, pigs, bovines, cats, dogs, monkeys and so on.

For transfer of the DNA of the present invention to the host animal, it is generally advantageous to use a gene construct prepared by linking the DNA at downstream of a promoter capable of being expressed in animal cells. For example, in transferring the mice-derived DNA of the present invention, it can be linked at downstream of a promoter, which is capable of causing expression of the DNA of the present invention in various animals and is derived from animals having high homology to mice, to prepare a gene construct which can then be microinjected into the fertilized egg cell of mice, whereby a DNA transferred animal showing a high production of the protein of the present invention can be provided.

As the promoter, promoters derived from viruses, ubiquitous expression promoters such as metallothionein, etc. can be used.

Transfering the DNA of the present invention at the fertilized egg cell stage, the DNA can be ubiquitous in all the germ cells and somatic cells of the host animal. The presence of the protein, etc. of the present invention in the germ cells of the transgenic animal following DNA transfer means that all the germ cells and somatic cells of all the progeny of the transgenic animal harbor the protein, etc. of the present invention. Thus, the offspring of animals of this line to which gene is passed down have the protein, etc. of the present invention in their germ cells and somatic cells.

The animal to which the DNA of the present invention has been transferred can be verified by mating to retain the gene stably and then bred as an animal harboring the DNA from generation to generation under the usual breeding conditions. By acquiring homozygous animals having the transferred gene in both homologous chromosomes and mating the animals of both sexes, they can be bred serially so that all the progeny may harbor the DNA.

Since the animal to which the DNA of the present invention is transferred shows a high expression of the protein, etc. of the present invention, it is useful as an animal for screening for compounds promoting the function of the protein, etc. of the present invention.

As other potential uses for transgenic animals harboring the DNA of the present invention, the following uses can be suggested.

(a) Use as a cell source for tissue culture;
 (b) Analysis of the relationship of the protein, etc. of the present invention to proteins which are specifically expressed or activated by the protein by direct analysis of DNAs or RNAs in the tissues of the transgenic animal harboring the DNA of the present invention or analysis of the composition of the protein expressed by the DNA;
 (c) Study of the functions of cells established from tissues such as brain or peripheral tissues which are generally difficult to culture in the standard tissue culture technique by introducing the DNA into them;
 (d) Screening of drugs capable of enhancing the cell functions by using the cells described in (c);
 (e) Isolation and purification of the muteins of the present invention from cell lines showing a high expression the protein, etc.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid Substitution groups, protecting groups and reagents used in the specification of the present application are represented by the symbols set forth below.

Me: Methyl
Et: Ethyl
Bu: Butyl
Ph: Phenyl
TC: Thiazolidine-4(R)-carboxamide
Tos: p-toluene sulfonyl
CHO: Formyl
Bzl: Benzyl
$Cl_2$-Bzl: 2,6-dichlorobenzyl
Bom: Benzyloxymethyl
Z: Benzyloxycarbonyl
Br-Z: 2-bromobenzyloxycarbonyl
Cl-Z: 2-chlorobenzyloxycarbonyl
Boc: Tert-butoxycarbonyl
DNP: Dinitrophenyl
Trt: Trityl
Bum: Tert-butoxymethyl
Fmoc: N-9-fluorenylmethyloxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboximide
DCC: Dicyclohexylcarbodiimide SEQ ID NOs of the SEQUENCE LIST in the specification show the following sequences.

SEQ ID NO:1 shows an amino acid sequence of the mature human ependymin-like protein of the present invention.

SEQ ID NO:2 shows an amino acid sequence of the mature rat ependymin-like protein of the present invention.

SEQ ID NO:3 shows an amino acid sequence of the mature mouse ependymin-like protein of the present invention.

SEQ ID NO: 4 shows a common amino acid sequence between the human ependymin-like protein, rat ependymin-like protein and mouse ependymin-like protein of the present invention.

SEQ ID NO:5 shows a common amino acid sequence between the human ependymin-like protein, rat ependymin-like protein and mouse ependymin-like protein of the present invention.

SEQ ID NO:6 shows a common amino acid sequence between the human ependymin-like protein, rat ependymin-like protein and mouse ependymin-like protein of the present invention.

SEQ ID NO:7 shows a common amino acid sequence between the human ependymin-like protein, rat ependymin-like protein and mouse ependymin-like protein of the present invention.

SEQ ID NO:8 shows a common amino acid sequence between the human ependymin-like protein and rat ependymin-like protein of the present invention.

SEQ ID NO:9 shows a common amino acid sequence between the human ependymin-like protein and rat ependymin-like protein of the present invention.

SEQ ID NO:10 shows an amino acid sequence of the precursor protein of human ependymin-like protein of the present invention.

SEQ ID NO:11 shows an amino acid sequence of the precursor protein of human ependymin-like protein of the present invention.

SEQ ID NO:12 shows an amino acid sequence of the precursor protein of rat ependymin-like protein of the present invention.

SEQ ID NO:13 shows an amino acid sequence of the precursor protein of mouse ependymin-like protein of the present invention.

SEQ ID NO:14 shows an amino acid sequence of the signal peptide of human ependymin-like protein of the present invention.

SEQ ID NO:15 shows an amino acid sequence of the signal peptide of human ependymin-like protein of the present invention.

SEQ ID NO:16 shows an amino acid sequence of the signal peptide of rat ependymin-like protein of the present invention.

SEQ ID NO:17 shows an amino acid sequence of the signal peptide of mouse ependymin-like protein of the present invention.

SEQ ID NO:18 shows a nucleotide sequence of the DNA coding for the human ependymin-like protein having an amino acid sequence represented by SEQ ID NO:1 of the present invention.

SEQ ID NO:19 shows a nucleotide sequence of the DNA coding for the rat ependymin-like protein having an amino acid sequence represented by SEQ ID NO:2 of the present invention.

SEQ ID NO:20 shows a nucleotide sequence of the DNA coding for the mouse ependymin-like protein having an amino acid sequence represented by SEQ ID NO:3 of the present invention.

SEQ ID NO:21 shows a nucleotide sequence of the DNA coding for the common amino acid sequence, which is represented by SEQ ID NO:4, between the human ependymin-like protein, rat ependymin-like protein and mouse ependymin-like protein of the present invention.

SEQ ID NO:22 shows a nucleotide sequence of the DNA coding for the common amino acid sequence, which is represented by SEQ ID NO:5, between the human ependymin-like protein, rat ependymin-like protein and mouse ependymin-like protein of the present invention.

SEQ ID NO:23 shows a nucleotide sequence of the DNA coding for the common amino acid sequence, which is represented by SEQ ID NO:6, between the human ependymin-like protein, rat ependymin-like protein and mouse ependymin-like protein of the present invention.

SEQ ID NO:24 shows a nucleotide sequence of the DNA coding for the common amino acid sequence, which is represented by SEQ ID NO:7, between the human ependymin-like protein, rat ependymin-like protein and mouse ependymin-like protein of the present invention.

SEQ ID NO:25 shows a nucleotide sequence of the DNA coding for the common amino acid sequence, which is represented by SEQ ID NO:8, between the human ependymin-like protein and rat ependymin-like protein of the present invention.

SEQ ID NO:26 shows a nucleotide sequence of the DNA coding for the common amino acid sequence, which is represented by SEQ ID NO:9, between the human ependymin-like protein and rat ependymin-like protein of the present invention.

SEQ ID NO:27 shows a nucleotide sequence of the DNA coding for the precursor protein having an amino acid sequence represented by SEQ ID NO:10 of the human ependymin-like protein of the present invention.

SEQ ID NO:28 shows a nucleotide sequence of the DNA coding for the precursor protein having an amino acid sequence represented by SEQ ID NO:11 of the human ependymin-like protein of the present invention.

SEQ ID NO:29 shows a nucleotide sequence of the DNA coding for the precursor protein having an amino acid sequence represented by SEQ ID NO:12 of the rat ependymin-like protein of the present invention.

SEQ ID NO:30 shows a nucleotide sequence of the DNA coding for the precursor protein having an amino acid sequence represented by SEQ ID NO:13 of the mouse ependymin-like protein of the present invention.

SEQ ID NO:31 shows a nucleotide sequence of the DNA coding for the signal peptide, which has an amino acid sequence represented by SEQ ID NO:14, of the human ependymin-like protein of the present invention.

SEQ ID NO:32 shows a nucleotide sequence of the DNA coding for the signal peptide, which has an amino acid sequence represented by SEQ ID NO:15, of the human ependymin-like protein of the present invention.

SEQ ID NO:33 shows a nucleotide sequence of the DNA coding for the signal peptide, which has an amino acid sequence represented by SEQ ID NO:16, of the rat ependymin-like protein of the present invention.

SEQ ID NO:34 shows a nucleotide sequence of the DNA coding for the signal peptide, which has an amino acid sequence represented by SEQ ID NO:17, of the mouse ependymin-like protein of the present invention.

SEQ ID NO:35 shows a nucleotide sequence of the probe used for cloning the DNA coding for the human ependymin-like protein of the present invention in Example 1.

The transformant strain of *Escherichia coli*, designated XL1-Blue/phEDN1-95, which was obtained in the Reference Example 1 mentioned hereinafter, is on deposit under the terms of the Budapest Treaty from Aug. 28, 1996, with the National Institute of Bioscience and Human-Technology, Agency of Industrial Science and Technology, JAPAN (NIBH) under the Accession Number of FERM BP-5640. They are also on deposit from Sep. 2, 1996 with the IFO under the Accession Number of IFO 16011.

The transformant strain of *Escherichia coli*, designated SURE/prEDN91-6, which was obtained in the Example 3 mentioned hereinafter, is on deposit under the terms of the Budapest Treaty from Nov. 28, 1996, with the NIBH under the Accession Number of FERM BP-5759. It is also on deposit from September 2, 1996 with the IFO under the Accession Number of IFO 16053.

The transformant strain of *Escherichia coli*, designated SURE/pmEDN78-13, which was obtained in the Example 5 mentioned hereinafter, is on deposit under the terms of the Budapest Treaty from May 20, 1997, with the NIBH under the Accession Number of FERM BP-5949. It is also on deposit from Jun. 4, 1997 with the IFO under the Accession Number of IFO 16090.

BRIEF DESCRIPTION OF THE DRAWINGS

FIGS. 1A–D shows the nucleotide sequence of the DNA coding for the human ependymin-like protein of the present invention obtained in Example 1 (SEQ ID NO:28) and the amino acid sequence encoded thereby (SEQ ID NO:11). The arrow indicates the signal peptide cleavage site. The region surrounded by a square indicates the N-glycosylation site. The underlines indicate the ATTTA sequence associated with the lability of the mRNA and the poly(A)$^+$ addition signal, respectively.

FIGS. 2A–C shows the nucleotide sequence of the DNA coding for the rat ependymin-like protein of the present invention obtained in Example 3 (SEQ ID NO:29) and the amino acid sequence encoded thereby (SEQ ID NO:12). The arrow indicates the signal peptide cleavage site. The region surrounded by a square indicates the N-glycosylation site. The underline indicates the poly(A)$^+$ addition signal.

FIGS. 3A–D shows the nucleotide sequence of the DNA coding for the mouse ependymin-like protein of the present invention obtained in Example 5 (SEQ ID NO:30) and the amino acid sequence encoded thereby (SEQ ID NO:13). The arrow indicates the signal peptide cleavage site. The region surrounded by a square indicates the N-glycosylation site. The underline indicates the poly(A)$^+$addition signal.

FIG. 4 is a comparative diagram of the amino acid sequence of the human ependymin-like protein of the present invention obtained in Example 1 (SEQ ID NO:11), the amino acid sequence of the rat ependymin protein of the present invention obtained in Example 3 (SEQ ID NO:12), and the amino acid sequence of the mouse ependymin-like protein of the present invention obtained in Example 5 (SEQ ID NO:13). (1) represents the amino acid sequence of the human ependymin-like protein of the present invention (SEQ ID NO:11), (2) represents the amino acid sequence of the rat ependymin-like protein of the present invention (SEQ ID NO:12), and (3) represents the amino acid sequence of the mouse ependymin-like protein of the present invention (SEQ ID NO:13). The shaded area represents the amino acid residues showing the amino acid residues homologous among the human ependymin-like protein, rat ependymin-like protein and mouse ependymin-like protein.

FIG. 5 is a comparative diagram of the amino acid sequence of the human ependymin-like protein of the present invention obtained in Example 1 (SEQ ID NO:11) and the amino acid sequence of the rat ependymin protein of the present invention obtained in Example 3 (SEQ ID NO:12). (1) represents the amino acid sequence of the human ependymin-like protein of the present invention (SEQ ID NO:11) and (2) represents the amino acid sequence of the rat ependymin-like protein of the present invention (SEQ ID NO:12). The shaded area represents the amino acid residues homologous between the human ependymin-like protein and rat ependymin-like protein.

BEST MODE FOR CARRYING OUT THE INVENTION

EXAMPLES

Figure 6:
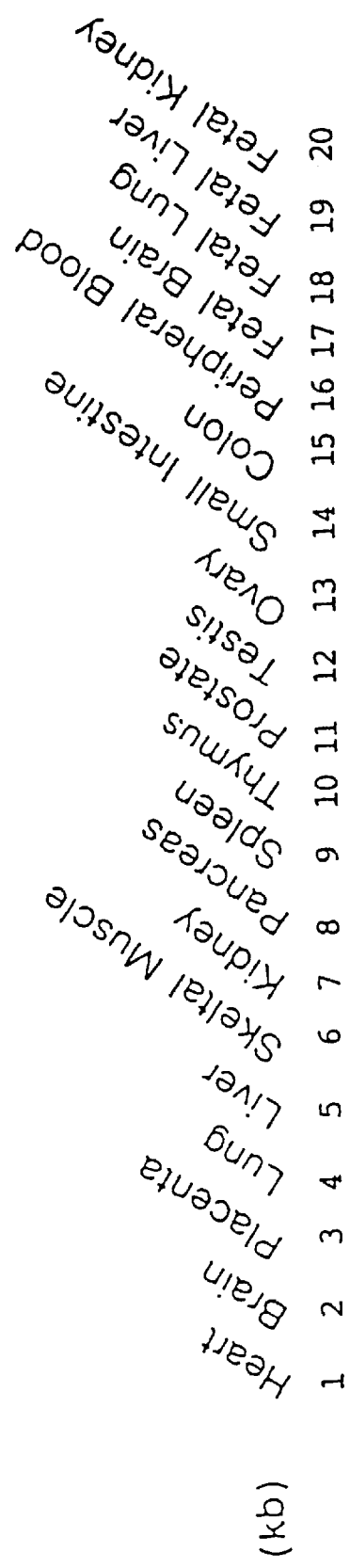
FIG. 6 shows the amounts of expression of the mRNA coding for the human ependymin-like protein of the present invention in various tissues as determined by the Northern hybridization method (electrophoregram), where (1) represents heart, (2) brain, (3) placenta, (4) lung, (5) liver, (6) skeletal muscle, (7) kidney, (8) pancreas, (9) spleen, (10) thymus, (11) prostate, (12) testis, (13) ovary, (14) small intestine, (15) colon, (16) peripheral white blood cell, (17) fetal brain, (18) fetal lung, (19) fetal liver and (20) fetal kidney. The figure (kb) at left indicates the size of the RNA molecular mass marker.

The following examples are intended to describe the present invention in further detail and should by no means be interpreted as defining the scope of the present invention. The gene manipulation using *Escherichia coli* was carried out in accordance with the procedure described in Molecular Cloning 2nd (J. Sambrook et al., Cold Spring Harbor Lab. Press, 1989).

Example 1

Cloning of the cDNA Coding for Human Ependymin-like Protein

From 5 µg of human placental poly(A)$^+$RNA (Clontech), a first strand DNA was synthesized using an oligo(dT)

primer having XhoI site at a terminus and SuperScript II MMLV RNase H⁻ reverse transcriptase (Gibco BRL). Then, using E. coli DNA polymerase I and RNase H, a second strand was synthesized. In this manner, a double-stranded cDNA was obtained from the poly(A)⁺RNA. This double-stranded DNA was treated with Pfu DNA polymerase (Stratagene) to provide blunt ends and an EcoRI adapter was added. This double-stranded DNA with the EcoRI adapter added to either end was subjected to gel filtration to remove cDNAs about 1000 bp and less and using T4 polynucleotide kinase (Takara Shuzo), the EcoRI adapters were phosphorylated. This cDNA was then digested with XhoI, and after integration with λZAPII EcoRI-XhoI arm (Stratagene), in vitro packaging was carried out to construct a human placental cDNA library of about 2.1×10⁷ pfu as a whole (insertion rate≧99%). The λ phage of a cDNA library of about 3.0×10⁶ pfu was used to infect E. coli XL1-Blue MRF' and about 2.5×10⁴ plaques per plate were seeded on soft agar plates and incubated at 37° C. overnight. The resulting plaques were transferred onto a nylon membrane filter (Hybond N. Amersham) and treated with denaturating solution (0.5 N sodium hydroxide, 1.5 M sodium chloride) and neutralizing solution (0.5 M Tris-HCl (pH 7.0), 1.5 M sodium chloride), and 2×SSC (20×SSC=3 M sodium chloride, 0.3 M sodium citrate) in the order mentioned, air-dried, and irradiated with ultraviolet light to fix the phage DNA on the nylon membrane filter.

On the other hand, as a probe, an oligonucleotide having the nucleotide sequence of SEQ ID NO:35 was labeled using [γ-³⁵P]ATP (DuPont) and T4 polynucleotide kinase (Takara Shuzo). Hybridization was carried out at 65° C. in a hybridization buffer (5×SSPE (20×SSPE=3.6 M sodium chloride, 0.2 M sodium phosphate (pH 7.7), 20 mM EDTA), 5×Denhardt's solution, 100 μg/ml heat-denatured salmon sperm DNA, 0.1% SDS) containing the labeled probe. The filter was finally rinsed in 0.1×SSC-0.1% SDS solution at 50° C. and an autoradiogram was prepared to detect the plaques hybridizing with the probe.

The above procedure was repeated for purification to the single clone stage and 8 phage clones, namely phage clones λhEDN 59, 64, 82, 90, 91, 95, 99–2, and 112, were infected with helper phage and excised in vivo. The plasmids with the cDNA fragment inserted in the EcoRI-XhoI site of pbluescript SK (−) were recovered in E. coli SOLR to provide phEDN1–59, –64, –82, –90, –91, –95, –99-2, and –112, respectively. After cultivation of E. coli SOLR harboring each of those plasmids, the plasmid DNA was purified using QIAGEN Plasmid Mini Kit (Qiagen) and the sequencing reaction was carried out using DNA Sequencing Kit (Perkin-Elmer). The base sequence of the inserted cDNA fragment was determined using DNA Sequencer 377 (Perkin-Elmer). phEDN1–95, among them, had a 2507 bp cDNA fragment containing the poly(A)⁺ chain (FIG. 1), and a novel 224-residue protein containing a signal peptide consisting of 24 or 37 amino acid residues was encoded in this cDNA fragment. In addition, this protein had two N-glycosylation sites. This protein had moderate homology with ependymin occurring in the brain of bony fish, with 23.6% homology with rainbow trout ependymin. Furthermore, all the four cysteine residues conserved in ependymins were found conserved in this protein, indicating that it was human ependymin-like protein. On the other hand, the cDNA inserted in phEDN1-99-2 among the clones sequenced above showed a silent substitution of one base from ¹⁹⁰Arg (CGG) to Arg (CGT), suggesting the existence of polymorphism in respect of this base.

The plasmid phEDN1–95 containing the DNA coding for human ependymin-like protein according to the present invention was introduced into Escherichia coli XL1-Blue to provide a transformant, namely E. coli XL1-Blue/phEDN1–95.

Example 2

Northern Hybridization of Human Tissues

A membrane filter (MTN blot, Clonetech) preblotted with 2 μg of human tissue poly(A)⁺RNA was subjected to prehybridization in a hybridization buffer (50% formamide, 5×SSPE (20×SSPE=3.6 M sodium chloride, 0.2 M sodium phosphate (pH 7.7), 20 mM EDTA), 5×Denhardt's solution, 0.1% SDS, 100 μg/ml heat-denatured salmon sperm DNA) at 42° C.

On the other hand, the BamHI-SpeI 383 bp cDNA fragment of the cDNA coding for human ependymin-like protein as shown in FIG. 1 (the cDNA fragment having a nucleotide sequence of bases no. 643 to no. 1025 of the base sequence shown in FIG. 1), as a probe, was labeled with [α-³²P]dCTP (DuPont) using Randam Primer Labeling Kit (Amersham). After 12 hours of prehybridization in a hybridization buffer (50% formamide, 5×SSPE, 5×Denhardt's solution, 0.1% SDS, 100 μg/ml heat-denatured salmon sperm DNA) at 42° C., hybridization was carried out in a hybridization buffer (50% formamide, 5×SSPE, 5×Denhardt's solution, 0.1% SDS, 100 μg/ml heat-denatured salmon sperm DNA) containing the labeled probe at 42° C. for 18 hours. The filter was finally rinsed with 0.1×SSC (20×SSC=3 M sodium chloride, 0.3 M sodium citrate)–0.1% SDS at 55° C. and an autoradiogram was prepared to detect a band hybridizing with the probe. As a result, the molecular mass of the mRNA coding for this protein was about 2.5 kb and the amount of its expression was largest in the skeletal muscle, heart, and brain and slightly less in the prostate, ovary, and testis. In the kidney, its expression was found in fetuses as well (FIG. 6).

Example 3

Cloning of cDNA Encoding Rat Ependymin-like Protein

From 8-week-old male Sprague-Dawley rats, the whole brain was enucleated and the total RNA was prepared by the guanidine-isothiocyanate method. Then, using the oligo(dT) span column (Pharmacia), a poly(A)⁺RNA fraction was obtained from the total RNA prepared above. From 5 μg of this poly(A)⁺RNA, a first strand DNA was synthesized using NotI site-terminated an oligo(dT) primer having NotI site at a terminus and Superscript II MMLV RNase H⁻ reverse transcriptase (Gibco BRL). Then, using E. coli DNA polymerase I, E. coli DNA ligase, and RNase H, a second strand DNA was synthesized to provide a double-stranded cDNA from the poly(A)⁺RNA. This double-stranded DNA was treated with T4 DNA polymerase (Gibco BRL) to prepare blunt ends and an SalI adapter was added. This double-stranded DNA with the SalI adapter added to either end was cut with NotI and subjected to gel filtration to remove cDNAs of about 1000 bp and less. After integration with λgt22A SalI-NotI arm (Gibco BRL), in vitro packaging was carried out to construct a rat brain cDNA library of about 3.4×10⁶ pfu as a whole (insertion rate≧99%). The λ phage of a cDNA library of about 2.2×10⁶ pfu was used to infect E. coli Y1090r⁻ and about 2.2×10⁴ plaques per plate were seeded on soft agar plates and incubated at 37° C. overnight. The resulting plaques were transferred onto a nylon membrane filter (Hybond N, Amersham) and treated serially with denaturing solution (0.5 N sodium hydroxide, 1.5 M sodium chloride), neutralizing solution (0.5 M Tris-HCl (pH 7.0), 1.5 M sodium chloride), and 2×SSC (20×SSC=3M sodium chloride, 0.3 M sodium citrate). The filter was air-dried and irradiated with ultraviolet light to fix the phage DNA on the nylon membrane filter.

On the other hand, as a probe, the BamHI-SpeI 383 bp cDNA fragment of the cDNA coding for human ependymin-like protein as shown in FIG. 1 (the cDNA fragment having a nucleotide sequence of bases no. 643 to no. 1025 of the nucleotide sequence shown in FIG. 1) was labeled with [α-$^{32}$P]dCTP (DuPont) using Random Primer Labeling Kit (Amersham). Hybridization was carried out in a hybridization buffer (5×SSPE, 5×Denhardt's solution, 100 μg/ml heat-denatured salmon sperm DNA, 0.1% SDS) containing the labeled probe at 65° C. The filter was finally rinsed with 2×SSC-0.1% SDS solution at 60° C. and an autoradiogram was prepared to detect plaques hybridizing with the probe.

The above procedure was repeated for purification to the single clone stage and the phage DNA was extracted from each of 5 clones, namely phage clones λrEDN 8, 56, 88, 91, and 100. After cleavage with restriction enzymes SalI and NotI, the cDNA fragment was inserted into the SalI-NotI site of pGEM11Zf(−) to provide prEDN 8, 56, 88, 91-6, and 100, respectively. The E. coli DH10B harboring each of those plasmids was cultured and using QIAGEN Plasmid Mini Kit (Qiagen), the plasmid DNA was purified. The sequencing reaction was carried out using DNA Sequencing Kit (Perkin-Elmer) and the base sequence of the inserted cDNA fragment was determined using DNA Sequencer 377 (Perkin-Elmer). Among the above plasmids, prEDN91-6 had a 2202 bp cDNA fragment containing the poly(A)$^+$ chain (FIG. 2). Encoded in this cDNA fragment was a 224-residue rat ependymin-like protein containing a signal peptide consisting of 33 or 34 amino acids, with three N-glycosylation sites. The amino acid sequence of the rat ependymin-like protein had 74.6% homology with human ependymin-like protein, and all the cysteine residue sites in the mature region were conserved.

The plasmid prEDN91-6 containing the DNA coding for rat ependymin-like protein according to the present invention was introduced into *Escherichia coli* SURE to provide a transformant, namely E. coli SURE/prEDN91-6.

Example 4

Northern Hybridization of Rat Tissues

From 8-week-old Sprague-Dawley rats (Charles River Japan), various tissues (brain, spine, heart, liver, spleen, stomach, small intestine, testis, ovary, placenta) were isolated and the total RNA was prepared by the guanidine-thiocyanate method. This total RNA was subjected to an oligo(dT) span column (Pharmacia) to prepare a poly(A)$^+$ RNA. This poly(A)$^+$RNA, 2.5 μg, was subjected to 1.2% formalin-modified agarose gel electrophoresis and blotted on a nylon membrane filter (Biodyne B, Nippon Pall) by capillary blotting for 16 hours. This nylon membrane filter was treated with ultraviolet light to fix the blotted RNA and prehybridization was carried out in a hybridization buffer (50% formamide, 5×SSPE (20×SSPE=3.6 M sodium chloride, 0.2 M sodium phosphate (pH 7.7), 20 mM EDTA), 5×Denhardt's solution, 0.1% SDS, 100 μg/ml heat-denatured salmon sperm DNA) at 42° C.

Figure 7:
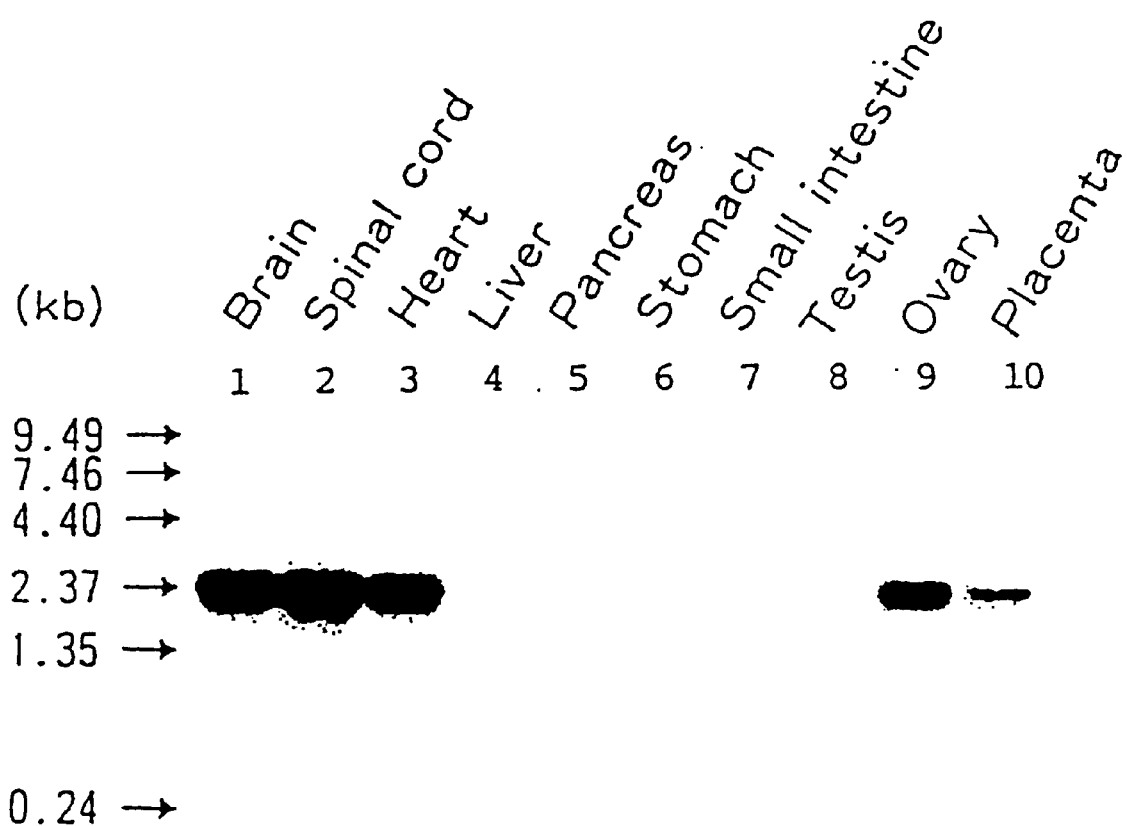
FIG. 7 shows the amounts of expression of the mRNA coding for the rat ependymin-like protein of the present invention in various tissues as determined by the Northern hybridization method (electrophoregram), where (1) represents brain, (2) spinal cord, (3) heart, (4) liver, (5) pancreas, (6) stomach, (7) small intestine, (8) testis, (9) ovary and (10) placenta. The figure (kb) at left indicates the size of the RNA molecular mass marker.

On the other hand, as a probe, an Eco47III-PstI 1025 bp cDNA fragment of the cDNA coding for rat ependymin-like protein as shown in FIG. 2 (the cDNA fragment having a nucleotide sequence of bases no. 111 to no. 1135 of the nucleotide sequence shown in FIG. 2) was labeled with [α-$^{32}$P]dCTP using Random Primer Labeling Kit (Amersham). Hybridization was carried out in hybridization buffer (50% formamide, 5×SSPE, 5×Denhardt's solution, 0.5% SDS, 100 μg/ml heat-denatured salmon sperm DNA) containing the labeled probe at 42° C. for 16 hours. The filter was finally rinsed with 0.1×SSC-0.1% SDS solution at 50° C. and an autoradiogram was prepared to detect the band hybridizing with the probe (FIG. 7). As a result, an mRNA with a mass of about 2.4 kb was found to have been expressed abundantly in the brain, spinal cord, and heart and moderately in the ovary and in the placenta at 17.5 days after conception as well.

Example 5

Cloning of cDNA Encoding Mouse Ependymin-like Protein

Eight-week-old male C57 BL/6N mice (Charles River Japan) were sacrificed by decapitation. The spinal cord was isolated and the total RNA was prepared by the acid-phenol guanidine chloroform method. From this total RNA, a poly(A) RNA fraction was prepared using an oligo(dT) cellulose column (Pharmacia). From 5 μg of this poly(A)$^+$ RNA, a first strand DNA was synthesized by using an oligo (dt) primer having XhoI site at a terminus and SuperScript II MMLV RNase H$^-$ reverse transcriptase (Gibco BRL) and, then, a second strand DNA was synthesized by using E. coli DNA polymerase I and RNase H to construct a double-stranded cDNA from the poly(A)$^+$RNA. This double-stranded DNA was treated with pfu DNA polymerase (Stratagene) to provide blunt ends and an EcoRI adapter was added. Then, the EcoRI adapter at either end of this double-stranded DNA was phosphorylated by using T4 polynucleotide kinase (Takara Shuzo). This cDNA was digested with XhoI, subjected to gel filtration to remove cDNA of about 400 bp and less, and integrated with λZAPII EcoRI-XhoI arm (Stratagene). This recombinant phage DNA was subjected to in vitro packaging to construct a mouse spinal cord cDNA library of about 2.9×10$^6$ pfu as a whole (insertion rate≧99%). The λ phage of this cDNA library was used to infect E. coli XL 1-Blue MRF' and about 2.7×10$^4$ plaques per plate were seed on soft agar plates and incubated at 37° C. overnight for plaque formation. The resulting plaques were transferred onto a nylon membrane filter (Hybond N$^+$, Amersham) and treated serially with denaturing solution (0.5 N sodium hydroxide, 1.5 M sodium chloride), neutralizing solution (0.5 M Tris-HCl (pH 7.0), 1.5 M sodium chloride), and 2×SSC (20×SSC=3 M sodium chloride, 0.3 M sodium citrate). After air-drying, the filter was irradiated with ultraviolet light to fix the phage DNA on the nylon membrane filter.

On the other hand, as a probe, the Eco47III-PstI 1025 bp cDNA fragment of the cDNA coding for rat ependymin-like protein as shown in FIG. 2 (the cDNA fragment having a nucleotide sequence of bases no. 111 to no. 1135 of the nucleotide sequence shown in FIG. 2) was labeled using [α-$^{32}$P]dCTP (DuPont) and Random Primer Labeling Kit (Amersham). Hybridization was carried out in a hybridization buffer (5×SSPE, 5×Denhardt's solution, 100 μg/ml heat-denatured salmon sperm DNA, 0.5% SDS) containing the labeled proble at 65° C. The filter was finally rinsed with 0.2×SSC-0.1% SDS solution at 50° C. and an autoradiogram was prepared to detect plaques hybridizing with the probe.

The above procedure was repeated for purification to the single clone stage and the resultant 15 phage clones λmEDN 4, 8, 30, 32, 47, 51, 59, 66, 68, 77, 78, 81, 85, 98, and 99 were respectively infected with the helper phage and subjected to in vivo excision, whereby the plasmids carrying the cDNA fragment inserted in the EcoRI-XhoI site of pBluescript SK(-), namely pmEDN4-1, 8-1, 30-3, 32-5, 47-3, 51-5, 59-7, 66-7, 68-9, 77-11, 78-13, 81-15, 85-9, 98-17, and 99-19, were recovered in *Escherichia coli* XLOLR. The *E. coli* XLOLR strains harboring pmEDN4-1, 8-1, 32-5, 47-3, 59-7, 66-7, 68-9, 77-11, 78-13, 81-15, and 99-19, respectively, among the above plasmids, were cultured and using QIAGEN Plasmid Mini Kit (QIAGEN), plasmid DNAs were purified. The sequencing reaction was carried out using Perkin-Elmer DNA Sequencing Kit (Perkin-Elmer) and the base sequence of the inserted cDNA fragment was determined by using DNA Sequencer 377 (Perkin-Elmer). Among the above plasmids, pmEDN78-13 had a 2403 bp cDNA fragment (SEQ ID NO: FIG. 3) containing a poly(A) chain, and a 224-residue mouse ependymin-like protein containing a signal peptide consisting of 30 or 37 amino acids had been encoded in this cDNA fragment.

On the other hand, among the clones determined for base sequence, pmEDN32-5, 47-3, 77-11, 78-13, 81-15, and 99-19 had the poly(A)$^+$ chain added in the same position as pmEDN78-13 but pmEDN4-1, 8-1, 59-7, 66-7, and 68-9 had a cDNA fragment retrenched in the 3' nontranslation region by 113 bp by recognizing the poly(A)$^+$ addition signal upstream of that in the case of pmEDN78-13.

The amino acid sequence of mouse ependymin-like protein was 91.1% homologous with the amino acid sequence of rat ependymin-like protein and 74.4% homologous with that of human ependymin-like protein, and the cysteine residue sites in the mature region and two N-glycosylation sites were all conserved.

The plasmid pmEDN78-13 containing the DNA coding for mouse ependymin-like protein according to the present invention was introduced into *Escherichia coli* SURE to provide a transformant, namely *E. coli* SURE/pmEDN78-13.

Example 6

Northern Hybridization of Mouse Tissues

Figure 8:
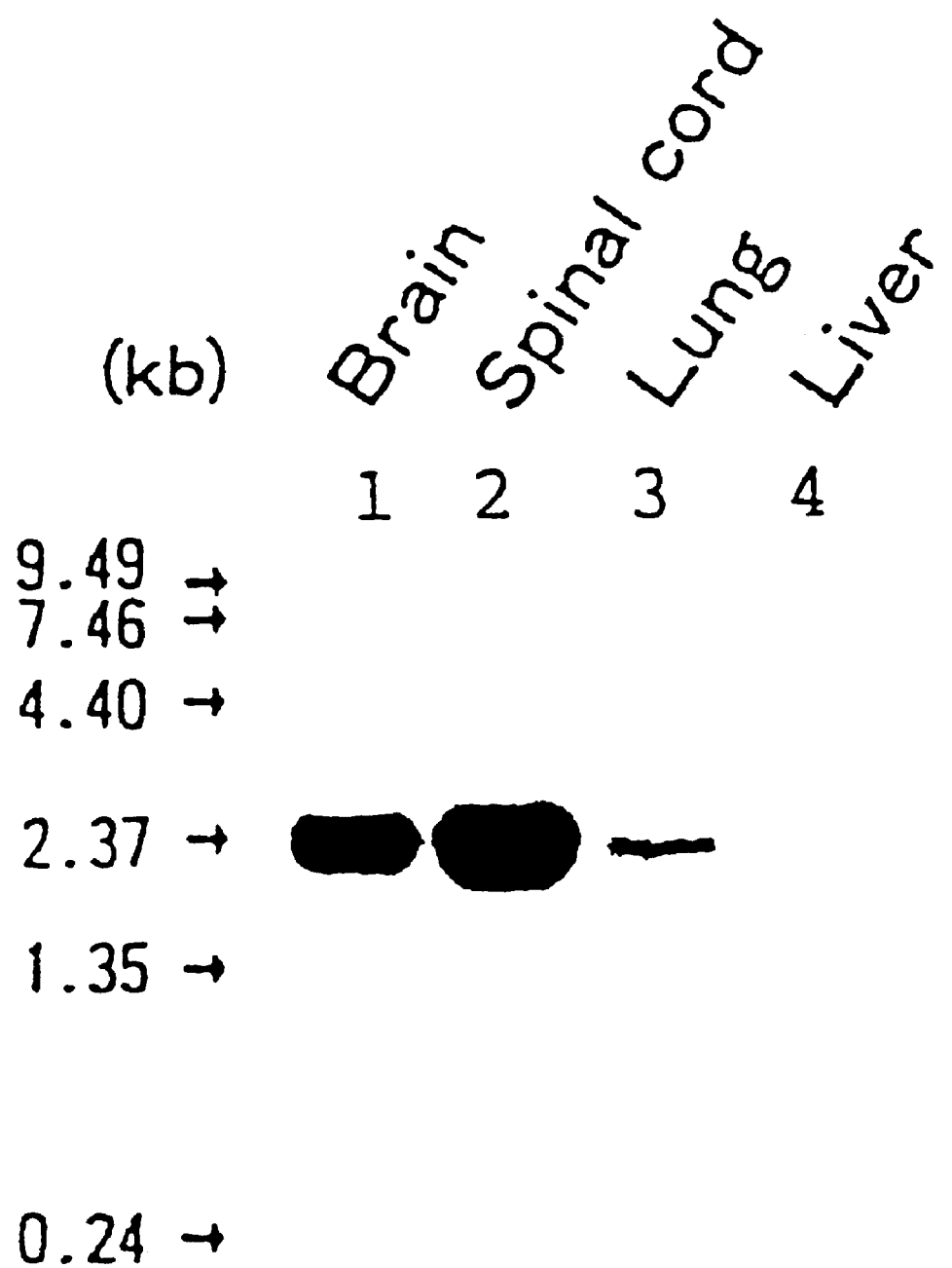
FIG. 8 shows the amounts of expression of the mRNA coding for the mouse ependymin-like protein of the present invention in various tissues as determined by the Northern hybridization method (electrophoregram), where (1) represents brain, (2) spinal cord, (3) lung and (4) liver. The figure (kb) at left indicates the size of the RNA molecular mass marker.

From 8-week-old C57 BL/6N mice (Charles River Japan), various tissues (brain, spinal cord, lung, and liver) were isolated and the total RNA was prepared by the acid-phenolguanidine chloroform method. From this total RNA, poly(A)$^+$RNA was prepared by means of an oligo(dT) span column (Pharmacia). This poly(A)$^+$RNA, 2.5 μg, was subjected to 1.2% formalin-modified agarose gel electrophoresis and blotted on a nylon membrane filter (Nippon Pall, Biodyne B) by capillary blotting for 19 hours. This nylon membrane filter was treated with ultraviolet light to fix the RNA blot and prehybridization was carried out in hybridization buffer (50% formamide, 5×SSPE (20×SSPE=3.6 M sodium chloride, 0.2 M sodium phosphate (pH 7.7), 20 mM EDTA), 5×Denhardt's solution, 0.5% SDS, 100 μg/ml heat-denatured salmon sperm DNA) at 42° C. On the other hand, for use as a probe, the SpeI 799 bp cDNA fragment of the cDNA coding for mouse ependymin-like protein (the cDNA fragment having a nucleotide sequence of bases no. 198 to no. 996 of the base sequence shown in FIG. 3) was labeled with [α-$^{32}$P]dCTP and Random Primer Labeling Kit (Amersham). Hybridization was carried out in a hybridization buffer (50% formamide, 5×SSPE, 5×Denhardt's solution, 0.5% SDS, 100 μg/ml heat-denatured salmon sperm DNA) containing the labeled probe at 42° C. for 18 hours. The filter was finally rinsed with 0.1×SSC-0.1% SDS solution at 50° C. and an autoradiogram was prepared to detect the band hybridizing with the probe. As a result, the mRNA with a mass of about 2.4 kb was most abundant in the spinal cord, followed by the brain, and weakly expressed in the lung as well (FIG. 8).

Example 7

Northern Hybridization of Various Parts of the Human Central Nervous System

Using membrane filters (MTN blot, Clonetek) preblotted with 2 μg of the poly(A)$^+$RNA from various segments of the human brain, prehybridization was carried out in hybridization buffer (50% formamide, 5×SSPE (20×SSPE=3.6 M sodium chloride, 0.2 M sodium phosphate (pH 7.7), 20 mM EDTA), 5×Denhardt's solution, 0.5% SDS, 100 μg/ml heat-denatured salmon sperm DNA) at 42° C.

Figure 9:
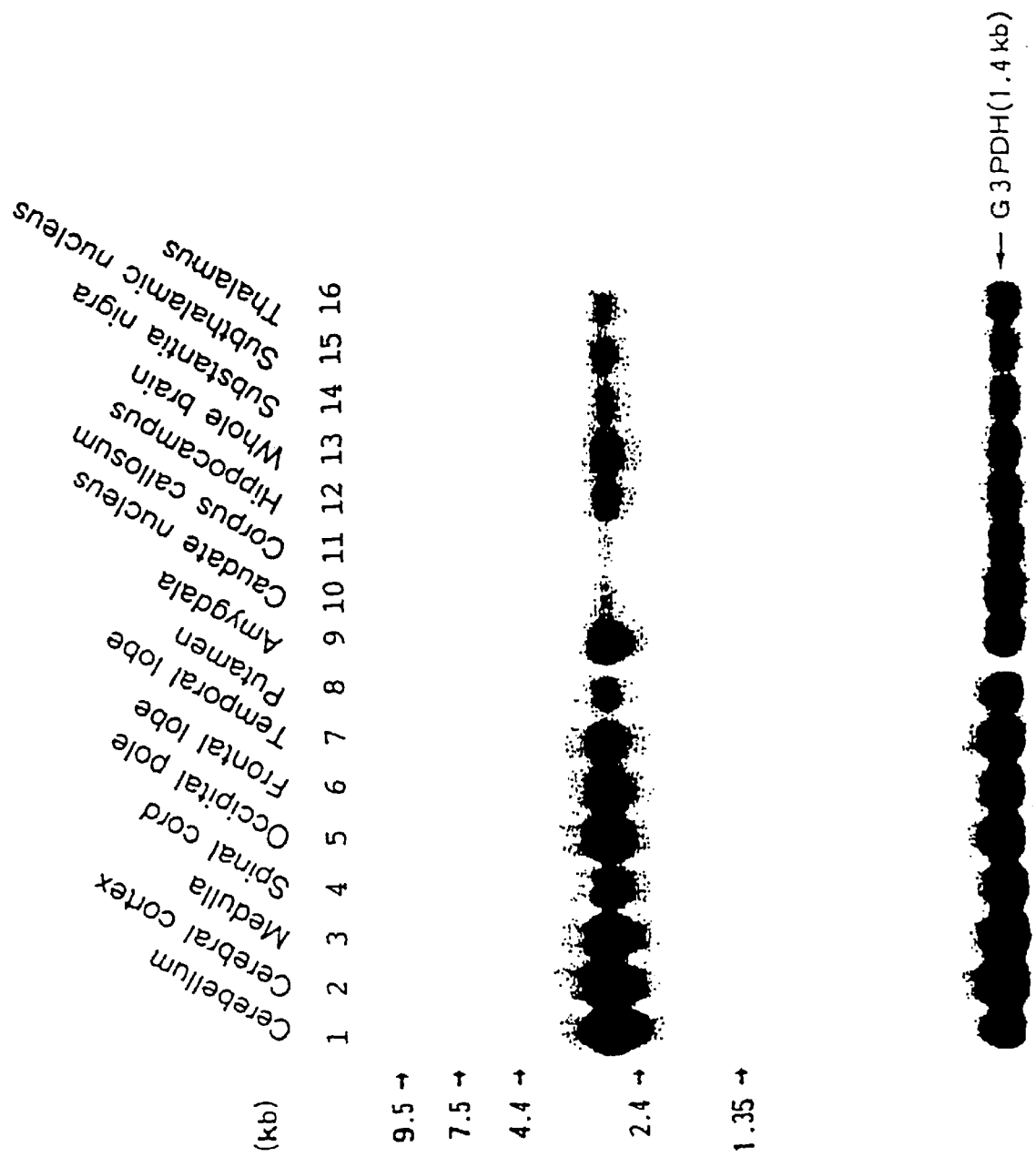
FIG. 9 shows the amounts of expression of the mRNA coding for the human ependymin-like protein of the present invention in various parts of the human CNS as determined by the Northern hybridization method (electrophoregram), where (1) represents cerebellum, (2) cerebral cortex, (3) medulla, (4) spinal cord, (5) occipital pole, (6) frontal lobe, (7) temporal lobe, (8) putamen, (9) amygdala, (10) caudate nucleus, (11) corpus callosum, (12) hippocampus, (13) whole brain, (14) substantia nigra, (15) subthalamic nucles and (16) thalamus. G3PDH represents the amount of expression of the mRNA coding for glyceraldehyde-3-phosphate dehydrogenase used as the internal marker.

On the other hand, as a probe, the BamHI-SpeI 383 bp cDNA fragment of the cDNA coding for human ependymin-like protein (the cDNA fragment having a nucleotide sequence of bases no. 643 to no. 1025 of the nucleotide sequence shown in FIG. 1) was labeled by using [α-$^{32}$P] dCTP (DuPont) and Random Primer Labeling Kit (Amersham). Prehybridization was carried out in a hybridization buffer (50% formamide, 5×SSPE, 5×Denhardt's solution, 0.1% SDS, 100 μg/ml heat-denatured salmon sperm DNA) at 42° C. for 12 hours. Then, hybridization was carried out in a hybridization buffer (50% formamide, 5×SSPE, 5×Denhardt's solution, 0.1% SDS, 100 μg/ml heat-denatured salmon sperm DNA) containing the labeled probe at 42° C. for 18 hours. The filter was finally rinsed with 0.1×SSC (20'SSC=3 M sodium chloride, 0.3 M sodium citrate)-0.1% SDS solution at 55° C. and an autoradiogram was prepared to detect the band hybridizing with the probe (FIG. 9). As a result, it was found that this mRNA had been expressed in most parts of the central nervous system, indicating its important role in nerve tissues.

Industrial Applicability

The protein, its partial peptide or a salt thereof of the present invention has physiological activities such as a nerve-extending or nerve-regenerating activity, a gliacyte stimulating activity, and so on. The protein, etc. or the DNA coding for the protein, etc. of the present invention is useful as a therapeutic or prophylactic agent for Alzheimer's disease, Parkinson's disease, Huntington's disease, amyotrophic lateral sclerosis (ALS), dementia or cerebellar degeneration. The antibody against the protein, etc. can be used in the assay of the protein, etc. in a test sample. Furthermore, the protein, etc. is useful as a screening reagent for compounds or their salts capable of promoting the function of the protein.

SEQUENCE LISTING

<160> NUMBER OF SEQ ID NOS: 35

<210> SEQ ID NO 1
<211> LENGTH: 187
<212> TYPE: PRT
<213> ORGANISM: Human

<400> SEQUENCE: 1

```
Ala Pro Arg Pro Cys Gln Ala Pro Gln Gln Trp Glu Gly Arg Gln Val
 1               5                  10                  15

Met Tyr Gln Gln Ser Ser Gly Arg Asn Ser Arg Ala Leu Leu Ser Tyr
             20                  25                  30

Asp Gly Leu Asn Gln Arg Val Arg Val Leu Asp Glu Arg Lys Ala Leu
         35                  40                  45

Ile Pro Cys Lys Arg Leu Phe Glu Tyr Ile Leu Leu Tyr Lys Asp Gly
     50                  55                  60

Val Met Phe Gln Ile Asp Gln Ala Thr Lys Gln Cys Ser Lys Met Thr
 65                  70                  75                  80

Leu Thr Gln Pro Trp Asp Pro Leu Asp Ile Pro Gln Asn Ser Thr Phe
                 85                  90                  95

Glu Asp Gln Tyr Ser Ile Gly Gly Pro Gln Glu Gln Ile Thr Val Gln
             100                 105                 110

Glu Trp Ser Asp Arg Lys Ser Ala Arg Ser Tyr Glu Thr Trp Ile Gly
         115                 120                 125

Ile Tyr Thr Val Lys Asp Cys Tyr Pro Val Gln Glu Thr Phe Thr Ile
130                 135                 140

Asn Tyr Ser Val Ile Leu Ser Thr Arg Phe Phe Asp Ile Gln Leu Gly
145                 150                 155                 160

Ile Lys Asp Pro Ser Val Phe Thr Pro Pro Ser Thr Cys Gln Met Ala
                 165                 170                 175

Gln Leu Glu Lys Met Ser Glu Asp Cys Ser Trp
             180                 185
```

<210> SEQ ID NO 2
<211> LENGTH: 190
<212> TYPE: PRT
<213> ORGANISM: Rat

<400> SEQUENCE: 2

```
Ser Pro Gly Thr Pro Gln Pro Cys Gln Ala Pro Gln Gln Trp Glu Gly
 1               5                  10                  15

Arg Gln Val Leu Tyr Gln Gln Ser Ser Gly His Asn Ser Arg Ala Leu
             20                  25                  30

Val Ser Tyr Asp Gly Leu Asn Gln Arg Val Arg Val Leu Asp Glu Arg
         35                  40                  45

Lys Ala Leu Ile Pro Cys Lys Arg Leu Phe Glu Tyr Ile Leu Leu Tyr
     50                  55                  60

Lys Asp Gly Val Met Phe Gln Ile Glu Gln Ala Thr Lys Leu Cys Ala
 65                  70                  75                  80

Lys Ile Pro Leu Ala Glu Pro Trp Asp Pro Leu Asp Ile Pro Gln Asn
                 85                  90                  95

Ser Thr Phe Glu Asp Gln Tyr Ser Ile Gly Gly Pro Gln Glu Gln Ile
             100                 105                 110

Met Val Gln Glu Trp Ser Asp Arg Arg Thr Ala Arg Ser Tyr Glu Thr
         115                 120                 125
```

```
Trp Ile Gly Val Tyr Thr Ala Lys Asp Cys Tyr Pro Val Gln Glu Thr
    130                 135                 140

Phe Ile Arg Asn Tyr Thr Val Val Leu Ser Thr Arg Phe Phe Asp Val
145                 150                 155                 160

Gln Leu Gly Ile Lys Asp Pro Ser Val Phe Thr Pro Ser Thr Cys
                165                 170                 175

Gln Thr Ala Gln Pro Glu Lys Met Lys Glu Asn Cys Ser Leu
            180                 185                 190

<210> SEQ ID NO 3
<211> LENGTH: 187
<212> TYPE: PRT
<213> ORGANISM: Mouse

<400> SEQUENCE: 3

Thr Pro Gln Pro Cys Gln Ala Pro Gln Gln Trp Glu Gly Arg Gln Val
1               5                   10                  15

Leu Tyr Gln Gln Ser Ser Gly His Asn Asn Arg Ala Leu Val Ser Tyr
                20                  25                  30

Asp Gly Leu Asn Gln Arg Val Arg Val Leu Asp Glu Arg Lys Ala Leu
            35                  40                  45

Ile Pro Cys Lys Arg Leu Phe Glu Tyr Ile Leu Leu Tyr Lys Glu Gly
        50                  55                  60

Val Met Phe Gln Ile Glu Gln Ala Thr Lys Gln Cys Ala Lys Ile Pro
65                  70                  75                  80

Leu Val Glu Ser Trp Asp Pro Leu Asp Ile Pro Gln Asn Ser Thr Phe
                85                  90                  95

Glu Asp Gln Tyr Ser Ile Gly Gly Pro Gln Glu Gln Ile Leu Val Gln
                100                 105                 110

Glu Trp Ser Asp Arg Arg Thr Ala Arg Ser Tyr Glu Thr Trp Ile Gly
            115                 120                 125

Val Tyr Thr Ala Lys Asp Cys Tyr Pro Val Gln Glu Thr Phe Ile Arg
130                 135                 140

Asn Tyr Thr Val Val Met Ser Thr Arg Phe Phe Asp Val Gln Leu Gly
145                 150                 155                 160

Ile Lys Asp Pro Ser Val Phe Thr Pro Ser Thr Cys Gln Ala Ala
                165                 170                 175

Gln Pro Glu Lys Met Ser Asp Gly Cys Ser Leu
            180                 185

<210> SEQ ID NO 4
<211> LENGTH: 13
<212> TYPE: PRT
<213> ORGANISM: Artificial Sequence
<220> FEATURE:
<223> OTHER INFORMATION: Common amino acid sequence between human, rat
      and mouse
<223> OTHER INFORMATION: ependymin-like protein

<400> SEQUENCE: 4

Pro Cys Gln Ala Pro Gln Gln Trp Glu Gly Arg Gln Val
1               5                   10

<210> SEQ ID NO 5
<211> LENGTH: 32
<212> TYPE: PRT
<213> ORGANISM: Artificial Sequence
<220> FEATURE:
<223> OTHER INFORMATION: Common amino acid sequence between human, rat
``` and mouse ependymin-like protein

<400> SEQUENCE: 5

```
Gln Ile Asp Gln Ala Thr Lys Gln Cys Ser Lys Met Thr Leu Thr Gln
  1               5                  10                  15
Pro Trp Asp Pro Leu Asp Ile Pro Gln Asn Ser Thr Phe Glu Asp Gln
             20                  25                  30
```

<210> SEQ ID NO 6
<211> LENGTH: 25
<212> TYPE: PRT
<213> ORGANISM: Artificial Sequence
<220> FEATURE:
<223> OTHER INFORMATION: Common amino acid sequence between human, rat
      and mouse
<223> OTHER INFORMATION: ependymin-like protein

<400> SEQUENCE: 6

```
Ser Tyr Glu Thr Trp Ile Gly Ile Tyr Thr Val Lys Asp Cys Tyr Pro
  1               5                  10                  15
Val Gln Glu Thr Phe Thr Ile Asn Tyr
             20                  25
```

<210> SEQ ID NO 7
<211> LENGTH: 17
<212> TYPE: PRT
<213> ORGANISM: Artificial Sequence
<220> FEATURE:
<223> OTHER INFORMATION: Common amino acid sequence between human, rat
      and mouse ependymin-like protein

<400> SEQUENCE: 7

```
Gln Leu Gly Ile Lys Asp Pro Ser Val Phe Thr Pro Pro Ser Thr Cys
  1               5                  10                  15
Gln
```

<210> SEQ ID NO 8
<211> LENGTH: 39
<212> TYPE: PRT
<213> ORGANISM: Artificial Sequence
<220> FEATURE:
<223> OTHER INFORMATION: Common amino acid sequence between human and
      rat ependymin-like protein

<400> SEQUENCE: 8

```
Ser Tyr Asp Gly Leu Asn Gln Arg Val Arg Val Leu Asp Glu Arg Lys
  1               5                  10                  15
Ala Leu Ile Pro Cys Lys Arg Leu Phe Glu Tyr Ile Leu Leu Tyr Lys
             20                  25                  30
Asp Gly Val Met Phe Gln Ile
             35
```

<210> SEQ ID NO 9
<211> LENGTH: 26
<212> TYPE: PRT
<213> ORGANISM: Artificial Sequence
<220> FEATURE:
<223> OTHER INFORMATION: Common amino acid sequence between human and
      rat ependymin-like protein

<400> SEQUENCE: 9

```
Pro Trp Asp Pro Leu Asp Ile Pro Gln Asn Ser Thr Phe Glu Asp Gln
  1               5                  10                  15
Tyr Ser Ile Gly Gly Pro Gln Glu Gln Ile
```

```
                    20                  25

<210> SEQ ID NO 10
<211> LENGTH: 200
<212> TYPE: PRT
<213> ORGANISM: Human

<400> SEQUENCE: 10

Trp Thr Leu Cys Gly Leu Cys Ser Leu Gly Ala Val Gly Ala Pro Arg
  1               5                  10                  15

Pro Cys Gln Ala Pro Gln Gln Trp Glu Gly Arg Gln Val Met Tyr Gln
                 20                  25                  30

Gln Ser Ser Gly Arg Asn Ser Arg Ala Leu Leu Ser Tyr Asp Gly Leu
             35                  40                  45

Asn Gln Arg Val Arg Val Leu Asp Glu Arg Lys Ala Leu Ile Pro Cys
         50                  55                  60

Lys Arg Leu Phe Glu Tyr Ile Leu Leu Tyr Lys Asp Gly Val Met Phe
 65                  70                  75                  80

Gln Ile Asp Gln Ala Thr Lys Gln Cys Ser Lys Met Thr Leu Thr Gln
                 85                  90                  95

Pro Trp Asp Pro Leu Asp Ile Pro Gln Asn Ser Thr Phe Glu Asp Gln
            100                 105                 110

Tyr Ser Ile Gly Gly Pro Gln Glu Gln Ile Thr Val Gln Glu Trp Ser
        115                 120                 125

Asp Arg Lys Ser Ala Arg Ser Tyr Glu Thr Trp Ile Gly Ile Tyr Thr
    130                 135                 140

Val Lys Asp Cys Tyr Pro Val Gln Glu Thr Phe Thr Ile Asn Tyr Ser
145                 150                 155                 160

Val Ile Leu Ser Thr Arg Phe Phe Asp Ile Gln Leu Gly Ile Lys Asp
                165                 170                 175

Pro Ser Val Phe Thr Pro Pro Ser Thr Cys Gln Met Ala Gln Leu Glu
            180                 185                 190

Lys Met Ser Glu Asp Cys Ser Trp
        195                 200

<210> SEQ ID NO 11
<211> LENGTH: 224
<212> TYPE: PRT
<213> ORGANISM: Human

<400> SEQUENCE: 11

Met Pro Gly Arg Ala Pro Leu Arg Thr Val Pro Gly Ala Leu Gly Ala
  1               5                  10                  15

Trp Leu Leu Gly Gly Leu Trp Ala Trp Thr Leu Cys Gly Leu Cys Ser
                 20                  25                  30

Leu Gly Ala Val Gly Ala Pro Arg Pro Cys Gln Ala Pro Gln Gln Trp
             35                  40                  45

Glu Gly Arg Gln Val Met Tyr Gln Gln Ser Ser Gly Arg Asn Ser Arg
         50                  55                  60

Ala Leu Leu Ser Tyr Asp Gly Leu Asn Gln Arg Val Arg Val Leu Asp
 65                  70                  75                  80

Glu Arg Lys Ala Leu Ile Pro Cys Lys Arg Leu Phe Glu Tyr Ile Leu
                 85                  90                  95

Leu Tyr Lys Asp Gly Val Met Phe Gln Ile Asp Gln Ala Thr Lys Gln
            100                 105                 110

Cys Ser Lys Met Thr Leu Thr Gln Pro Trp Asp Pro Leu Asp Ile Pro
```

```
                    115                 120                 125
Gln Asn Ser Thr Phe Glu Asp Gln Tyr Ser Ile Gly Gly Pro Gln Glu
    130                 135                 140

Gln Ile Thr Val Gln Glu Trp Ser Asp Arg Lys Ser Ala Arg Ser Tyr
145                 150                 155                 160

Glu Thr Trp Ile Gly Ile Tyr Thr Val Lys Asp Cys Tyr Pro Val Gln
                165                 170                 175

Glu Thr Phe Thr Ile Asn Tyr Ser Val Ile Leu Ser Thr Arg Phe Phe
            180                 185                 190

Asp Ile Gln Leu Gly Ile Lys Asp Pro Ser Val Phe Thr Pro Pro Ser
            195                 200                 205

Thr Cys Gln Met Ala Gln Leu Glu Lys Met Ser Glu Asp Cys Ser Trp
    210                 215                 220

<210> SEQ ID NO 12
<211> LENGTH: 224
<212> TYPE: PRT
<213> ORGANISM: Rat

<400> SEQUENCE: 12

Met Leu Thr Arg Ala Pro Arg Arg Leu Val Gln Gly Pro Arg Glu Thr
1               5                   10                  15

Trp Leu Gly Gly Leu Trp Val Trp Ile Leu Cys Gly Leu Gly Met
            20                  25                  30

Ala Gly Ser Pro Gly Thr Pro Gln Pro Cys Gln Ala Pro Gln Gln Trp
        35                  40                  45

Glu Gly Arg Gln Val Leu Tyr Gln Gln Ser Ser Gly His Asn Ser Arg
    50                  55                  60

Ala Leu Val Ser Tyr Asp Gly Leu Asn Gln Arg Val Arg Val Leu Asp
65                  70                  75                  80

Glu Arg Lys Ala Leu Ile Pro Cys Lys Arg Leu Phe Glu Tyr Ile Leu
                85                  90                  95

Leu Tyr Lys Asp Gly Val Met Phe Gln Ile Glu Gln Ala Thr Lys Leu
            100                 105                 110

Cys Ala Lys Ile Pro Leu Ala Glu Pro Trp Asp Pro Leu Asp Ile Pro
        115                 120                 125

Gln Asn Ser Thr Phe Glu Asp Gln Tyr Ser Ile Gly Gly Pro Gln Glu
    130                 135                 140

Gln Ile Met Val Gln Glu Trp Ser Asp Arg Arg Thr Ala Arg Ser Tyr
145                 150                 155                 160

Glu Thr Trp Ile Gly Val Tyr Thr Ala Lys Asp Cys Tyr Pro Val Gln
                165                 170                 175

Glu Thr Phe Ile Arg Asn Tyr Thr Val Val Leu Ser Thr Arg Phe Phe
            180                 185                 190

Asp Val Gln Leu Gly Ile Lys Asp Pro Ser Val Phe Thr Pro Pro Ser
            195                 200                 205

Thr Cys Gln Thr Ala Gln Pro Glu Lys Met Lys Glu Asn Cys Ser Leu
    210                 215                 220

<210> SEQ ID NO 13
<211> LENGTH: 224
<212> TYPE: PRT
<213> ORGANISM: Mouse

<400> SEQUENCE: 13

Met Pro Ala Arg Ala Pro Arg Arg Leu Val Gln Gly Pro Arg Gly Thr
```

```
  1               5                  10                 15
Trp Leu Leu Gly Ser Leu Trp Val Trp Val Leu Cys Gly Leu Gly Met
                 20                 25                 30

Ala Gly Ser Leu Gly Thr Pro Gln Pro Cys Gln Ala Pro Gln Gln Trp
         35                 40                 45

Glu Gly Arg Gln Val Leu Tyr Gln Gln Ser Ser Gly His Asn Asn Arg
     50                 55                 60

Ala Leu Val Ser Tyr Asp Gly Leu Asn Gln Arg Val Arg Val Leu Asp
 65                 70                 75                 80

Glu Arg Lys Ala Leu Ile Pro Cys Lys Arg Leu Phe Glu Tyr Ile Leu
                 85                 90                 95

Leu Tyr Lys Glu Gly Val Met Phe Gln Ile Glu Gln Ala Thr Lys Gln
                100                105                110

Cys Ala Lys Ile Pro Leu Val Glu Ser Trp Asp Pro Leu Asp Ile Pro
                115                120                125

Gln Asn Ser Thr Phe Glu Asp Gln Tyr Ser Ile Gly Gly Pro Gln Glu
        130                135                140

Gln Ile Leu Val Gln Glu Trp Ser Asp Arg Arg Thr Ala Arg Ser Tyr
145                150                155                160

Glu Thr Trp Ile Gly Val Tyr Thr Ala Lys Asp Cys Tyr Pro Val Gln
                165                170                175

Glu Thr Phe Ile Arg Asn Tyr Thr Val Val Met Ser Thr Arg Phe Phe
                180                185                190

Asp Val Gln Leu Gly Ile Lys Asp Pro Ser Val Phe Thr Pro Pro Ser
                195                200                205

Thr Cys Gln Ala Ala Gln Pro Glu Lys Met Ser Asp Gly Cys Ser Leu
        210                215                220
```

<210> SEQ ID NO 14
<211> LENGTH: 37
<212> TYPE: PRT
<213> ORGANISM: Human

<400> SEQUENCE: 14

```
Met Pro Gly Arg Ala Pro Leu Arg Thr Val Pro Gly Ala Leu Gly Ala
 1               5                  10                 15

Trp Leu Leu Gly Gly Leu Trp Ala Trp Thr Leu Cys Gly Leu Cys Ser
                 20                 25                 30

Leu Gly Ala Val Gly
        35
```

<210> SEQ ID NO 15
<211> LENGTH: 24
<212> TYPE: PRT
<213> ORGANISM: Human

<400> SEQUENCE: 15

```
Met Pro Gly Arg Ala Pro Leu Arg Thr Val Pro Gly Ala Leu Gly Ala
 1               5                  10                 15

Trp Leu Leu Gly Gly Leu Trp Ala
                 20
```

<210> SEQ ID NO 16
<211> LENGTH: 34
<212> TYPE: PRT
<213> ORGANISM: Rat

<400> SEQUENCE: 16

```
Met Leu Thr Arg Ala Pro Arg Arg Leu Val Gln Gly Pro Arg Glu Thr
 1               5                  10                  15

Trp Leu Gly Gly Leu Trp Val Trp Ile Leu Cys Gly Leu Gly Met
             20                  25                  30

Ala Gly

<210> SEQ ID NO 17
<211> LENGTH: 37
<212> TYPE: PRT
<213> ORGANISM: Mouse

<400> SEQUENCE: 17

Met Pro Ala Arg Ala Pro Arg Arg Leu Val Gln Gly Pro Arg Gly Thr
 1               5                  10                  15

Trp Leu Leu Gly Ser Leu Trp Val Trp Val Leu Cys Gly Leu Gly Met
             20                  25                  30

Ala Gly Ser Leu Gly
             35

<210> SEQ ID NO 18
<211> LENGTH: 561
<212> TYPE: DNA
<213> ORGANISM: Human

<400> SEQUENCE: 18
gccccgcgcc  cgtgccaggc  gccgcagcag  tgggaggggc  gccaggttat  gtaccagcaa      60
agtagcgggc  gcaacagccg  cgccctgctc  tcctacgacg  ggctcaacca  gcgcgtgcgg     120
gtgctggacg  agaggaaggc  gctgatcccc  tgcaagagat  tatttgaata  tattttgctg     180
tataaggatg  gagtgatgtt  tcagattgac  caagccacca  agcagtgctc  aaagatgacc     240
ctgacacagc  cctgggatcc  tcttgacatt  cctcaaaact  ccacctttga  agaccagtac     300
tccatcgggg  ggcctcagga  gcagatcacc  gtccaggagt  ggtcggacag  aaagtcagct     360
agatcctatg  aaacctggat  tggcatctat  acagtcaagg  attgctatcc  tgtccaggaa     420
acctttacca  taaactacag  tgtgatattg  tctacgcggt  tttttgacat  ccagctgggt     480
attaaagacc  cctcggtgtt  taccccctcca  agcacgtgcc  agatggccca  actggagaag     540
atgagcgaag  actgctcctg  g                                                  561

<210> SEQ ID NO 19
<211> LENGTH: 570
<212> TYPE: DNA
<213> ORGANISM: Rat

<400> SEQUENCE: 19
tccccgggaa  ccccgcagcc  atgccaggcg  ccccagcagt  gggagggacg  tcaggttctg      60
taccagcaga  gcagcgggca  caacagccgc  gccctggtgt  cctacgatgg  tctcaaccag     120
cgcgtgcggg  tgctggacga  aaggaaggcg  ctgatcccct  gcaagagatt  atttgaatac     180
attttactct  ataaggatgg  agtgatgttt  cagattgaac  aagccaccaa  actgtgtgca     240 aagatacccct  tggcagaacc  ctgggatcct  ctcgacattc  cccagaattc  tacctttgaa     300
gatcagtact  ctatcggagg  gcctcaggag  cagatcatgg  tccaggaatg  gtctgacagg     360
aggacagcca  gatcctatga  aacctggatt  ggcgtttata  cagccaagga  ttgctacccg     420
gtccaggaga  ccttcattag  gaactacact  gtggtcctgt  ccactcggtt  ctttgatgtg     480
cagttgggca  ttaaagaccc  ctctgtgttc  accccaccaa  gcacgtgcca  gacagcacag     540
```

```
ccagagaaga tgaaagagaa ctgctccctg                                          570

<210> SEQ ID NO 20
<211> LENGTH: 561
<212> TYPE: DNA
<213> ORGANISM: Mouse

<400> SEQUENCE: 20
accccacagc catgccaggc accccagcag tgggagggac gccaggttct gtaccagcag          60
agcagcgggc acaacaaccg cgccctggtg tcctacgatg gtctcaacca gcgcgtgcgg         120
gtgctggacg agaggaaagc gctgatcccc tgcaagagat tatttgaata cattttactc         180
tataaggagg gagtgatgtt tcagattgaa caagccacca acagtgtgc aaagatcccc          240 ttggtggaat cctgggatcc tctggacatt ccccagaatt ctacctttga agatcagtac         300
tccatcggag ggcctcagga gcagatcctg gtccaggagt ggtctgacag aagaacagca         360
agatcctatg aaacttggat cggcgtttat acagccaagg attgttatcc ggtccaggag         420
accttcatca ggaactacac tgtggtcatg tccacgcggt tctttgatgt gcagctaggc         480
attaaggacc cctctgtgtt caccccacca agcacatgcc aggcagcgca gccagagaag         540
atgagtgacg gctgctcctt g                                                  561

<210> SEQ ID NO 21
<211> LENGTH: 39
<212> TYPE: DNA
<213> ORGANISM: Artificial Sequence
<220> FEATURE:
<223> OTHER INFORMATION: Nucleotide sequence of DNA coding for common
      amino acid sequence between human, rat and mouse ependyin-like
      protein

<400> SEQUENCE: 21
ccgtgccagg cgccgcagca gtgggagggg cgccaggtt                                 39

<210> SEQ ID NO 22
<211> LENGTH: 96
<212> TYPE: DNA
<213> ORGANISM: Artificial Sequence
<220> FEATURE:
<223> OTHER INFORMATION: Nucleotide sequence of DNA coding for common
      amino acid sequence between human, rat and mouse ependymin-like
      protein

<400> SEQUENCE: 22
cagattgacc aagccaccaa gcagtgctca aagatgaccc tgacacagcc ctgggatcct          60
cttgacattc tcaaaactc caactttgaa gaccag                                    96

<210> SEQ ID NO 23
<211> LENGTH: 75
<212> TYPE: DNA
<213> ORGANISM: Artificial Sequence
<220> FEATURE:
<223> OTHER INFORMATION: Nucleotide sequence of DNA coding for common
      amino acid sequence between human, rat and mouse ependymin-like
      protein

<400> SEQUENCE: 23
tcctatgaaa cctggattgg catctataca gtcaaggatt gctatcctgt ccaggaaacc          60
tttaccataa actac                                                          75

<210> SEQ ID NO 24
```

```
<211> LENGTH: 51
<212> TYPE: DNA
<213> ORGANISM: Artificial Sequence
<220> FEATURE:
<223> OTHER INFORMATION: Nucleotide sequence of DNA coding for common
      amino acid sequence between human, rat and mouse ependyin-like
      protein

<400> SEQUENCE: 24
cagctgggta ttaaagaccc ctcggtgttt accccctccaa gcacgtgcca g            51

<210> SEQ ID NO 25
<211> LENGTH: 117
<212> TYPE: DNA
<213> ORGANISM: Artificial Sequence
<220> FEATURE:
<223> OTHER INFORMATION: Nucleotide sequence of DNA coding for common
      amino acid sequence between human and rat ependymin-like protein

<400> SEQUENCE: 25
tcctacgacg ggctcaacca gcgcgtgcgg gtgctggacg agaggaaggc gctgatcccc    60
tgcaagagat tatttgaata tattttgctg tataaggatg gagtgatgtt tcagatt      117

<210> SEQ ID NO 26
<211> LENGTH: 78
<212> TYPE: DNA
<213> ORGANISM: Artificial Sequence
<220> FEATURE:
<223> OTHER INFORMATION: Nucleotide sequence of DNA coding for common
      amino acid sequence between human and rat ependymin-like protein

<400> SEQUENCE: 26
ccctgggatc ctcttgacat tcctcaaaac tccacctttg aagaccagta ctccatcggg    60
gggcctcagg agcagatc                                                  78

<210> SEQ ID NO 27
<211> LENGTH: 600
<212> TYPE: DNA
<213> ORGANISM: Human

<400> SEQUENCE: 27
tggaccctgt gcggcctgtg cagcctgggg gcggtgggag ccccgcgccc gtgccaggcg    60
ccgcagcagt gggaggggcg ccaggttatg taccagcaaa gtagcgggcg caacagccgc   120
gccctgctct cctacgacgg gctcaaccag cgcgtgcggg tgctggacga gaggaaggcg   180
ctgatcccct gcaagagatt atttgaatat attttgctgt ataaggatgg agtgatgttt   240
cagattgacc aagccaccaa gcagtgctca aagatgaccc tgacacagcc tgggatcct   300 cttgacattc tcaaaactc cacctttgaa gaccagtact ccatcggggg gcctcaggag   360
cagatcaccg tccaggagtg gtcggacaga aagtcagcta gatcctatga aacctggatt   420
ggcatctata cagtcaagga ttgctatcct gtccaggaaa cctttaccat aaactacagt   480
gtgatattgt ctacgcggtt ttttgacatc cagctgggta ttaaagaccc ctcggtgttt   540 accccctccaa gcacgtgcca gatggcccaa ctggagaaga tgagcgaaga ctgctcctgg   600

<210> SEQ ID NO 28
<211> LENGTH: 672
<212> TYPE: DNA
<213> ORGANISM: Human

<400> SEQUENCE: 28
atgccaggac gcgctcccct ccgcaccgtc ccgggcgccc tgggtgcctg gctgctgggc    60
```

```
ggcctctggg cctggaccct gtgcggcctg tgcagcctgg gggcggtggg agcccgcgc     120 ccgtgccagg cgccgcagca gtgggagggg cgccaggtta tgtaccagca aagtagcggg    180
cgcaacagcc gcgccctgct ctcctacgac gggctcaacc agcgcgtgcg ggtgctggac    240
gagaggaagg cgctgatccc ctgcaagaga ttatttgaat atattttgct gtataaggat    300
ggagtgatgt tcagattga ccaagccacc aagcagtgct caaagatgac cctgacacag     360
ccctgggatc ctcttgacat tcctcaaaac tccacctttg aagaccagta ctccatcggg    420
gggcctcagg agcagatcac cgtccaggag tggtcggaca gaaagtcagc tagatcctat    480
gaaacctgga ttggcatcta tacagtcaag gattgctatc ctgtccagga aacctttacc    540
ataaactaca gtgtgatatt gtctacgcgg ttttttgaca tccagctggg tattaaagac    600
ccctcggtgt ttacccctcc aagcacgtgc cagatggccc aactggagaa gatgagcgaa    660
gactgctcct gg                                                        672

<210> SEQ ID NO 29
<211> LENGTH: 672
<212> TYPE: DNA
<213> ORGANISM: Rat

<400> SEQUENCE: 29
atgctcacac gcgctccccg ccgcctggtc caggggcccc gggagacctg gctgcttggc    60
ggcctctggg tctggatatt gtgcggcctg gggatggcgg gctccccggg aaccccgcag    120
ccatgccagg cgccccagca gtgggaggga cgtcaggttc tgtaccagca gagcagcggg    180
cacaacagcc gcgccctggt gtcctacgat ggtctcaacc agcgcgtgcg ggtgctggac    240
gaaaggaagg cgctgatccc ctgcaagaga ttatttgaat acattttact ctataaggat    300
ggagtgatgt tcagattga acaagccacc aaactgtgtg caaagatacc cttggcagaa    360
ccctgggatc ctctcgacat tccccagaat tctacctttg aagatcagta ctctatcgga    420
gggcctcagg agcagatcat ggtccaggaa tggtctgaca ggaggacagc cagatcctat    480
gaaacctgga ttggcgttta tacagccaag gattgctacc cggtccagga gaccttcatt    540
aggaactaca ctgtggtcct gtccactcgg ttctttgatg tgcagttggg cattaaagac    600
ccctctgtgt tcaccccacc aagcacgtgc cagacagcac agccagagaa gatgaaagag    660
aactgctccc tg                                                        672

<210> SEQ ID NO 30
<211> LENGTH: 672
<212> TYPE: DNA
<213> ORGANISM: Mouse

<400> SEQUENCE: 30
atgcccgcgc gcgctccccg ccgcctggtc caggggcctc ggggacctg gctgctggga    60 agcctctggg tctgggtgct gtgcggcctg gggatggcgg gctccctggg aaccccacag    120
ccatgccagg cgccccagca gtgggaggga cgccaggttc tgtaccagca gagcagcggg    180
cacaacaacc gcgccctggt gtcctacgat ggtctcaacc agcgcgtgcg ggtgctggac    240
gagaggaaag cgctgatccc ctgcaagaga ttatttgaat acattttact ctataaggag    300
ggagtgatgt tcagattga acaagccacc aaacagtgtg caaagatccc cttggtggaa    360
tcctgggatc ctctggacat tccccagaat tctacctttg aagatcagta ctccatcgga    420
gggcctcagg agcagatcct ggtccaggag tggtctgaca gaagaacagc aagatcctat    480
```

-continued

```
gaaacttgga tcggcgttta tacagccaag gattgttatc cggtccagga gaccttcatc    540
aggaactaca ctgtggtcat gtccacgcgg ttctttgatg tgcagctagg cattaaggac    600
ccctctgtgt tcaccccacc aagcacatgc caggcagcgc agccagagaa gatgagtgac    660
ggctgctcct tg                                                        672
```

<210> SEQ ID NO 31
<211> LENGTH: 111
<212> TYPE: DNA
<213> ORGANISM: Human

<400> SEQUENCE: 31

```
atgccaggac gcgctcccct ccgcaccgtc ccgggcgccc tgggtgcctg gctgctgggc    60
ggcctctggg cctggaccct gtgcggcctg tgcagcctgg ggcggtggg a              111
```

<210> SEQ ID NO 32
<211> LENGTH: 72
<212> TYPE: DNA
<213> ORGANISM: Human

<400> SEQUENCE: 32

```
atgccaggac gcgctcccct ccgcaccgtc ccgggcgccc tgggtgcctg gctgctgggc    60
ggcctctggg cc                                                        72
```

<210> SEQ ID NO 33
<211> LENGTH: 102
<212> TYPE: DNA
<213> ORGANISM: Rat

<400> SEQUENCE: 33

```
atgctcacac gcgctccccg ccgcctggtc caggggcccc gggagacctg gctgcttggc    60
ggcctctggg tctggatatt gtgcggcctg gggatggcgg gc                       102
```

<210> SEQ ID NO 34
<211> LENGTH: 111
<212> TYPE: DNA
<213> ORGANISM: Mouse

<400> SEQUENCE: 34

```
atgcccgcgc gcgctccccg ccgcctggtc caggggcctc gggggacctg gctgctggga    60
agcctctggg tctgggtgct gtgcggcctg gggatggcgg gctccctggg a             111
```

<210> SEQ ID NO 35
<211> LENGTH: 21
<212> TYPE: DNA
<213> ORGANISM: Human

<400> SEQUENCE: 35

```
aggtggagtt ttgaggaatg t                                              21
```

What is claimed is:

1. An isolated protein consisting of an amino acid sequence depicted as SEQ ID NO.: 1, or a salt thereof.

2. The isolated protein according to claim 1, which has a nerve-extending activity.

3. An isolated precursor protein consisting of an amino acid sequence selected from the amino acid sequences depicted as SEQ ID NO.: 10 or SEQ ID NO.: 11, or a salt thereof.

* * * * *